United States Patent [19]
Lebl et al.

[11] Patent Number: 6,045,755
[45] Date of Patent: Apr. 4, 2000

[54] APPARATUS AND METHOD FOR COMBINATORIAL CHEMISTRY SYNTHESIS

[75] Inventors: Michael Lebl, San Diego, Calif.; Vit Pokorny, Prague, Czech Rep.; Viktor Krchnak, San Diego, Calif.

[73] Assignee: Trega Biosciences,, Inc., San Diego, Calif.

[21] Appl. No.: 08/815,975

[22] Filed: Mar. 10, 1997

[51] Int. Cl.⁷ .............................. G01N 35/00; B01J 19/00; F16K 3/02; B01L 3/14

[52] U.S. Cl. .............................. 422/65; 422/81; 422/103; 422/104; 422/131; 422/134; 436/43; 436/47; 436/49; 436/174; 439/180

[58] Field of Search .................................. 422/63, 65, 67, 422/68.1, 81, 100, 101, 102, 103, 104, 131, 134, 135; 436/43, 47, 48, 49, 174, 179, 180

[56] References Cited

U.S. PATENT DOCUMENTS

| | | |
|---|---|---|
| 3,483,997 | 12/1969 | Ritter . |
| 3,596,673 | 8/1971 | Laucournet et al. . |
| 3,603,471 | 9/1971 | Harris et al. . |
| 3,685,786 | 8/1972 | Woodson . |
| 3,757,981 | 9/1973 | Harris et al. . |
| 3,965,925 | 6/1976 | Gooch . |
| 4,096,966 | 6/1978 | Lessnig et al. . |
| 4,631,211 | 12/1986 | Houghton . |
| 4,642,220 | 2/1987 | Björkman . |
| 4,835,707 | 5/1989 | Amano et al. ............................ 364/497 |
| 5,122,342 | 6/1992 | McCulloch et al. ....................... 422/65 |
| 5,137,698 | 8/1992 | Ansorge et al. ......................... 422/242 |
| 5,202,418 | 4/1993 | Lebl et al. . |
| 5,252,296 | 10/1993 | Zuckerman et al. . |
| 5,288,514 | 2/1994 | Ellman . |
| 5,338,831 | 8/1994 | Lebl et al. . |
| 5,342,585 | 8/1994 | Lebl et al. . |

(List continued on next page.)

FOREIGN PATENT DOCUMENTS

| | | |
|---|---|---|
| 0 246 110 A1 | 11/1987 | European Pat. Off. . |
| 0 355 266 | 2/1990 | European Pat. Off. . |
| 0 529 504 | 3/1993 | European Pat. Off. . |
| 0 557 828 | 9/1993 | European Pat. Off. . |
| 0 606 534 | 7/1994 | European Pat. Off. . |
| 0 622 623 | 11/1994 | European Pat. Off. . |

(List continued on next page.)

OTHER PUBLICATIONS

Newman, 1990, "Send in the Robots", Anal. Chem. 62:29a–34a.

Willard et al., 1996, "Combinatorial Chemistry: A Rational Approach to Chemical Diversity", Eur. J. Med. Chem. 31:87–98.

(List continued on next page.)

*Primary Examiner*—Long V. Le
*Attorney, Agent, or Firm*—Pennie & Edmonds LLP

[57] ABSTRACT

In a first embodiment, this invention includes an integrated robot apparatus for performing combinatorial chemistry synthesis protocols and having interchangeable workstations, robot arm tools, and reaction vessels and reaction vessel arrays. The work-stations and tools are specialized to perform tasks necessary for the synthesis in a plurality of the reaction vessels grouped in a plurality of the reaction vessel arrays. Preferably, these elements function interchangeably because they have standardized sizes and conformation. The work-stations and tools include those for fluid dispensing or aspirating from individual reaction vessels or from all the reaction vessels in an array simultaneously. The reaction vessels can include, alternatively, stackable, ball-sealed reaction vessels, microtitre-like reaction vessel arrays, arrays of independent reaction vessels, valve-sealed reaction vessels, septum-sealed reaction vessels, and syringe reaction vessels. In alternative embodiments, this invention includes these work-stations, tools, reaction vessels and reaction vessel arrays in various combinations or sub-combinations either for use in partially integrated robots or for manual or standalone use.

28 Claims, 22 Drawing Sheets

U.S. PATENT DOCUMENTS

| | | |
|---|---|---|
| 5,348,550 | 9/1994 | Ikeda et al. . |
| 5,395,594 | 3/1995 | Nokihara et al. ........................ 422/135 |
| 5,417,922 | 5/1995 | Markin et al. . |
| 5,422,075 | 6/1995 | Saito et al. ................................ 422/52 |
| 5,429,803 | 7/1995 | Guirguis . |
| 5,431,201 | 7/1995 | Torchia et al. ............................ 141/98 |
| 5,432,098 | 7/1995 | Wilks . |
| 5,472,669 | 12/1995 | Miki et al. ................................ 422/63 |
| 5,496,473 | 3/1996 | Chow . |
| 5,503,805 | 4/1996 | Sugarman et al. . |
| 5,510,240 | 4/1996 | Lam et al. . |
| 5,529,756 | 6/1996 | Brennan .................................. 422/131 |
| 5,578,270 | 11/1996 | Reichler et al. .......................... 422/67 |
| 5,656,427 | 8/1997 | Hammond et al. . |
| 5,656,741 | 8/1997 | Chow et al. . |
| 5,779,977 | 7/1998 | Haff et al. .............................. 422/68.1 |
| 5,792,431 | 8/1998 | Moore et al. ............................ 422/134 |
| 5,795,547 | 8/1998 | Moser et al. ............................ 422/104 |

FOREIGN PATENT DOCUMENTS

| | | |
|---|---|---|
| 2010447 | 2/1970 | France . |
| 37 23 886 C1 | 9/1988 | Germany . |
| 38 05 808 | 9/1989 | Germany . |
| 40 08 085 | 9/1991 | Germany . |
| 88 08 872 | 10/1993 | Germany . |
| 59-000638 | 4/1984 | Japan . |
| 664 094 | 2/1988 | Switzerland . |
| 1 383 937 | 2/1974 | United Kingdom . |
| WO 90/02605 | 3/1990 | WIPO . |
| WO 90/03834 | 4/1990 | WIPO . |
| WO 93/12427 | 6/1993 | WIPO . |
| WO 94/06451 | 3/1994 | WIPO . |
| WO 94/08759 | 4/1994 | WIPO . |
| WO 96/22157 | 7/1996 | WIPO . |
| WO 97/09353 | 3/1997 | WIPO . |
| WO 97/10896 | 3/1997 | WIPO . |
| WO 97/14041 | 4/1997 | WIPO . |
| WO 97/24180 | 7/1997 | WIPO . |

OTHER PUBLICATIONS

Zuckerman, 1992, "Design, Construction and Application of a Fully Automated Equimolar Peptide Mixture Synthesizer", Int. J. Peptide Protein Res. 40:497–506.

Armstrong et al., 1996, "Multiple–Component Condensation Strategies for Combinatorial Library Synthesis", Acc. Chem. Res. 29:123–131.

Bianchi et al., 1995, "A Conformationally Homogeneous Combinatorial Peptide Library", J. Mol. Biol. 247:154–160.

Bunin and Ellman, 1992, "A General and Expedient Method for the Solid–Phase Synthesis of 1,4–Benzodiazepine Derivatives", J. Am. Chem. Soc. 114:10997–10998.

Cargill and Maiefski, 1996, "Automated Combinatorial Chemistry on Solid Phase", LRA 8:139–148.

Combinatorial Chemistry, 1996, C&EN, Feb. 12.

Eichler et al., 1996, "Inclusion Volume Solid–Phase Synthesis", J. Peptide Sci. 2:240–244.

Ellman, 1996, "Design, Synthesis, and Evaluation of Small–Molecule Libraries", Acc. Chem. Res. 29:132–143.

Fernandez et al., 1992, "Magnetic Resonance Studies of Polypeptides Adsorbed on Silica and Hydroxyapatite Surfaces", J. Am. Chem. Soc. 114:9634–9642.

Fruchtel and Jung, 1996, "Organic Chemistry on Solid Supports", Angew. Chem. Int. Ed. Engl. 35:17–42.

Hermkens et al., 1996, "Solid–Phase Organic Reactions: A Review of the Recent Literature", Tetrahedron 52:4527–4554.

Hodgkin et al., 1993, "A Monte Carlo Pharmacophore Generation Procedure: Application to the Human PAF Receptor", J. Computer–Aided Mol. Des. 7:515–534.

Krchnak et al., 1996, "MARS—Multiple Automated Robotic Synthesizer for Continuous Flow of Peptides", Peptide Res. 9:45–49.

Krchnak and Lebl, 1995, "Synthetic Library Techniques: Subjective (Biased and Generic) Thoughts and Views", Mol. Diversity 1:193–216.

Lam et al., 1991, "A New Type of Synthetic Peptide Library for Identifying Ligand–Binding Activity", Science 354:82–84.

Rinnova and Lebl, 1995, "Molecular Diversity and Libraries of Structures: Synthesis and Screening", Collect. Czech. Chem. Commun. 61:171–231.

Sepetov et al., 1995, "Library of Libraries: Approach to Synthetic Combinantorial Library Design and Screening of 'Pharmacophore' Motifs", Proc. Natl. Acad. Sci. USA 92:5426–5430.

Simon et al., 1992, "Peptoids: A Modular Approach to Drug Discovery", Proc. Natl. Acad. Sci. USA 89:9367–9371.

Thompson and Ellman, 1996, "Synthesis and Applications of Small Molecule Libraries", Chem. Rev. 96:555–600.

Wilson et al., 1993, "The Calculation and Synthesis of a Template Molecule", Tetrahedron 49:3655–3663.

Zuckerman et al., 1992, "Efficient Method for the Preparation of Peptoids [Oligo(N–Substituted Glycines)] by Submonomer Solid–Phase Synthesis", J. Am. Chem. Soc. 114:10646–10647.

Knapp et al., 1993, *Int. J. Peptide Protein Res.*, 42:259–263.

Seliger et al., 1986, *Chemica Scripta*, 26:569–577.

Seliger et al., 1989, *Bioengineering*, 5:144–147.

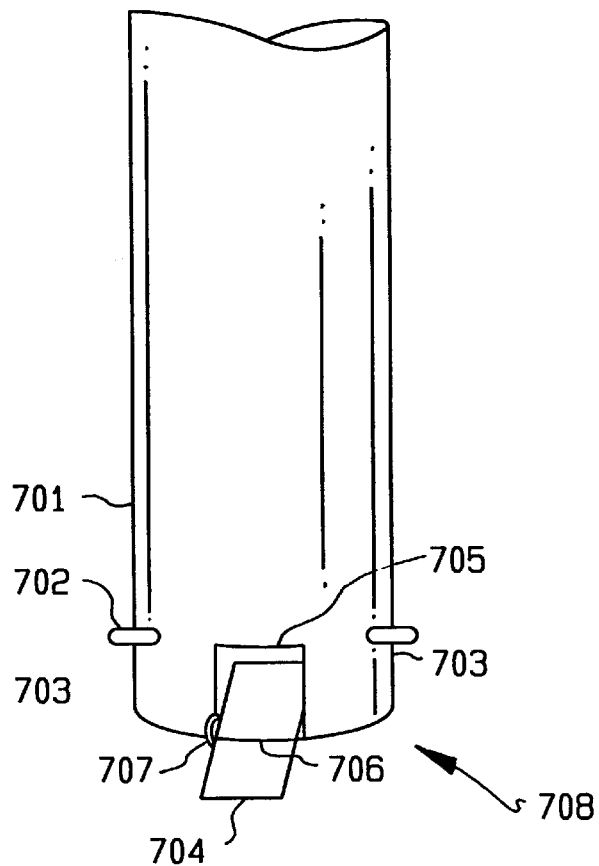
FIG. 19A1
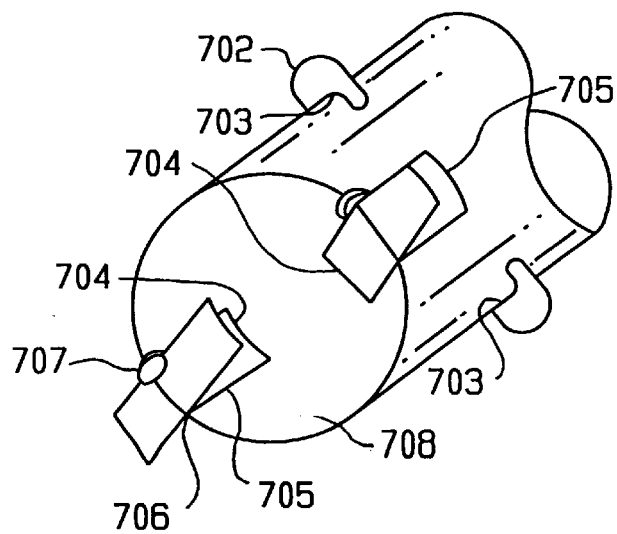
FIG. 19A2

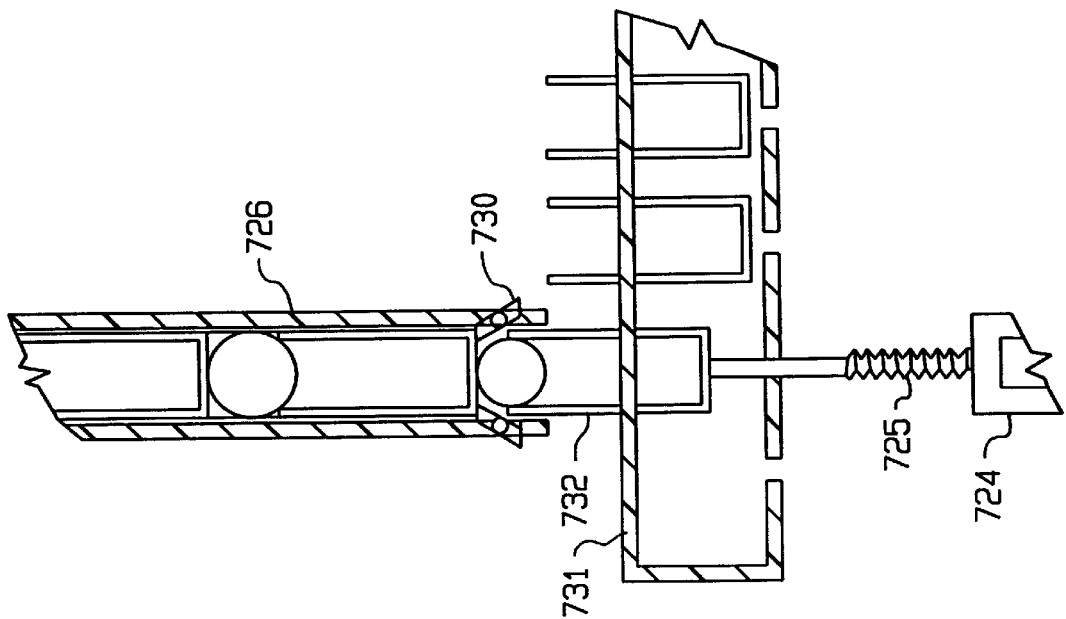
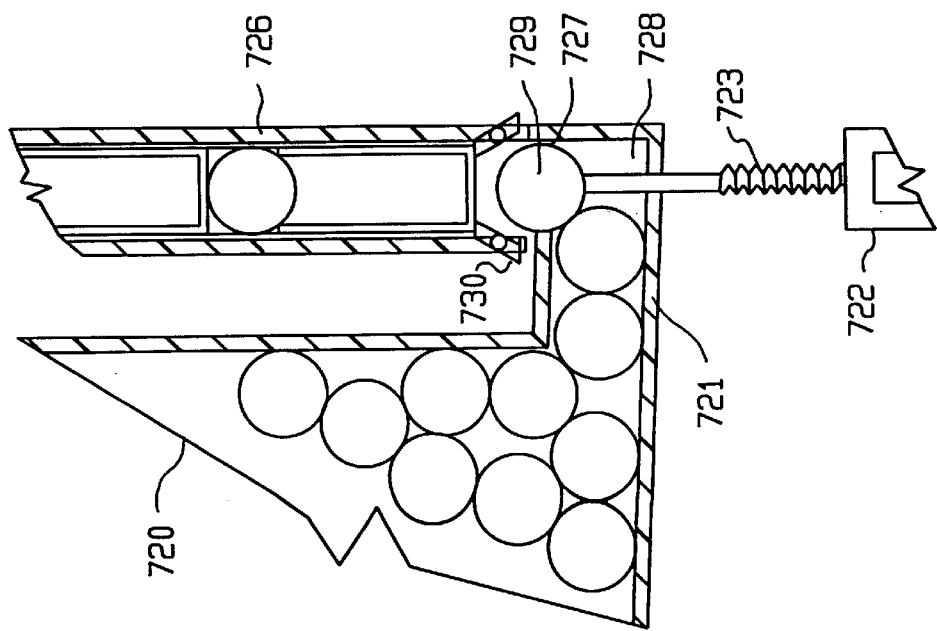

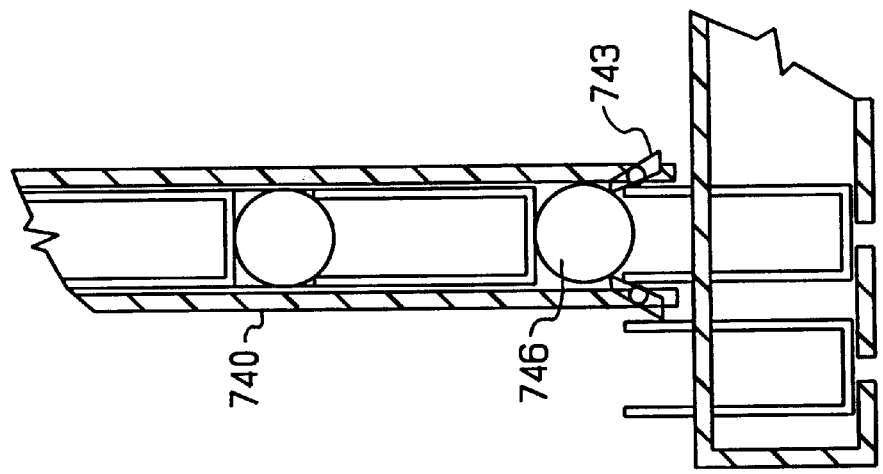
FIG. 19C3
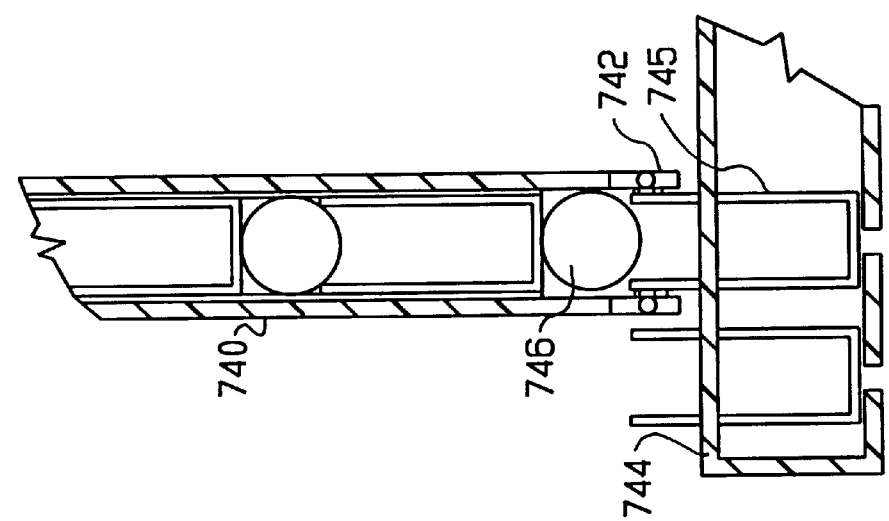
FIG. 19C2
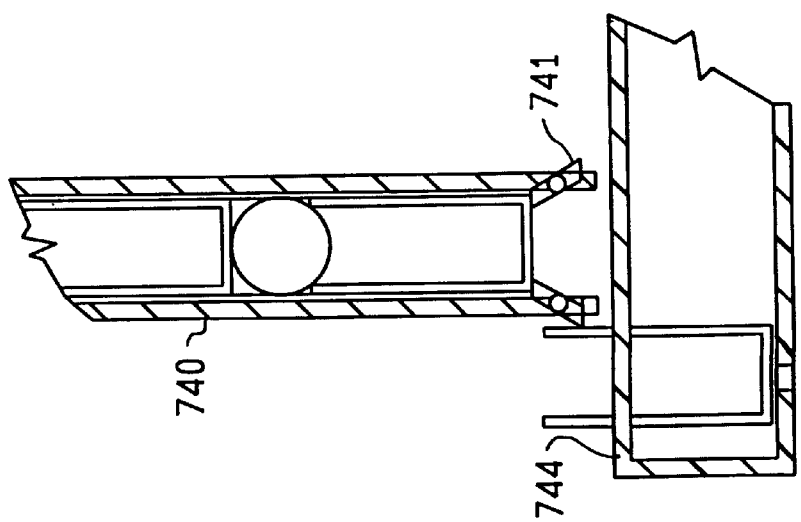
FIG. 19C1

APPARATUS AND METHOD FOR COMBINATORIAL CHEMISTRY SYNTHESIS

1. FIELD OF THE INVENTION

The field of this invention relates to automated apparatus for chemical synthesis; more particularly it relates both to a flexible, high-throughput, synthetic robot apparatus for combinatorial chemistry synthesis and also, generally, to apparatus for performing various manipulations during such synthesis, whether as part of an automated or of a manual procedure.

2. BACKGROUND

Protocols for combinatorial chemistry synthesis are recently developed chemical processes for individually synthesizing a potentially combinatorially-large number of chemical compounds. These methods proceed by a sequence of steps, each step adding a particular, selected one of a plurality of building blocks, i.e. small organic molecules, to a growing, intermediate compound. Thereby, the number of potential final compounds is a product of terms, one term for each synthesis step representing the number of possible building blocks that can be added at that step. For example, for peptides, since each step can typically select from the same number of amino acid building blocks, the number of potential final peptides is the number possible amino acid building blocks raised to a power equal to the number of addition steps.

These addition step reactions typically proceed by combining the partially-synthesized, intermediate compound with the building block having an attached activating residue. (Hereinafter, building blocks are assumed to have necessary activating residues attached.) Also added to an addition step reaction are activating reagents and other reagents and solvents. The building blocks are added in a molar excess to the partially synthesized compound present so that the thermodynamically favorable building block addition proceeds substantially to completion. After addition of one building block, the intermediate compound is separated from the spent reaction solution and prepared for the addition of a further building block. Often, the intermediate compound is attached to a solid-phase support by, e.g., a cleaveable linking residue, in order to simplify separation of intermediate compound from spent addition reaction solutions. In such solid-phase protocols a final step of cleaving the linking residue frees the final compound.

Building blocks (activated as necessary), activating and other reagents, and reaction conditions have been recently perfected for a wide variety of classes of final compounds. Exemplary of such reactions and protocols are the following for addition of natural and artificial amino acids to form peptides: Lam et al., 1991, A new type of synthetic peptide library for identifying ligand-binding activity, *Nature* 354: 82–84.; U.S. Pat. 5,510,240 to Lam et al. for Method of screening a peptide library; Lam et al., 1994, Selectide technology: Bead-binding screening. *Methods: A Companion to Methods in Enzymoloqy* 6: 372–380. For protocols for the synthesis of benzodiazepine moieties, see, e.g.: Bunin et al., 1992, A general and expedient method for the solid phase synthesis of 1,4-benzodiazepine derivatives, *J. Amer. Chem. Soc.,* 114: 10997–10998.; U.S. Pat. 288,514 to Ellman for Solid phase and combinatorial synthesis of benzodiazepine compounds on a solid support. Also, for protocols for the addition of N-substituted glycines to form peptoids, see, e.g., Simon, et al., 1992, Peptoids: A modular approach to drug discovery. *Proc. Natl. Acad. Sci. USA,* 89: 9367–9371; Zuckermann et al., 1992, Efficient method for the preparation of peptoids [oligo(N-substituted glycines)] by submonomer solid-phase synthesis. *J. Amer. Chem. Soc.,* 114: 10646–10647; WO PCT94/06,451 to Moos et al. for Synthesis of N-substituted polyamide monomers, useful as solvents, additives for food, enzyme inhibitors etc. Approaches for synthesis of small molecular libraries were recently reviewed by, e.g., Krchnak et al., 1996, Synthetic library techniques: Subjective (biased and generic) thoughts and views, *Molecular Diversity,* 1: 193–216; Ellman, 1996, Design, synthesis, and evaluation of small-molecule libraries, *Account. Chem. Res.,* 29: 132–143; Armstrong et al., 1996, Multiple-component condensation strategies for combinatorial library synthesis, *Account. Chem. Res.,* 29: 123–131.; Fruchtel et al., 1996, Organic chemistry on solid supports, *Angew. Chem. Int. Ed.,* 35: 17–42; Thompson et al., 1996, Synthesis and application of small molecule libraries, *Chem. Rev.,* 96 :555–600; Rinnova et al., 1996, Molecular diversity and libraries of structures: Synthesis and screening, *Collect. Czech. Chem. Commun.,* 61: 171–231; Hermkens et al., 1996, Solid-phase organic reactions: A review of the recent literature, *Tetrahedron,* 52: 4527–4554.

Predictable, algorithmic synthesis of a large number of individual compounds, which are subsequently collected into a library of compounds, is of interest and utility in several fields, in particular in the field of pharmaceutical lead-compound selection. A pharmaceutical lead-compound for a drug is a compound which exhibits a particular biologic activity of pharmaceutical interest and which can serve as a starting point for the selection and synthesis of a drug compound, which in addition to the particular biological activity has pharmacologic and toxicologic properties suitable for administration to humans or animals. It is apparent that synthesis of large numbers of compounds and screening for their biological activities in a controlled biological system can be of assistance in lead compound selection. Instead of turning to botanical or other natural sources, the pharmaceutical chemist can use combinatorial protocols to generate in the laboratory compounds to screen for desired activities. See, e.g., Borman, 1996, Combinatorial Chemists Focus on Small Molecules, Molecular Recognition, and Automation, *Chemical & Engineering News,* Feb. 12, 1996, 29–54.

To achieve the benefits of these recently developed combinatorial protocols, automated synthesis apparatus is advantageous. Dealing manually with hundreds, thousands, or perhaps tens of thousands of separate compounds is expensive, time consuming, and prone to error. Therefore, synthesis robots for automating one or more steps of combinatorial protocols have been recently developed. Examples of such recently developed robots are described in: Cargill et al., 1996, Automated Combinatorial Chemistry on Solid-Phase, *Laboratory Robotics and Automation,* 8: 139–148; U.S. Pat. 5,503,805 to Sugarman et al.; U.S. Pat. 5,252,296 to Zuckermann et al. for Method and apparatus for biopolymer synthesis; WO PCT 93/12,427 to Zuckermann et al., for Automated apparatus for use in peptide synthesis; Krchnak et al., 1996, MARS—Multiple Automatic Robot Synthesizer. Continuous Flow of Peptide, *Peptide Res.* 9: 45–49.

However, these and other existing combinatorial synthesis robots have significant limitations. First, they perform such syntheses sequentially and batchwise. In other words, at any one time, such robots can process only one limited group of synthesis reactions. Typically only 10–96 reactions can be processed at one time, after which the robotic apparatus must be cleaned and reconditioned in order to synthesize the next batch of compounds. Second, such robots are often constructed of specialized, single-function elements, not otherwise commercially available. For example, there can be one set of specially designed and constructed automatic manipulators for each single manipulation required by a synthetic protocol, thereby requiring a sequential passage of a batch of reactions through the robot. Also, typically, the reaction vessels, in which the synthetic addition reactions are performed, are specially designed, constructed, and arrayed in large, cumbersome, and expensive reaction vessel arrays or assemblies. Alternatively, such robots utilize complex tubing, valving, and pumping arrangements for fluid distribution, which are expensive to manufacture and maintain. A third limitation is that these robots typically provide only limited reaction conditions, such as limited temperature ranges and an inability to prevent atmospheric exposure.

In summary, current synthesis robots for combinatorial chemistry protocols are slow and expensive, limiting the promise of combinatorial chemistry, especially as applied to drug selection and design. Existing robots are slow because of sequential, batchwise synthesis, because of single-function robotic devices, and because of a limited capability to process large numbers of synthesis reactions according to multiple protocols. They are expensive because their robot actuators, reaction vessels, and reaction vessel arrays are specially designed for this one application, limiting use of existing, inexpensive, commercially available components.

3. SUMMARY OF THE INVENTION

It is an object of this invention to provide a combinatorial chemistry synthesis robot which overcomes the previously described problems. The robot of this invention is capable of the simultaneous, high throughput synthesis of compounds according to a plurality of synthesis protocols, each such protocol utilizing a plurality of building blocks and reagents. The robot is not limited to the synthesis of compounds according to one synthesis protocol at one time. The multi-protocol and high throughput capabilities of the robot are made possible by a flexible and programmable architecture, in which synthetic steps in reaction vessels are performed at appropriate modules or work stations and in an appropriate sequence according to the particular protocol being performed. In embodiments directed toward solid-phase synthesis, the robot is additionally capable of the production of combinations of single or multiple compounds per solid-phase bead or single or multiple compounds per each reaction vessel. The robot provides extended reaction conditions, including temperatures from −50 to +150° C., and inert atmospheres, including nitrogen or argon. Preferably, the robot is further capable of synthesizing between 3,000 and 5,000 compounds per day, and less preferably, is capable of synthesizing at least 1,000 compounds per day.

It is a further object of this invention to provide individual elements adaptable to such a robot. Such elements can also have utility in the manual performance of combinatorial or other chemical synthesis protocols. In particular, such elements include reaction vessels and arrays of reaction vessels together with appropriate closing and sealing means that are preferably built from commercially available and inexpensive components. These reaction vessels and arrays are disposable, where possible, to avoid any cleaning steps. These elements further include tools and work stations directed to the efficient manipulation of such reaction vessels and arrays of reaction vessels, such manipulation including, e.g., sealing and unsealing, fluid dispensing and removal, temperature controlled incubation, and so forth.

Accordingly, in one embodiment, this invention generally comprises an integrated and modular combinatorial chemistry synthesis robot, which is based on reaction vessels disposed in standard sized arrays or modules together with their novel closing and sealing means. These reaction vessel arrays are manipulated by programmable, multipurpose robot arms capable of accepting interchangeable tooling, and are processed at specialized work stations. These components are contained in an enclosure providing a work surface and storage volumes. In various particular embodiments, this invention comprises combinations of one or more of the following elements: reaction vessels and reaction vessel arrays; sealing means for reaction vessels and arrays; one or more robot arms; interchangeable synthesis tools adaptable to the robot arms; specialized synthesis work stations for processing the reaction vessels and reaction vessel arrays; and an enclosure.

In more detail, the reaction vessels of this invention are preferably grouped into arrays or modules of reaction vessels having standard sized form factors and arrangements. Standard sized form factors and arrangements permit standardized design and interchangeability of work stations and tools for processing the reaction vessel arrays. Preferable reaction vessels are inexpensive commercially available vessels, microtitre plates, and so forth, capable of resisting the solvents and reaction conditions used in synthesis protocols. Reaction vessel arrays are sealed with various sealing means. One sealing means comprises caps with valves, which are arranged in arrays of caps of rectangular or other convenient arrangement. The valves are actuated by sliding or rotating rod seals or by having a compressible neck and are capable of being opened and closed simultaneously. Another sealing means comprises caps with apertures which are occluded and sealed by solvent resistant balls made from, e.g., Teflon™. Teflon™ is used generally herein to specify ethylene tetrafluoro-polymers and their compositions or any plastics of equivalent chemical and physical properties. In one preferred embodiment, the balls are attached to a compliant assembly, each sealing ball being capable of tolerating misalignment of a reaction vessel in an array of reaction vessels. In another alternative preferred embodiment, individual reaction vessels sealed with individual sealing balls can be stacked and retained in a cylindrical array for incubation at higher temperatures and internal pressures. Alternatively, arrays of reaction vessels can be sealed either by an inflatable bag or by conventional rubberized septa. Optionally, enhanced septum assemblies are provided with a collapsible, rubber collar with a central orifice, which is collapsed and sealed by a screw cap.

An enclosure according to this invention includes a work surface for supporting specialized work stations disposed above, on, or below the work surface. Below the work surface, preferably, are work stations for temperature controlled incubation of sealed reaction vessel arrays together with facilities for shaking or agitating these arrays during incubation. Also below the work surface, preferably, are storage volumes for storing containers of building block solutions, reagents, and solvents necessary for the various synthesis protocols. Below surface work stations include elevator means for raising reaction vessel arrays, work stations, and storage volumes above the work surface for access by the robot arms. Disposed on or above the work surface are specialized work stations for filling, emptying, sealing, and shaking reaction vessel arrays. These above surface work stations are advantageously directly accessible by the robot arms. Reaction vessel arrays rest on the work surface during and between their processing steps. The enclosure also optionally includes internal sub-enclosures, which are individually capable of maintaining reaction vessel arrays in an inert atmosphere during filling, emptying, and sealing steps.

Robot arms adaptable to this invention perform the manipulations needed to achieve high throughput combinatorial synthesis. Preferably, they are capable of accurate three-dimensional positioning in the enclosure above the work surface. Instead of being dedicated to particular tasks, they are capable of attaching and controlling specialized and interchangeable tooling. One important type of manipulation performed by a robot arm gripper tool is the gripping and the moving individual reaction vessels or reaction vessel arrays from work station to work station.

The specialized work stations of this invention perform tasks needed by the protocols being implemented by a particular robot. In alternative embodiments, certain tasks are performed by specialized tools attached to the robot arms. Work stations needing frequent attention by the robot arms are preferably disposed above the work surface, whereas work stations not requiring frequent attention by the robot arms are preferably disposed below the work surface. Accordingly, time and temperature controlled incubation, needed during the building block addition steps of certain protocols, is performed below the work surface. Reaction vessel arrays are placed on elevators by the robot arms, which then descend below the surface for temperature controlled incubation and later rise back above the surface for access by the robot arms in order to perform subsequent processing. Similarly, storage is preferably below the work surface. Items are stored in holders or containers with standard sized footprints to enable manipulation by standardized tools or stations. It is preferable that below work surface storage be provided for at least approximately 600 storage vessels, e.g., containers such as syringes, or other storage vessels, with individual building blocks solutions. In the case of protocol reagents, it is preferable that below surface storage be available for at least approximately 10 bottles of such reagents. Access to these storage bottles can be provided by tubing which connects with above work surface workstation or other tools. Optionally, fresh reaction vessels and reaction vessel arrays are stored below the surface.

Above work surface work stations include those for reaction vessel sealing, for fluid aspiration, for wash solvent distribution and optionally, for fluid dispensing. Work stations for reaction vessel sealing are adapted to the various novel sealing means of this invention. Stations for ball-based sealing include: those for individually placing sealing balls on the apertures of individual reaction vessels and stacking the sealed reaction vessels into cylindrical arrays, hereinafter called "hot rods;" those for distributing individual balls on an array of reaction vessels; and those for placing compliant ball assemblies on arrays of reaction vessels. Optionally, hot rods have clips for temporarily retaining reaction vessels and sealing balls during assembly and further clips for permanently retaining these components during processing. Stations for arrays of valved reaction vessels include those for manipulating the valve rod seals for simultaneous opening or closing all the valves of the reaction vessels in the array.

Stations for fluid aspiration are based on aspiration through needles, either surface aspiration through flat-ended needles or volume aspiration through fritted needles of this invention. Such stations have multiple needles advantageously arranged in various arrangements, for example linear or rectangular arrays, in order to aspirate simultaneously from part or all of the reaction vessels in one reaction vessel array. Stations for wash solvent distribution, where volumetric accuracy is less important, are adapted to more rapid and repetitive fluid distribution. Such stations preferably also have a two-dimensional array of dispensing tips, which conform to the arrangement of reaction vessels, so that wash solvents can be simultaneously dispensed into all the reaction vessels of an array. Solvent distribution can be powered by inert gas or fluid pressure, and fluid aspiration by vacuum suction.

Alternatively, this invention includes reaction vessel arrays which are arrays of syringes, each syringe including a microporous frit for retaining a solid-phase synthesis support while permitting free passage of fluids. Such syringe arrays can be constructed either from a block of solvent resistant plastic having an array of cylindrical cavities forming the syringe bodies or from independent, commercially-available syringes held in an array by a support means. However constructed, fluid manipulation and distribution can be provided by a network of passageways, each such passageway connecting to one syringe body and externally terminated either by a needle or by a septum. Such fluid passageways can be advantageously placed in a fluid distribution block. In the case of needle termination, the array of needles can be inserted in an array of fluid reservoirs for dispensing fluids to or removing fluids from the syringe bodies. In the case of septum termination, for fluid dispensing to the individual syringe bodies, the septums can be penetrated by needles containing required fluids. Additionally, dispensing to or removing from all the syringe bodies simultaneously can be by means of a common internal passageway interconnecting the syringe bodies to a single external fluid port, which in turn can be coupled through a further tubing network to various fluid reservoirs. Further, plunger means are advantageously provided for simultaneously and accurately manipulating, inwardly or outwardly, all the syringe plungers in such an array to assist in fluid distribution.

Interchangeable tools according to this invention are adapted to be manipulated by the robot arms. Importantly, a robot arm is capable of dynamically attaching and controlling different tools, and is, therefore, not restricted to a particular task during synthesis. These tools include a common attachment base, which permits the robot arm to attach the tool and have access to the controls of the tool, such as by providing communicating between pneumatic ports or electrical contacts in the tool and the robot arm, respectively. These tools are typically used for accurate fluid dispensing, such as dispensing building block solutions or reagents, and for gripping, such as for gripping reaction vessel arrays or compliant ball assemblies. Fluid dispensing tools are preferably constructed with one or more dispensing tips through which accurate aliquots of a fluid are ejected. In the case of building block solutions, where each reaction vessel typically receives a unique building block solution in a particular addition step, fluid dispensing is preferably done with a single tipped tool. Such a tool can simply be a syringe gripper for holding a syringe containing a building block solution and for accurately manipulating of the syringe plunger. In the case of reagents, which are typically common to those reaction vessels in which synthesis is being performed according to a single protocol, it is preferable to use a multiple tipped tool for dispensing reagents simultaneously into all such reaction vessels. These latter tools include a fluid storage vessel, a fluid pump, and piping interconnecting the storage vessel, the pump, and the multiple tips. These tools can also be used to dispense solid-phase beads, in which case the reagent is replaced with a slurry of the beads.

Gripper tools are adapted to move reaction vessels, reaction vessel arrays, and sealing means for reaction vessel arrays. An important gripper is an off-set "U"-shaped gripper, which is adapted both to grip and move reaction vessel arrays and to place or remove certain sealing means of this invention. Another important gripper is a the previously mentioned gripper for distributing building blocks solution. Other grippers can be adapted to grip and move other specialized elements of the reaction vessel arrays and sealing means.

A further type of tool dispenses slurries, and can be used for initially distributing a solid-phase substrate to reaction vessels as well as for mixing and partitioning contents of reaction vessels in order to perform split-synthesis according to various protocols. Such a tool includes a vertical container with a dependent needle and a source of suction. The source of suction draws air through a slurry in the vertical container in order to maintain the slurry in suspension, and can also draw a slurry from a reaction vessel into the container. A controlled source of air volumes can be used to accurately dispense aliquots of the slurry in the vertical container, when the suction is interrupted by a valve. Optionally, in the case of slurries which must be maintained in an inert atmosphere, the dependent needle can be enclosed in a further coaxial tube which provides an inert gas to be drawn into the vertical container through the dependent needle by the source of suction, and the controlled source of air can be replaced by a controlled source of inert gas volumes.

In further embodiments, this invention comprises other combination and sub-combinations of the previously described elements, functioning either in conjunction with other robot apparatus or independently of any robot apparatus. For example, the reaction vessel arrays with their associated sealing means, the fluid aspiration work stations, the fluid dispensing work stations, and certain tools have utility in facilitating semi-automated or manual performance of combinatorial chemistry synthetic protocols. Therefore, each of these elements is independently part of this invention.

4. BRIEF DESCRIPTION OF THE DRAWINGS

These and other features, aspects, and advantages of the present invention will become better understood by reference to the accompanying drawings, following description, and appended claims, where:

FIG. 1 illustrates an embodiment of the synthesis robot of this invention;

FIGS. 2A–B illustrate a ball-sealed, stackable reaction vessel and an associated cylindrical reaction vessel array of the embodiment of FIG. 1;

FIG. 3 illustrates a method of processing the cylindrical reaction vessel arrays of FIGS. 2A–B;

FIGS. 4A–C illustrate a microtitre-style reaction vessel array and a sealing means comprising independent balls;

FIGS. 5A–C illustrate a deep-well microtitre-style reaction vessel array and an inflatable bag sealing means;

FIGS. 6A–D illustrate an array of independent reaction vessels and sealing means comprising a compliant array of balls;

FIG. 7 illustrates a sealing means comprising valved caps for independent reaction vessels;

FIGS. 8A–B illustrate an array of independent reaction vessels with the sealing means of FIG. 7;

FIG. 9 illustrates a work station for manipulating the reaction vessel array of FIG. 7;

FIGS. 10A–B illustrate a sealing means comprising caps with compressible necks;

FIGS. 11A–B illustrate a sealing means comprising punctureable septums;

FIGS. 12A–B illustrate a sealing means of this invention comprising assemblies including punctureable septums;

Figure 2A:
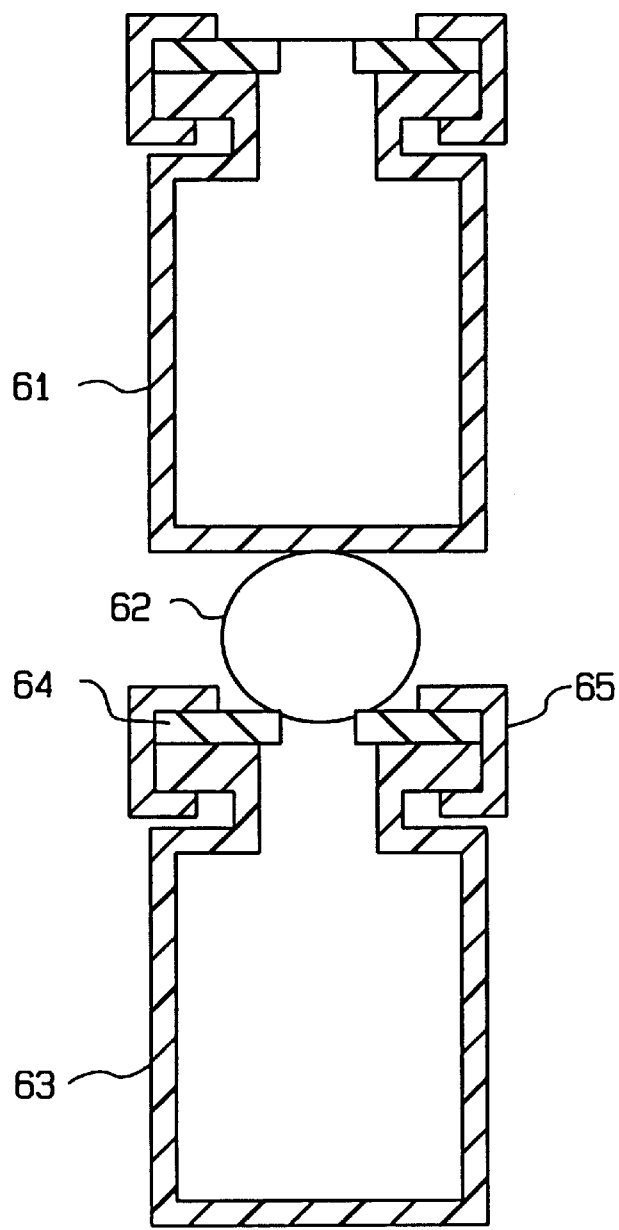
Figure 2B:
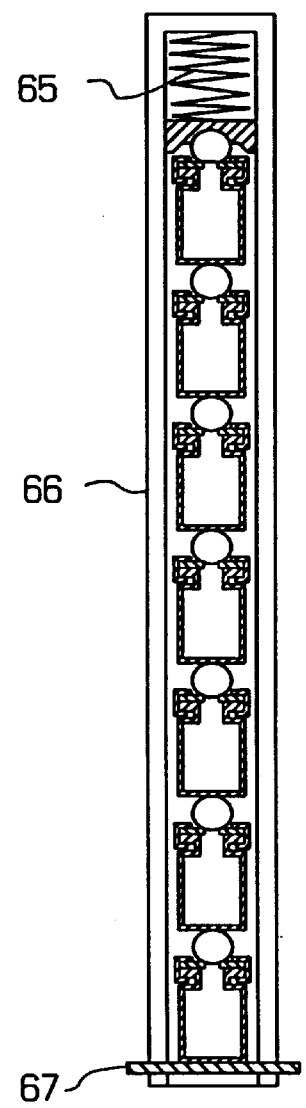
Figures 16A, 16B:
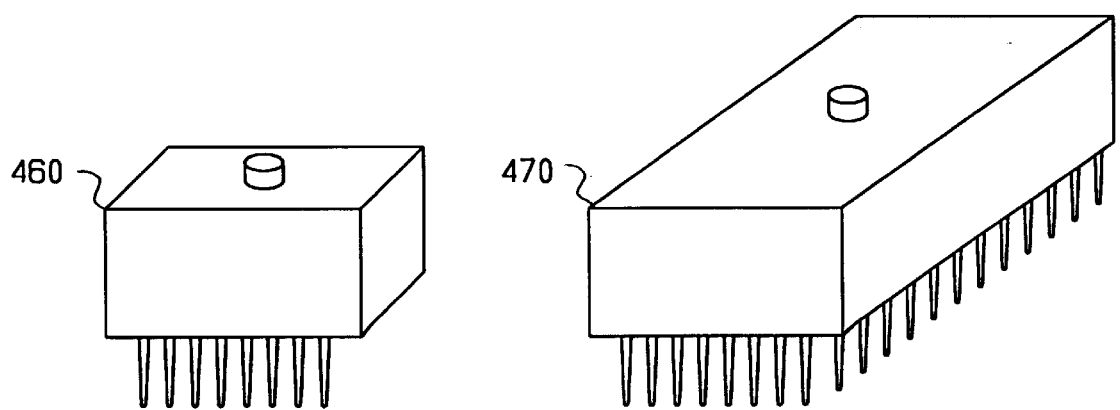
Figure 17:
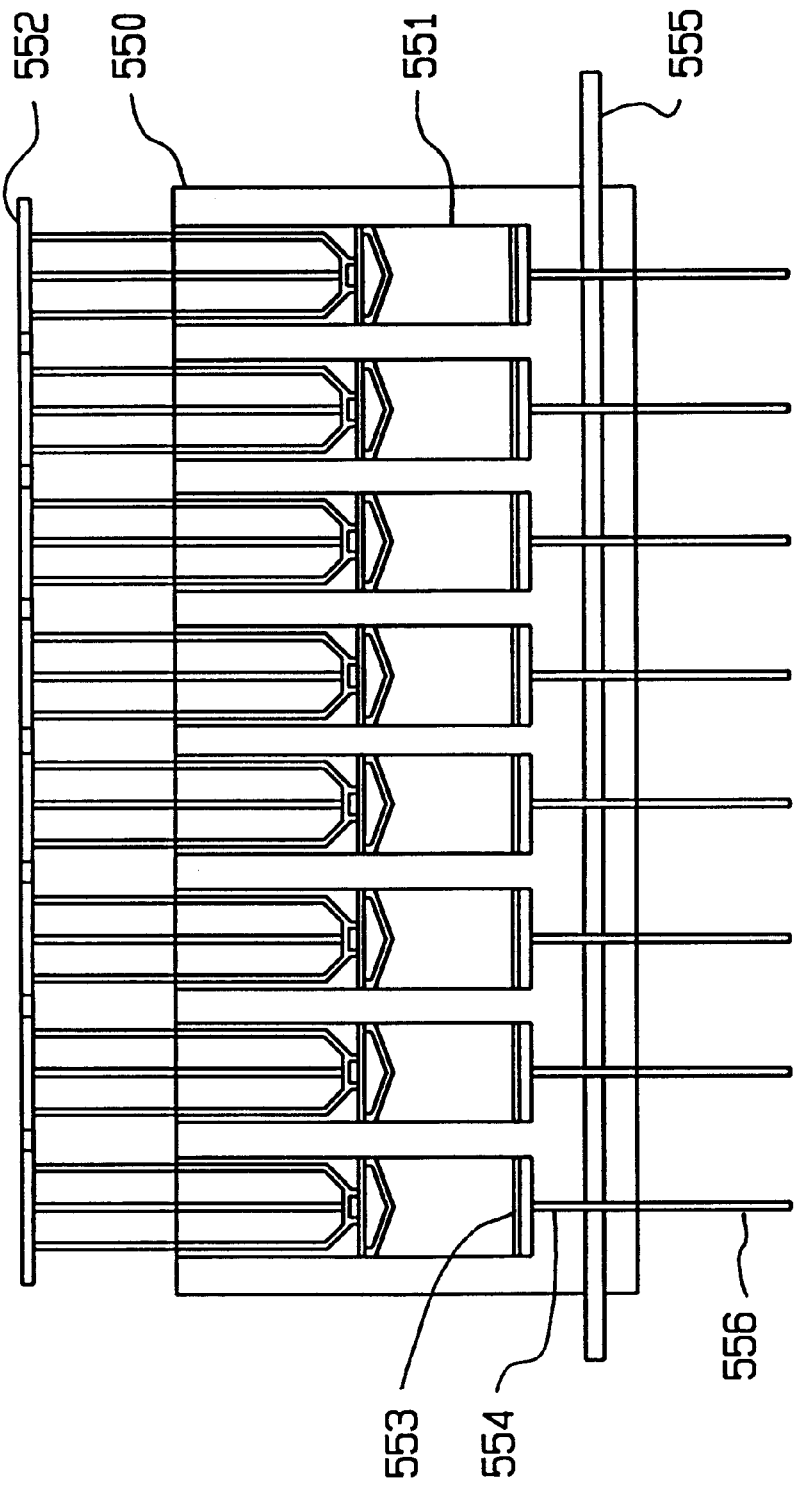
Figure 18A:
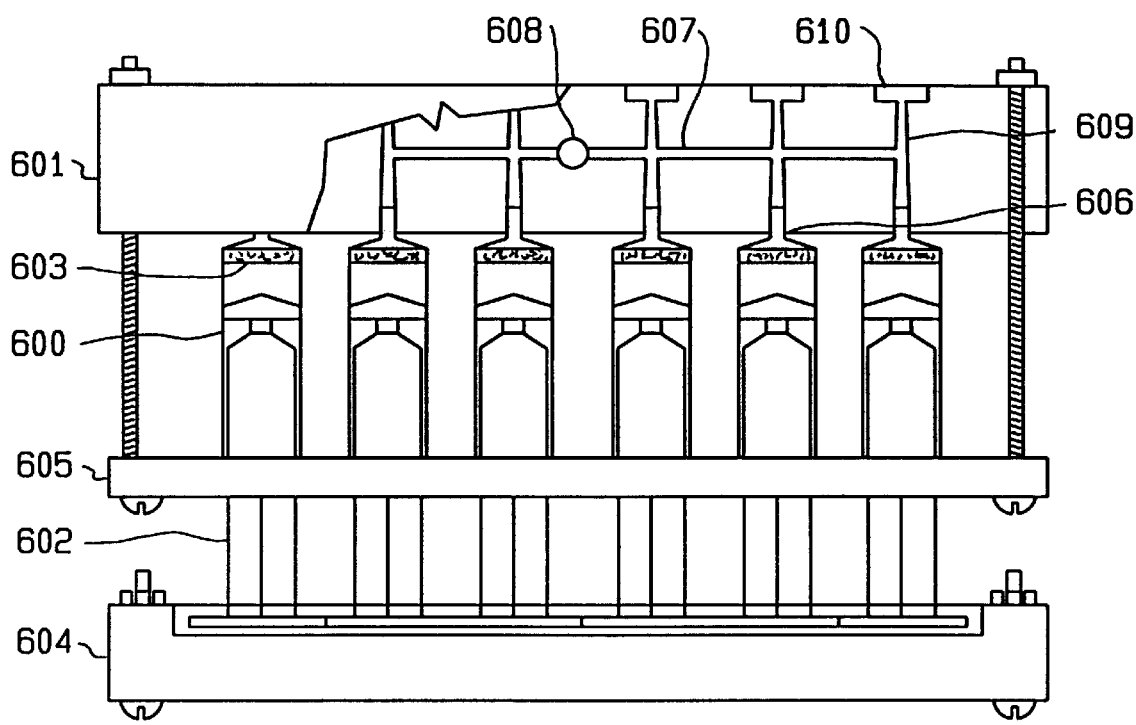
Figure 18B:
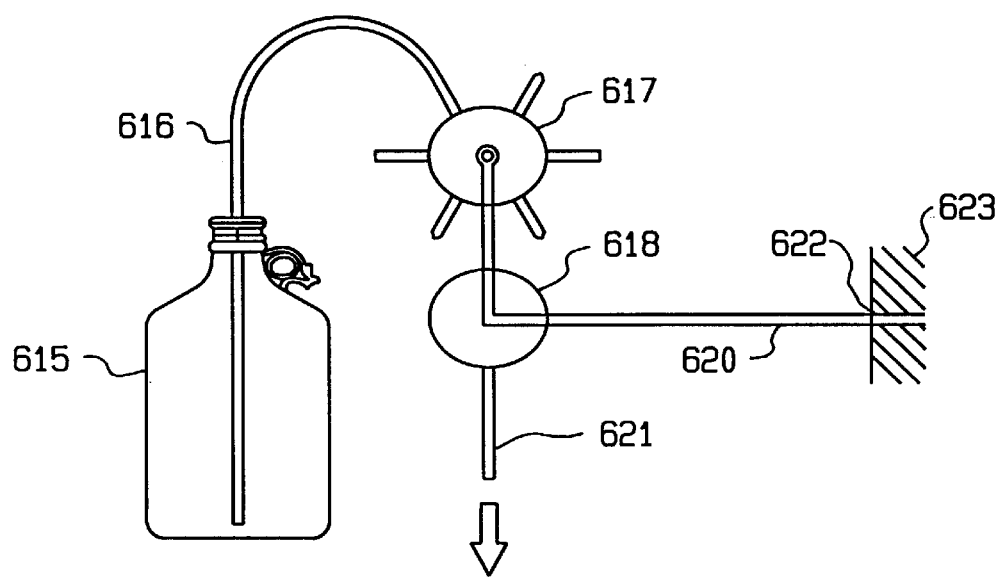
Figure 20A:
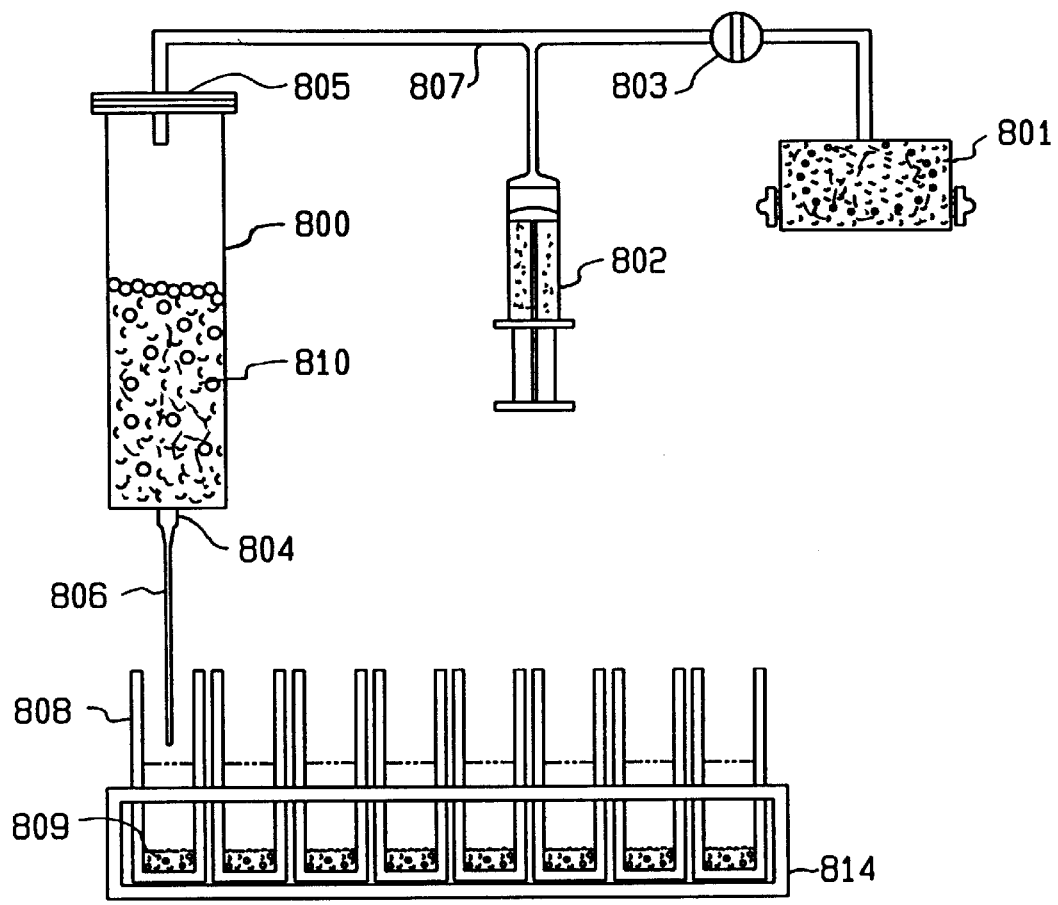
Figure 20B:
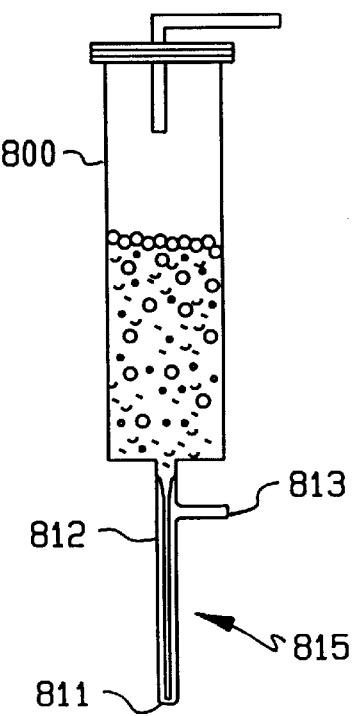

FIGS. 16A–B illustrate tools for fluid dispensing;

FIG. 17 illustrates a syringe reaction vessel array;

FIGS. 18A–B illustrate an alternative syringe reaction vessel array;

FIGS. 19A–C illustrate further details of the ball-sealed, stackable reaction vessels of FIGS. 2A–C; and FIGS. 20A–B illustrate tools for aspirating and dispensing slurries.

5. DETAILED DESCRIPTION

For clarity of disclosure, and not by way of limitation, the detailed description of this invention is presented herein with respect to figures that illustrate preferred embodiments of elements of this invention. However, this invention includes those alternative embodiments of these elements performing similar functions in similar manners that will be apparent to one skilled in the art from the disclosure provided. Additionally, this invention is disclosed with respect to its preferred application to solid-phase, combinatorial chemistry synthesis. The invention is not so limited, and includes application of the various elements disclosed to other chemical protocols having similar functional steps, as also will be apparent to one skilled in the art. For example, components of this invention can be applied to appropriate liquid-phase, combinatorial chemistry synthesis protocols, to other solid- or liquid-phase chemical protocols, or to any combination thereof.

By way of introduction combinatorial chemistry synthesis protocols prescribe the stepwise, sequential addition of building blocks to intermediate partially-synthesized intermediate compounds in order to synthesize a final compound. These protocols are, generally, divided into liquid-phase protocols and solid-phase protocols. In liquid-phase protocols, final compounds are synthesized in solution. Partially synthesized, intermediate compounds are separated from spent reagents between building block addition steps by known means, such as precipitation, fractionation, and so forth. In solid-phase synthesis, final compounds are synthesized attached to solid-phase supports that permit the use of simple mechanical means to separate intermediate, partially-synthesized intermediate compounds between synthetic steps. Typical solid-phase supports include microbeads, of from 30 microns to perhaps 300 microns in diameter, which are functionalized in order to covalently attach intermediate compounds, and made of, e.g., various glasses, plastics, or resins.

Solid-phase combinatorial synthesis typically proceeds according to the following steps. In a first step, reaction vessels are charged with a solid-phase support, typically a slurry of functionalized microbeads suspended in a solvent. These microbeads are then preconditioned by incubating them in an appropriate solvent, and the first of the plurality of building blocks or a linker moiety is covalently linked to the functionalized beads. Subsequently, a plurality of building block addition steps are performed, all of which involve repetitive execution of the following substeps, and in a sequence chosen to synthesize the desired compound. First, a sufficient quantity of a solution containing the building block moiety selected for addition is accurately added to the reaction vessels so that the building block moiety is present in a molar excess to the intermediate compound. The reaction is triggered and promoted by activating reagents and other reagents and solvents, which are also added to the reaction vessel. The reaction vessel is then incubated at a controlled temperature for a time, typically between 5 minutes and 24 hours, sufficient for the building block addition reaction to go to substantial completion. Optionally, during this incubation, the reaction vessel can be intermittently agitated or stirred. Finally, in a last substep of building block addition, the reaction vessel containing the solid-phase support with attached intermediate compound is prepared for addition of the next building block by removing the spent reaction fluid and thorough washing and reconditioning the solid-phase support. Washing typically involves three to seven cycles of adding and removing a wash solvent. Optionally, during the addition steps, multiple building blocks can be added to one reaction vessel in order to synthesize multiple compounds attached to one solid-phase support, or alternatively, the contents of separate reaction vessels can be combined and partitioned in order that multiple compounds can be synthesized in one reaction vessel with each microbead having only one attached final compound. After the desired number of building block addition steps, the final compound is present in the reaction vessel attached to the solid-phase support. The final compounds can be utilized either directly attached to their synthetic supports, or alternatively, can be cleaved from their supports. In the latter case, the linker moiety attaching the compound to the solid-phase support is cleaved, and the library compound is extracted into a liquid phase.

An exemplary solid-phase combinatorial protocol is that for the synthesis of peptides attached to MBHA resin, which proceeds according to Lam et al., 1991, A new type of synthetic peptide library for identifying ligand-binding activity, *Nature* 354: 82–84. Another exemplary protocol is that for the synthesis of benzodiazepine moieties, which proceeds according to Bunin et al., 1992, A general and expedient method for the solid phase synthesis of 1,4-benzodiazepine derivatives, *J. Amer. Chem. Soc.,* 114: 10997–10998. Exemplary building blocks and reagents are amino acids, other organic acids, aldehydes, alcohols, and so forth, as well as bifunctional compounds, such as those given in Krchnak et al., 1996, Synthetic library techniques: Subjective (biased and generic) thoughts and views, *Molecular Diversity,* 1: 193–216.

In view of the large potential numbers of final compounds in combinatorial libraries, it is advantageous that at least some manipulations needed by the synthetic protocols be assisted or performed automatically. In view of the exemplary protocol described, a flexible, automated, robot for combinatorial chemistry synthesis advantageously includes facilities for handling fluids, for manipulating reaction vessels, and for storage of reagents and building blocks. Advantageous facilities for fluid handling include: facilities to accurately add solutions and slurries, containing, for example, building blocks, solid-phase substrates, reagents or solvents; facilities to rapidly and repetitively add wash solvents; and facilities to rapidly and accurately remove fluid phases from a reaction vessel leaving behind the solid-phase support with attached intermediate compounds. Facilities for manipulating reaction vessels and reaction vessel arrays include: facilities to move reaction vessels and reaction vessel arrays between other processing facilities; facilities for time and temperature controlled incubation of reaction vessels and reaction vessel arrays; and optionally facilities for agitation of reaction vessels during incubation. Each such protocol typically uses many building blocks, perhaps hundreds, a few activating and other reagents, perhaps 2 to 4, and one or two work solvents. Accordingly, there are storage facilities for: a large number of building blocks solutions, typically 300 or more building blocks solutions or more preferably as many as 600 or more building blocks solutions stored, for example, in arrays of syringes; preferably 6 or more preferably 12 or more reagents in larger quantities than for building block solutions; and preferably 3 or more preferably 6 or more of even larger quantities of wash solvents.

Design of the processing resources, reaction vessels and arrays, and other facilities of this invention, advantageously permits simultaneous, parallel processing to occur at all apparatus facilities in order to achieve high synthesis throughput. This is achieved by designs having a few standardized physical sizes and layouts and having a modular nature. Thereby, processing resources can be simultaneously applied to multiple protocols in many reaction vessel arrays and can be sized to achieve required throughput.

Preferred materials for all elements of this invention in contact with the synthetic addition reactions, in particular reaction vessels and their sealing means, must resist the reagents, solvents, and reaction conditions likely to be encountered in the various protocols. In the following detailed description, when solvent resistance is specified and particular materials are not specified, the following exemplary general purpose solvent resistant materials can be used: Teflon™, polypropylene, or glass.

5.1. Integrated Robot Apparatus

Figure 1:
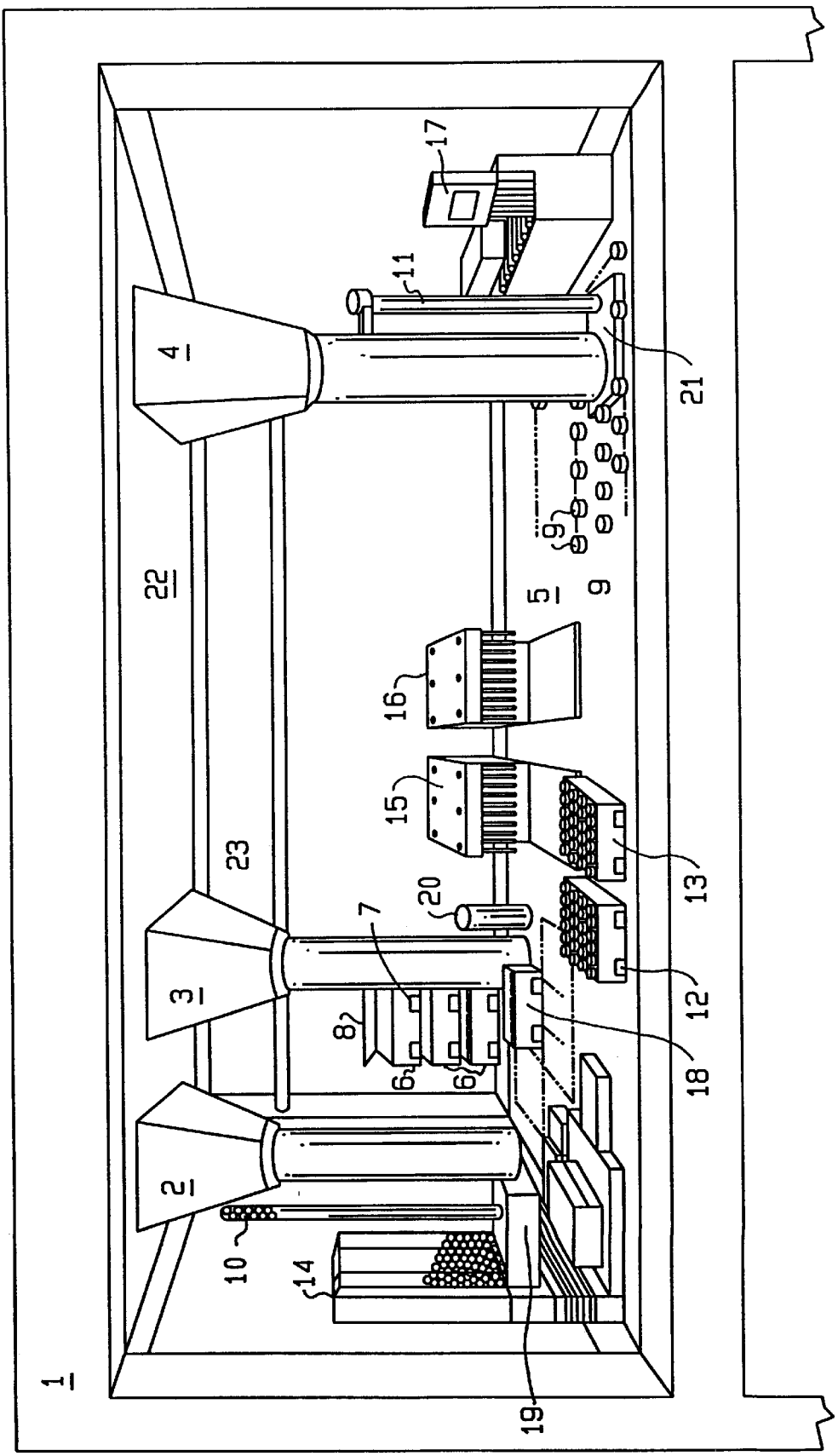

As generally illustrated in FIG. 1, embodiments of the integrated robot apparatus of this invention preferably have processing resources and facilities with a modular design and standardized spatial form factors and spatial layouts or structures. Such modularization and standardization enables high throughput, multi-protocol combinatorial synthesis by permitting interchangeable parallel use of a small number of standardized tools and work stations to process in parallel many inexpensive reaction vessel arrays according to a plurality of protocols. For example, standardizing physical dimensions of reaction vessel arrays permits one, or at most a few, gripper tools to move reaction vessel arrays between work stations. Standardizing the structure or layout of reaction vessel arrays permits a corresponding standardization of the arrays of fluid handling tips in fluid handling work stations. Thereby, one, or at most a few, fluid dispensing and aspirating stations per reaction vessel layout can provide for multiple simultaneous synthetic protocols.

Preferred reaction vessel array form factors and array layouts are determined by what is inexpensive and commercially available. In the following, the terms "form factor" or "footprint" refer to the size and shape of a reaction vessel array, and the term "array layout" refers to the spatial arrangement of reaction vessels in the reaction vessel array. For example, a standard microtiter plate has a rectangular form factor with a typical size of 85×130 mm and a 8×12 rectangular array layout of reaction vessel wells. It is advantageous to adapt embodiments of the robot of this invention to such a common standard rectangular 85×130 mm form factor of microtiter plates. This form factor can accommodate a rectangular 8×12 array layout of 96 reaction wells or reaction vessels, the microtitre plate, as well as a rectangular 4×6 array layout of independent reaction vessels. A rectangular array of 24 reaction vessels in a microtitre form factor is particularly adapted to commercially available 4 ml reaction vessels. It will be apparent to one of skill in the art, that this invention can be adapted to other physical array dimensions and array structures by either scaling or rearranging the elements disclosed. Thus the currently preferred microtitre, rectangular standard can be replaced by other standards that may be developed based on squares and rectangles of other sizes with the reaction vessels disposed, perhaps, in other array structures, such as hexagonal arrays. Alternative standardizations, merely requires changes in fluid handling tip arrays, work station sizes, and gripper tools. The principles of the high throughput, integrated robot of the invention remain applicable.

The reaction vessels of this invention are preferably sealed during certain synthetic steps, in particular during temperature controlled incubation and during agitation. This invention contemplates various sealing means. Certain sealing means seal a rectangular array of reaction vessels; other sealing means, adapted to higher incubation temperatures and pressures, require packing reaction vessels into cylindrical arrays.

FIG. 1 generally illustrates one embodiment of an integrated, synthetic robot according to this invention that incorporates the previously recited facilities advantageous for high throughput, multi-protocol combinatorial synthesis. This embodiment is adapted to a reaction vessel embodiment in which reaction vessels during processing are alternately packed into cylindrical modules, such as module 10, or disposed in rectangular arrays, such as array 12. The illustrated embodiment generally includes enclosure 1, robot arms 2, 3 and 4, work surface 5, and various work stations and robot arm tools. Enclosure 1 provides mechanical support for work surface 5 and robot arms 2, 3, and 4. The enclosure illustrated in FIG. 1 has the preferred dimensions of 150×100×50 cm. In general, it can be chosen to be of a width and depth sufficient support a sufficient number of work stations, tools, and reaction vessel arrays to achieve the desired level of synthetic throughput.

One or more general purpose robot arms are present in an embodiment of this invention in order to manipulate reaction vessel arrays and tools. They are, preferably, capable of full, independent, and unimpeded access to all reaction vessels arrays, tools, and work stations disposed above work surface 5. The number of robot arms is chosen to provide sufficient parallel handling capabilities to maintain the available workstations busy in order to achieve the desired throughput. Preferably, the robot arms are capable of attaching and actuating interchangeable tools, including tools for gripping reaction vessels, reaction vessel arrays, or sealing means and tools for accurately dispensing fluids into reaction vessels. Such tools can be actuated by, e.g., electric or pneumatic connections between the arm and the tool. In FIG. 1, robot arms 2, 3, 4 are positioned by means of a two-dimensional linear stepper motors formed by pole arrays disposed in upper surface 22 of enclosure 1 and the base of the robot arms, such as base 23. This invention is adaptable to other arm positioning technologies known in the art, such as jointed arms actuated by pneumatic or hydraulic actuators. See, e.g., Rehg, 1997, *Introduction to Robotics in CIM Systems*, Prentice-Hall, Inc., Upper Saddle River, N.J.

In particular, this invention is adaptable to laboratory robots from, e.g., Yaskawa, Inc. (Cypress, Calif.), CRS, Inc. (Burlington, Ontario, Canada), Zymark, Inc. (Hopkington, Mass.), or Sagian, Inc. (Indianapolis, Ind.).

This embodiment includes work stations, reaction vessels, and reaction vessel arrays both above and below work surface 5. Facilities needing more frequent attention by the robot arms, such as fluid manipulation facilities, are preferably disposed above work surface 5, while facilities needing less frequent attention, such as storage facilities and incubation means, are preferably disposed below work surface 5. This invention is adaptable to other distribution of processing resources above and below the work surface. An exemplary below-surface storage means, illustrated in FIG. 1, is elevator 8, lifting storage shelves 6, supporting holders 7, which have a standardized footprint and contain arrays of containers, e.g., syringes, with building block solutions, vessels of reagents, bottles of solvents, fresh reaction vessels, and so forth. Holder 18, having arrays of containers with building block solutions, has been placed on work surface 5 by a robot arm using a gripper tool for subsequent access by robot arm 3, which is in the process of distributing various building block solutions to the reaction vessels in array 12. Elevator 8, illustrated in a raised position for robot arms access, can be lowered so that its top surface is flush with work surface 5, forming an additional area of work surface and not impeding robot arm motion. Raising and lowering means adaptable to such elevators are known in the art and, optionally, include mechanical, hydraulic, pneumatic or electric means. For example, in FIG. 1, the elevator is actuated by a servomotor and a rack and pinion drive. Further below work surface stations are temperature controlled incubators, in which reaction vessels arrays are placed for reactions at a controlled temperature. A temperature range, preferably from −50 to +150° C., is created by circulating fluids, preferably air, into direct contact with the reaction vessel arrays.

For rectangular reaction vessel arrays, such as arrays 12 or 13, such incubators can be accessible by an elevator similar to elevator 8. For cylindrical reaction vessel arrays, such as arrays 10 or 11, such incubators can be accessed through surface ports, such as ports 9. Cylindrical arrays can be placed in such ports by specialized robot gripper tools. Further, these incubation means optionally and preferably include means to agitate the reaction vessels during incubation.

FIG. 1 also illustrates certain above work surface elements, such as reaction vessels, reaction vessel arrays, specialized work stations, and arm tools. Preferably, reaction vessel arrays have standardized spatial footprints or spatial forms (herein also called "form factors"), such as the rectangular footprints of arrays 12 or 13 or the cylindrical footprint of arrays 10 or 11. Individual work stations performing specialized functions are then adapted to reaction vessel arrays with those standardized footprints, and thereby can perform their specialized functions on all arrays of that footprint, whatever the details of their manufacture and independent of the particular synthesis protocol being performed. Work stations adapted to cylindrical modules include assembly/disassembly station 14, which either assembles cylindrical arrays for incubation from individual reaction vessels stored in rectangular arrays or disassembles reaction vessels from cylindrical arrays into rectangular arrays for fluid manipulation. Below surface incubators having access ports 9 are also adapted to cylindrical arrays. Stations adapted to rectangular form factors include wash-solvent dispensing work station 15, fluid aspiration work station 16, and incubators accessible by elevators similar to elevator 8. For example, rectangular reaction vessel array 13 can be washed by having robot arm 2 position array 13 in fluid dispensing station 15 for dispensing of a wash-solvent and then having robot arm 2 position array 13 in fluid aspiration station 16 for aspiration of the wash solvent. A plurality of these manipulations implements a plurality of washing steps. Alternatively, one fluid handling work station can be adapted to both dispense and aspirate work solvents.

Not illustrated in FIG. 1 are sub-enclosures capable of retaining an inert atmosphere. These sub-enclosures are preferably of rectangular shape, having glass or plastic surfaces, with an optional lid, and contain those work stations that must manipulate unsealed reaction vessels, such as fluid manipulation work stations. These sub-enclosures are charged with a heavier than air inert gas, such as argon, and are thereby capable of maintaining unsealed reaction vessels in an inert atmosphere, while permitting access by robot arms.

General purpose robot arms 2, 3, and 4 attach interchangeable tools in order to perform specialized functions, including gripping and fluid manipulation. For example, gripper 19 attached to arm 2 is specialized, for among other tasks, gripping and moving reaction vessel arrays having a standardized rectangular form factor. Using gripper 19, robot arm 2 moves rectangular reaction vessel arrays between the fluid dispensing work station, the fluid aspiration work station, and the cylindrical array assembly/disassembly work station (see infra.). On the other hand, gripper 21 is adapted to securely grip long cylindrical reaction vessel arrays, such as array 11, and to raise and lower them into below work surface incubators through ports 9. Syringe tool 20 is a fluid manipulation tool which grips individual syringes and accurately manipulates the syringe plunger to dispense controlled aliquots of a contained fluid. Here syringe tool 20 attached to arm 3 has removed a syringe containing a building block solution from storage array 18, and is dispensing controlled aliquots of the building block solution into the reaction vessels in reaction vessel array 12.

Robot arm means refer to any robot arms having specification suitable to perform the above-mentioned manipulations. In particular, the embodiment of FIG. 1 can be constructed from commercially available robot arm means and enclosures. Exemplary robot arm means are manufactured by Yaskawa, Inc., as models platform RW 161 using XY motor RM 6210. The work surface itself and below work surface work stations are manufactured by SAIC, Inc. Further, the embodiment of FIG. 1 advantageously utilizes commercially available control hardware and software. (See infra.) Such hardware and software is also supplied by SAIC, Inc.

5.2. Reaction Vessel Embodiments

The following subsections disclose particular embodiments of reaction vessels, reaction vessel arrays, corresponding sealing means, and suitable specialized tools and work stations for processing these arrays. These embodiments include in the sequence described: arrays of reaction vessels sealed by balls and stacked in cylindrical arrays; microtitre plates of 96, 384, or more wells and other similar modules; rectangular arrays of 24 independent vessels in a microtitre form factor and sealed by ball assemblies or by valves; reaction vessels sealed by various types of punctureable septums. The last subsection describes the novel use of arrays of standard, commercially available syringes as reaction vessels.

In the following, container means refers generally to any of these reaction vessel embodiments, which are capable of containing reaction mixtures for combinatorial chemistry. Further, sealing means generally refers to those methods for sealing appropriate to each of these embodiments of container means, or reaction vessels.

5.2.1. Ball-Sealed, Stackable Reaction Vessels

Figure 3:
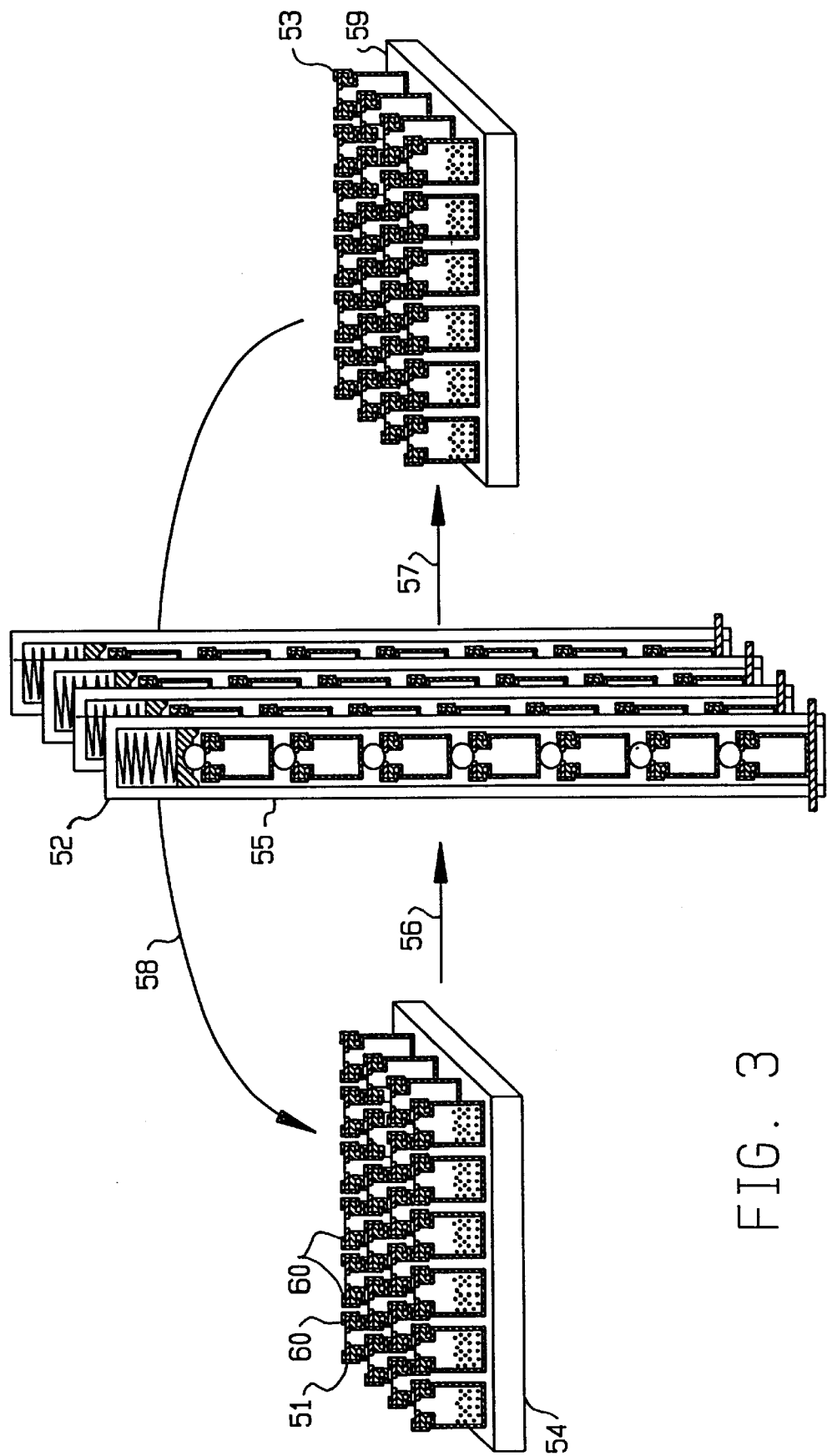

FIGS. 2, 3, and 19 illustrate generally a preferred structure for stackable, ball-sealed reaction vessels and a method of processing such reaction vessels. This embodiment is preferred for protocols requiring higher incubation temperatures, which generate higher internal pressures in the reaction vessels. Cylindrical module 55 of FIG. 3, also known as a "hot rod," is particularly adapted to sealing reaction vessels against greater internal pressures, because it is able to generate greater forces on the sealing balls.

Turning first to a method of processing such reaction vessels as illustrated in FIG. 3, in a first processing step at location 51 in the robot apparatus, rectangular reaction vessel array 54 holds a 4×6 array of 24 reaction vessels 60 in an unsealed condition. At this step, accurate aliquots of solutions containing building blocks, activating reagents, and other reagents are dispensed into the reaction vessels. typically, each reaction vessel receives a different building block, while all the reaction vessels in an array receive the same activating and other reagents. Alternatively, different reaction vessels in one array can contain compounds being synthesized according to different protocols, in which case different activating and other reagents would also be individually dispensed into the reaction vessels according to the particular protocol. After all the solutions for a particular synthetic addition step are dispensed into the reaction vessels, reaction vessel array 54 is transported by a robot arm to a hot rod assembly/disassembly station. As represented by step 56, this assembly/disassembly station individually places sealing balls over the apertures of each reaction vessel, and then stacks, e.g., six reaction vessels into one hot rod 55.

At the next processing step at location 52, the hot rods are incubated for a controlled time at a controlled temperature, during which the building block addition reactions proceed substantially to completion. After incubation, step 57 represents the transport of each hot rod to the assembly/disassembly station, which unstacks the reaction vessels from a hot rod into a rectangular reaction vessel array and then removes the sealing balls from the reaction vessel apertures.

At a final processing step at location 53, reaction vessel array 59 is repetitively washed and its solid state resin reconditioned by, e.g., repetitively positioning the array 59 at a solvent dispensing station for dispensing wash solvent into the reaction vessels followed by positioning at a solvent aspiration station for selective removal of only the wash solvent. Finally, processing step 58 represents transport of a reaction vessel array by a robot arm from washing location 53 to fluid dispensing location 51 in order to begin another step of building block addition.

FIGS. 2A–B illustrate in more detail the structure of the reaction vessels and the hot rod of this embodiment. Reaction vessel 63 is, preferably, a commercially available, solvent resistant, 4 ml vessel, having a size of approximately 15 mm outside diameter by 45 mm length. Vessels of such size can be placed in a rectangular 4×6 reaction vessel array having microtitre form factor while leaving separations between the vessels of no less than approximately 5 mm.

These vessels can be charged with approximately 50 mg of solid-phase resin particles to yield approximately 10 mg of a synthesized compound with molecular weight of approximately 1000 Da. These vessels include septum 64, having an aperture for access to the interior of vial 63, and retainer 65. The aperture of septum 64 is capable of being sealed by sealing ball 62 having a diameter preferably at least approximately 1.5 to 5 times that of the size of the aperture in septum 64. Septum 64 is tightly retained to the lip of vial 63 by retainer 65. In a preferred embodiment, retainer 65 is of a metal, such as aluminum; septum 64 is of a solvent resistant elastomer, such as Kalrez™, and ball 62 is a solid ball of a rigid solvent resistant plastic, such as Teflon™. The aperture in septum 64 is approximately from 1 to 4 mm in diameter. In an alternative embodiment, in place of sealing ball 62, the aperture in septum 64 can be sealed by a disk which protrudes above retainer 65 and is capable of sealing the aperture in septum 64. Such a disk can be made of Teflon™. Alternatively, vessels in a hot rod can be sealed by use of compliant balls of a solvent resistant and flexible elastomer, such as Kalrez™ (DuPont, Wilmington, Del.). In this alternative, septum 64 and crimp 65 can be omitted. Kalrez™ is used generally herein to specify any perfluoroelastomer possessing exceptional resistance to degradation by aggressive fluids or gases, or any other elastomers of equivalent chemical and physical properties.

FIG. 2B illustrates in more detail a hot rod of this embodiment. Additional details are illustrated in FIGS. 19A–C. Tube 66 has an inside diameter just sufficient to accommodate the reaction vessels and a length sufficient to accommodate, for example, six reaction vessels along with spring 65 in a sufficiently compressed condition. Tube 66 is preferably made of a metal, such as aluminum. Spring 65 is chosen to compress the stacked reaction vessels with a force sufficient to maintain the sealing balls sealed against the apertures in the reaction vessel septums despite internal vapor pressures generated in the reaction vessels at desired incubation temperatures. The required force is determined by the reagents and the incubation temperature. During reaction processing, metal clip 67 retains the reaction vessels in tube 66 against the force of spring 65 by occluding a sufficient porreaction ve opening of tube 66 to prevent reaction vessels being driven from the tube. During hot rod assembly and disassembly, additional temporary retaining means illustrated in FIG. 19A temporarily retain the reaction vessels and sealing balls before the metal clip 67 is placed in tube 66. As illustrated in FIG. 2B, clip 67 is a metal tongue fitting longitudinally through slots in the sides of tube 66 and being shaped to permit an assembly/disassembly plunger to fit around clip 67. Alternatively, clip 67 can be a circular clip retained by recesses in the outer surface of tube 66 and having a central aperture, or it can be a screw cap having central aperture.

Reaction vessel array 54 of FIG. 3, also known as a transport block, holds the reaction vessels of this embodiment for manipulation steps, including fluid dispensing and aspiration steps and hot rod assembly and disassembly. This transport block is preferably of the same size and structure as the other embodiments of reaction vessel arrays of this invention. In an exemplary embodiment, transport block 54 can have a microtitre form factor of 85×130 mm and hold 24 reaction vessels in a 4×6 rectangular array and can be made of a plastic material.

Accompanying this embodiment of reaction vessels and vessel arrays are certain specialized work stations and tools, including a hot rod assembly/disassembly work station, a specialized incubation work station, and a gripper/agitator tool. The hot rod assembly/disassembly station is generally illustrated as work station 14 of FIG. 1 and in more detail in FIGS. 19B–C. This station takes advantage of further hot rod elements illustrated in FIG. 19A.

FIG. 19A illustrates in detail the retaining means preferably present in the base of hot rod 701. First, metal clip 702, here shown inserted through slots 703 of hot rod 701, is adapted to securely retain reaction vessels with sealing balls during processing of addition reactions. Second, clippers 704 are adapted to temporarily retain reaction vessels during hot rod assembly and disassembly. The clippers are generally rectangular, of metal, and are pivotally mounted on pivot rods 706, which are in turn mounted to the base of hot rod 701. Spring assemblies 707 are adapted to urge clippers 706 so that their upper segments project into the lumen of the hot rod to a limited inward inclination, while permitting pivoting about mounting rod 706 outwardly through slots 705 in the side of hot rod 701. Thereby, when a reaction vessel or a sealing ball is inserted into hot rod 701 through base 708, clippers 704 pivot to freely admit the reaction vessel or sealing ball and then incline inwardly after the passage to retain the contents of hot rod 701. Further, pressure on the outwardly inclined lower segments of clippers 704 pivots them to permit the contents of hot rod 701 to drop through base 708.

FIG. 19B illustrates details of a workstation adapted to the assembly of clipper-equipped hot rods and its method of operation. This workstation includes reservoir 720 for holding sealing balls and lifting mechanisms 722 and 724 actuated by, e.g., electric or pneumatic means. Assembly of reaction vessels into vertical rod 726 includes the following two steps: a first step in which a sealing ball is placed into hot rod 726, and a second step in which a reaction vessel is placed in the hot rod. The first step begins when a gripper attached to a robot arm grips a hot rod and places it above upper opening 727 in extension 721 of sealing ball reservoir 720. Lifting mechanism 722 moves handle 723 upwards through lower opening 728 in the reservoir extension. Sealing ball 729 is pushed upward till it passes clippers 730 in hot rod 726. The clipper spring assembly retains the ball by urging clippers 730 into a closed position, i.e., a position that holds reaction vessels and sealing balls inside rod 726 and prevents them from dropping below the clippers. After sealing ball 729 is inserted past clippers 730, handle 723 actuated by lifting mechanism 722 returns through lower opening 728. For the second step, the robot arm moves hot rod 726 above second lifting mechanism 724 actuating handle 725 for reaction vessels. A second robot arm grips and positions array 731 of reaction vessels so that reaction vessel 732 is placed below the hot rod opening. Lifting mechanism 724 moves handle 725 upwards through an opening in array 731 and pushes reaction vessel 732 into rod 726 past clippers 730. The insertion of sealing balls and reaction vessels into hot rod 726 repeats as many times as necessary to fill hot rod 726. Finally, after the hot rod has been fully loaded with reaction vessels and sealing balls, the assembly station places a retaining clip at the base of the hot rod to securely retain the reaction vessels in the hot rod during reaction processing.

FIG. 19C illustrates details of a workstation adapted to the disassembly of clipper-equipped hot rods and its method of operation. In order to disassemble a loaded hot rod and place the contained reaction vessels into a rectangular array of reaction vessels, which was previously placed at this workstation, a robot arm, first, grips a loaded hot rod and removes the retaining clip. Next, the robot arm places hot rod 740 with closed clippers 741 over array or holding block 744, and a mechanical actuator opens the clippers by pressing their protruding lower ends towards the rod axis. Reaction vessel 745 drops from hot rod 740 through open clippers 742 into array 744. The mechanical actuator then releases the clippers, and they again assume closed configuration 743 retaining sealing ball 746 of the just released hot rod. Next, the robot arm moves hot rod 740 over a sealing ball collection station. Sealing ball 746 is released from rod 740 by similarly pressing and releasing the clippers. The sealing ball collection station can optionally, e.g., wash the balls for reuse. This process repeats until the hot rod is empty.

Further special processing resources of this embodiment include an incubation station and a gripper/agitator tool. The incubation station, illustrated generally by ports 9 of FIG. 1, comprises circular ports in the work surface adopted to receive and support hot rods placed for incubation by a robot arm. Below the work surface, the hot rods are exposed to a flow of a temperature controlled fluid, such as heated or chilled air. During incubation, reaction vessels in the hot rods can be agitated by a gripper/agitation tool attached to a robot arm. This tool comprises a gripper adapted to grip the top of the hot rods in the ports of the incubation station and spin them in an off axis manner. Typically, the spinning axis is displaced off-center by a distance of approximately $\frac{1}{8}$ to $\frac{3}{8}$ of the radius of the hot rod.

5.2.2. Microtitre-Style Rraction Vessels

Another embodiment of reaction vessel arrays of this invention comprises various commercially available microtitre-like plates having arrays of wells or vessels. Exemplary of such commercially available plates are standard microtitre plates with an 85×130 mm footprint and having a rectangular array of 96, 384, or more wells. Normal or deep well microtitre plates made of a solvent resistant material can be used in this embodiment. This embodiment is equally adaptable to other similar commercially available plates having arrays of wells or vessels. Reaction vessel arrays of this embodiment are sealed by various sealing means, including free sealing balls, an inflatable bag, a compressible plate, and a compliant ball assembly to be described in a subsequent subsection.

Figure 4A:
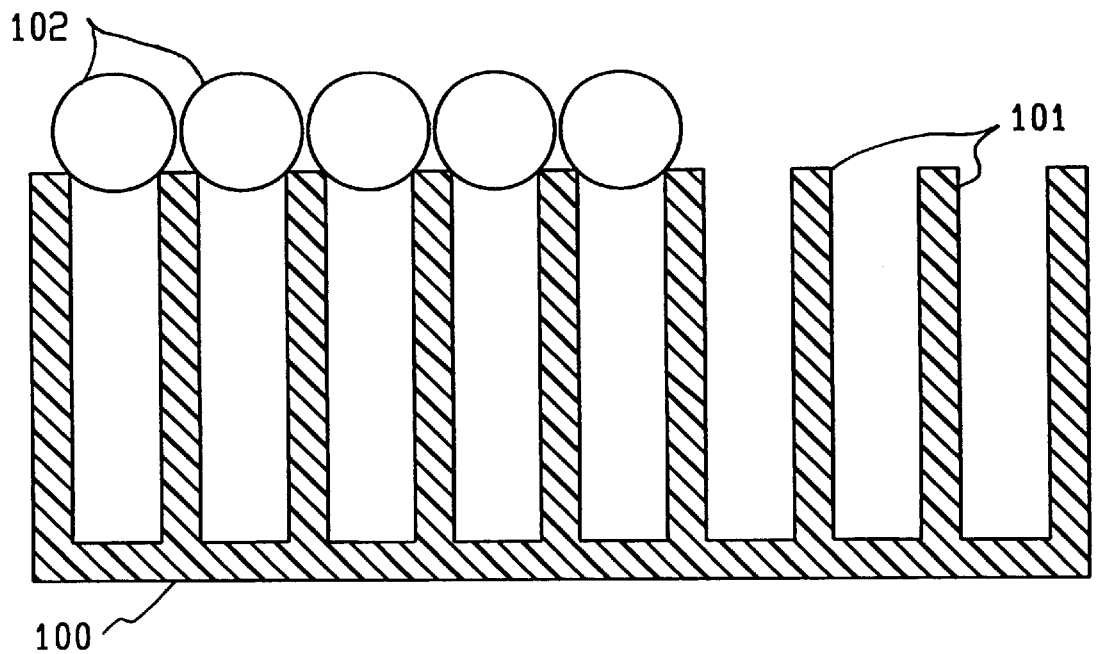
Figure 4B:
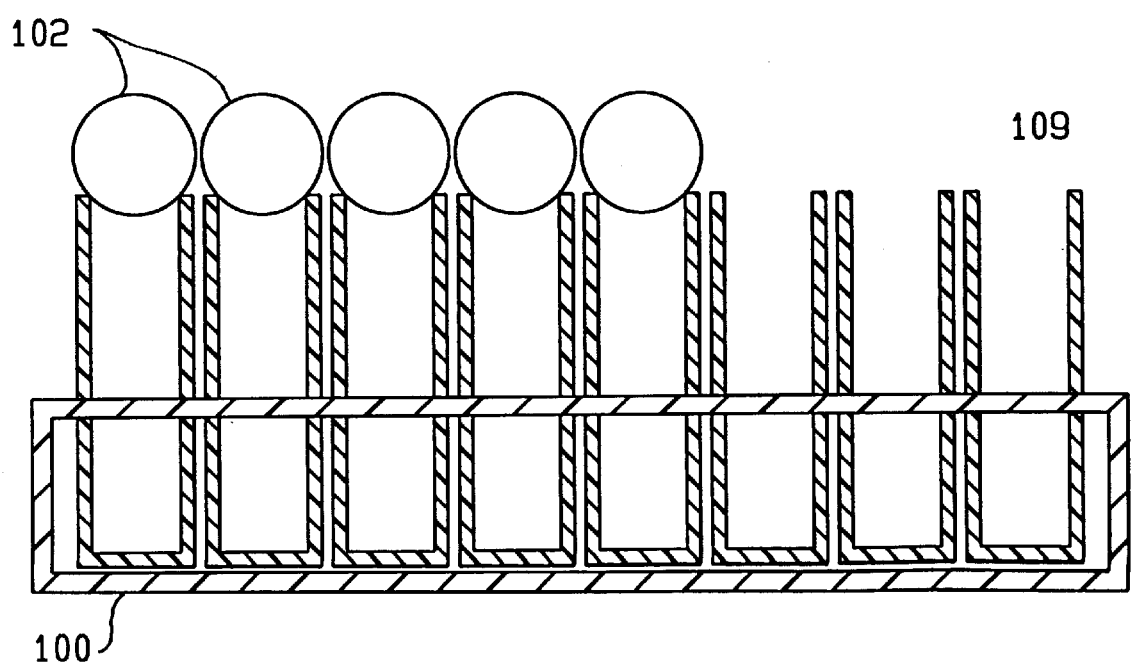
Figure 4C:
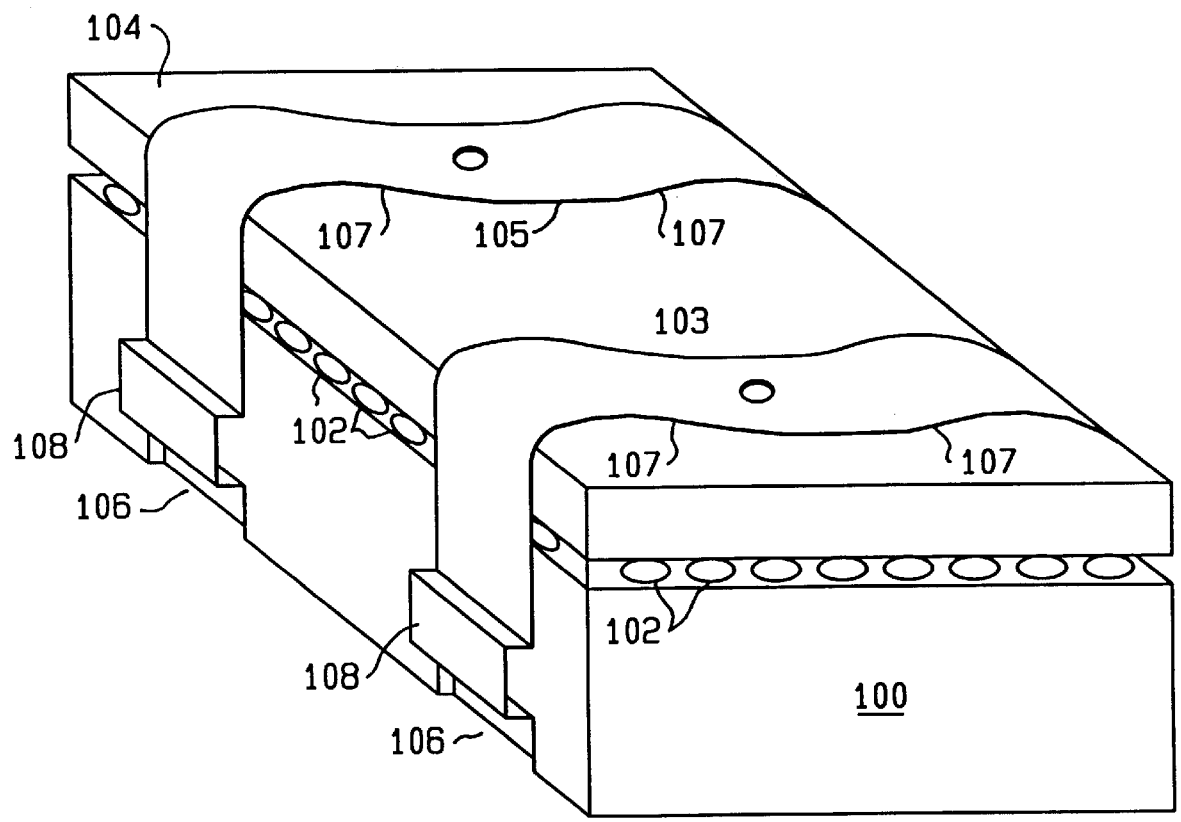

FIGS. 4A–C illustrate exemplary embodiments of a microtitre plate sealed by sealing balls unattached to any support. In FIGS. 4A–B, microtitre plate 100 has reaction vessels, a fraction of which are sealed by unattached sealing balls 102. In more detail, FIG. 4A illustrates microtitre plate 100 having integral wells 101 serving as reaction vessels. A fraction of wells 101 have apertures sealed by unattached sealing balls 102. Upon complete sealing of a plate, all wells in the plate will be sealed by sealing balls. Sealing balls 102 are of a solvent resistant material, such as Teflon™, and are of a size sufficient to seal apertures of wells 101 yet not so large that they mutually contact or interfere when all the wells of microtitre plate 100 are so sealed. FIG. 4B illustrates an alternative embodiment in which plate 100, perhaps a microtitre plate, supports reaction vessels 109, which can be vials or test tubes of a solvent resistant material such as polypropylene. In this embodiment, sealing balls 102 are similarly adapted to seal the aperture of vessels 109.

When unattached sealing balls are used, it is preferable to retain these balls tightly in place during movement of the reaction vessel array by the robot arms and during incubation, perhaps at an elevated temperature. FIG. 4C illustrates an exemplary means for exerting a sealing and retaining force on unattached sealing balls 102, which are sealing the wells of microtitre plate 100. The illustrated retaining means comprises rigid plate 104, which is for example made of a metal such as aluminum or a rigid plastic, and whose face adjacent to the sealing balls is optionally covered with a compressible rubber-like layer made of silicone rubber. Plate 104 is retained against the sealing balls by spring clips 103 and 105, which have arms engaging recesses 106 in microtitre plate 100. Clips 103 and 105 have spring sections 107 for generating sufficient sealing and retaining force. This force should be at least approximately sufficient to resist internal vapor pressure generated during incubation. These clips have sections 108 which can be engaged by a standard gripper on the robot arm to permit placement and removal of the sealing means. These clips are similar to clips 113 of FIG. 5A–C.

Figure 5A:
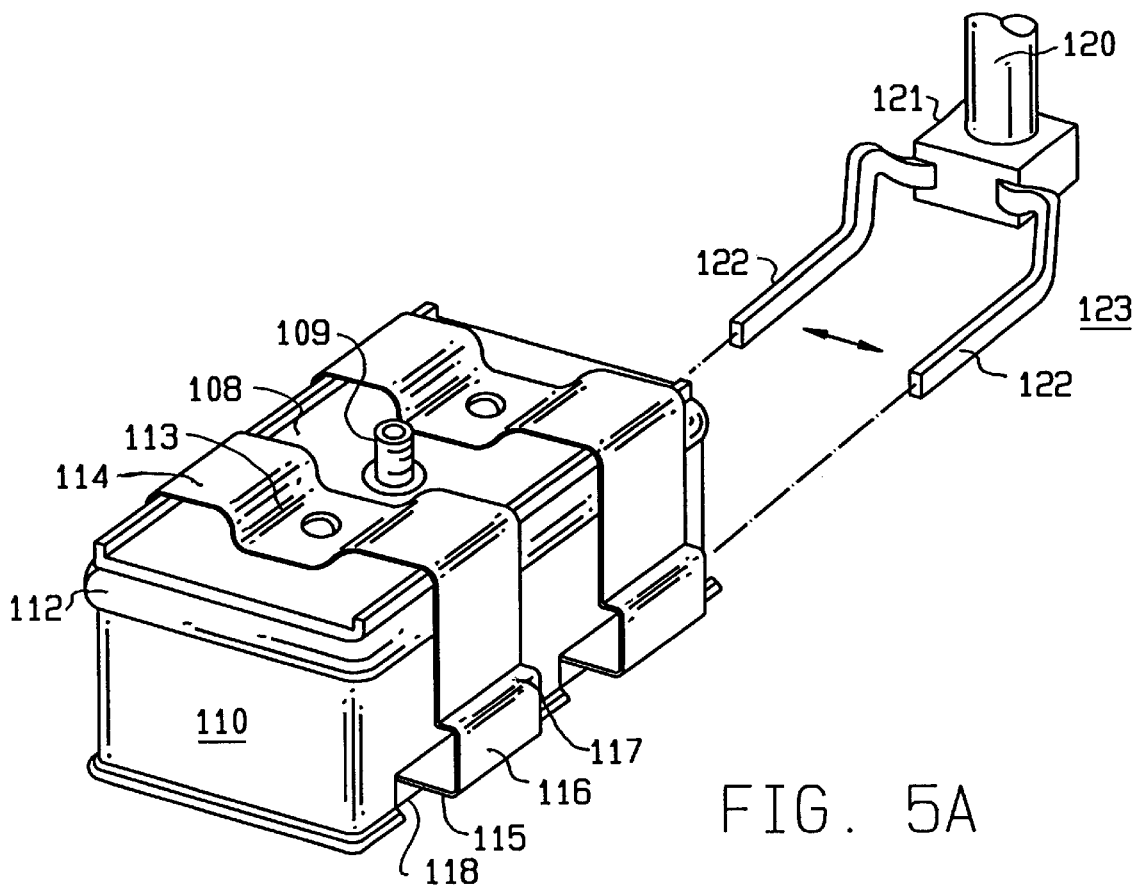
Figure 5B:
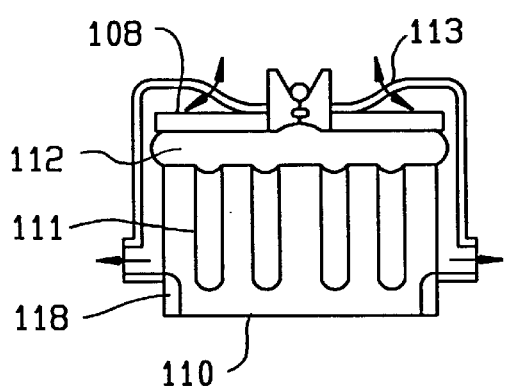
Figure 5C:
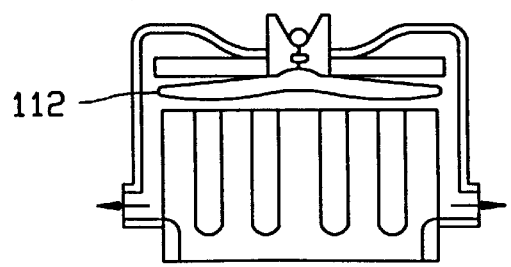

An alternative embodiment of sealing means for such reaction vessel arrays is illustrated in FIGS. 5A–C. The reaction vessel array is here illustrated as microtitre block 110 with deep wells 111. It will be immediately apparent how to adapt by scaling this sealing means to microtitre plates with standard wells. This sealing means comprises backing plate 108, inflatable bag 112, and retaining clips 114. Backing plate 108 is the base support structure for this sealing means and is preferably made of a metal, such as aluminum, or a rigid plastic. Bag 112 is sized to cover all the well openings of microtitre block 110 and is of a flexible, inflatable solvent resistant material capable of tightly occluding all the wells of plate 110 when sufficiently inflated. Bag 112 is preferably made of polypropylene or Teflon™ capable of being inflated to a pressure sufficient to retain the sealing balls against internal vapor pressures in wells. Pneumatic attachment 109 is for intermittently connecting to a pneumatic line for inflating or deflating bag 112.

Clips 113 are designed for retaining the sealing means to block 110 and to permit the standard robot arm gripper tool to place and to remove the sealing means for the reaction vessel array. Accordingly, clips 113 include horizontal tongues 115 for clipping securely into recesses 118 of microtitre plate 110. These clips further include lateral recesses 116 and upper horizontal shelf 117 designed to engage with gripper tool 123. Spring section 114 of these clips generates a vertical force for retaining these sealing means to plate 110 when bag 112 is uninflated and for exerting a vertical force against the inflation of bag 112. FIG. 5B illustrates bag 112 in an inflated condition, in which it tightly occludes all orifices of deep wells 111. FIG. 5C illustrates bag 112 in an uninflated condition, in which the sealing is retained against block 110 by the spring force generated by clips 113.

FIG. 5A also illustrates a multi-function gripper tool 123, which is adapted both for gripping and transporting reaction vessel arrays, such as microtitre block 110, and for placing and removing sealing means, such as those retained by clips, such as clip 113 or clips 103 of FIG. 4C. Gripper tool 123 is one of a plurality of interchangeable, specialized robot arm tools which attach to robot arm 120 through a standard attachment base contained in tool body 121. This attachment base is adopted to the particular robot arm used in an embodiment of this invention, and provides both for physical connection between a tool and the arm and for coupling of control and feedback lines, such as electrical or pneumatic control feeds between a tool and the arm. Tool body 121 also includes activating means, e.g., an electrical solenoid or motor or a pneumatic cylinder, for moving gripper fingers 122 horizontally. Gripper fingers 122 are vertically and horizontally offset from base 121 in order to minimize interference between robot arm 120 and any elements gripped by tool 123. Commercial suppliers of such a gripping tool include SAIC, Inc. (San Diego, Calif.) and Zymark, Inc. (Hopkington, Mass.).

It is advantageous to minimize the number of specialized tools in an embodiment of this invention, both to minimize cost and to improve throughput, since tool interchange requires non-productive robot arm time. Accordingly, clips 113 are configured so that the standard gripper can place and remove sealing means retained by such clips. To place a sealing means retained by clips 113, gripper tool 123 engages lateral recesses 116 of the clips by expanding gripper fingers 122 laterally. The robot arm then positions the sealing means over a reaction vessel array so that clip tongues 115 can engage array recesses 118. During this positioning, gripper fingers 122 can engage horizontal clip shelves 117 in order to lift the sealing means against gravity, and can engage fingers 115 to pull the sealing means down into position on a reaction vessel array. Then it moves fingers 122 inward horizontally, allowing clip tongues 115 to engage recesses 118, and then withdraws from engagement with clips 113. To remove such a sealing means, gripper tool 123 reverses these steps. Fingers 122 first engage with lateral recesses 116 of clips 113; fingers 122 then move horizontally outward to disengage clip tongues 115 from array recesses 118; gripper tool 123 finally lifts and removes the sealing means from reaction vessel array 110 by engaging against horizontal shelves 117.

5.2.3. Arrays of Independent Reaction Vessels

Figure 6A:
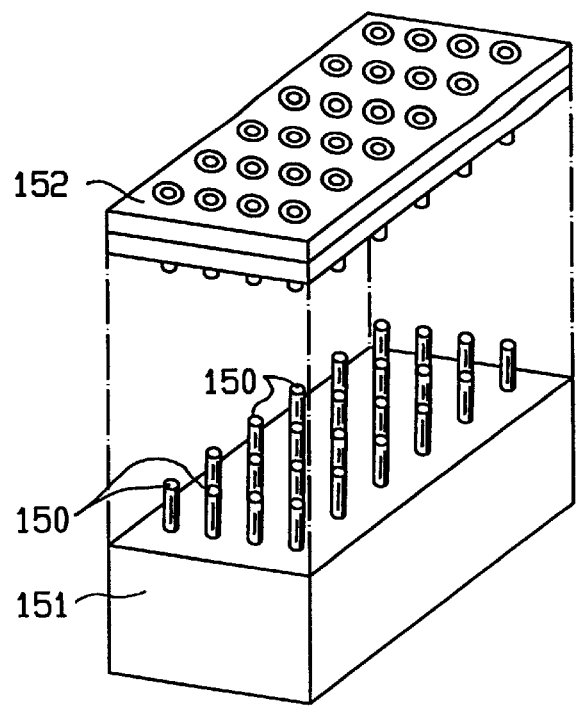

Another embodiment of reaction vessel arrays of this invention uses a compliant ball assembly to seal arrays of independent reaction vessels. However, such a ball assembly is not so limited and can be used to seal, not only the independent reaction vessel arrays of this embodiment, but also other arrays of reaction vessels having apertures, such as, e.g., the wells of microtitre plate embodiments. Alternately, the arrays of independent reaction vessels of this embodiment can be sealed by other sealing means, such as, e.g., those adapted also to seal microtitre plate embodiments FIG. 6A generally illustrates this embodiment. Individual reaction vessels 150 are supported in a reaction vessel array, or holding block 151, which has both a standard form factor and a standard array structure or layout for the independent reaction vessels, according to a particular embodiment of this invention. In one exemplary embodiment, holding block 151 has a standard microtitre physical form factor of 85×130 mm and supports 24 reaction vessels of 4 ml capacity in a standard 4×6 rectangular array layout. This embodiment is adaptable to other standard reaction vessel array layouts, array sizes, and reaction vessels. The reaction vessels of a reaction vessel array according to this embodiment can be sealed in various manners, including compliant ball assembly 152, and an assembly of valved caps, punctureable septum, and so forth, to be described in subsequent subsections.

Figure 6B:
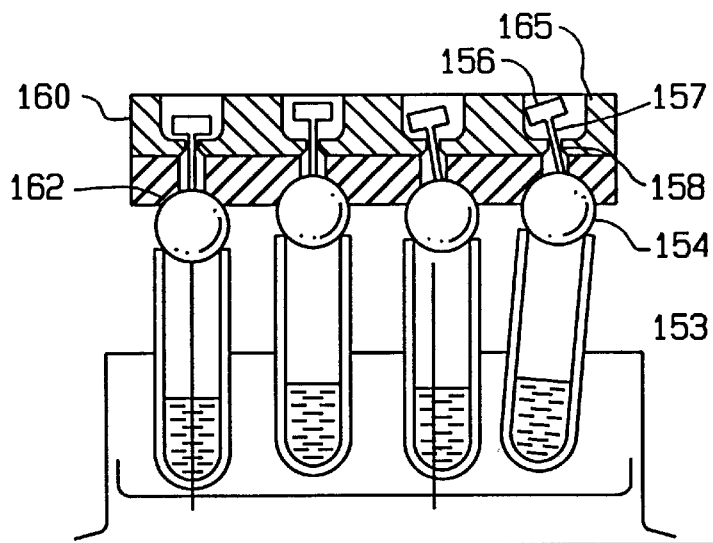

Generally, a compliant ball assembly comprises a plate to which are compliantly fastened an array of sealing balls having an arrangement designed to mate with the apertures of the reaction vessels in a reaction vessel array. The compliant attachment permits slight lateral motions of the sealing balls, in order to accommodate slight misalignments of the reaction vessels in the reaction vessel array, and also provides for applying a vertical sealing force to the sealing balls, in order to seal the apertures of the reaction vessels. The compliant attachment preferably permits lateral motions of no more than approximately ⅛ to ¼ of the diameter of a sealing ball. By way of example, FIG. 6B illustrates reaction vessel 153, which has a slight lateral misalignment, that is nevertheless sealed by sealing ball 154, which has undergone a slight lateral motion to accommodate for the slight misalignment of reaction vessel 153. As in other sealing ball embodiments, previously, the sealing balls are of a solvent resistant material, such as Teflon™, and one sized to be at least approximately of a diameter equal to 1⅛ to 1¼ times the diameter of the apertures of the reaction vessels to be sealed.

Figure 6C:
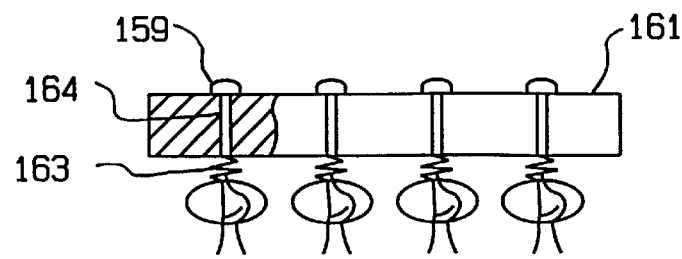

This embodiment includes alternative compliant attachment means of the sealing balls to the support plate that are known in the art. In particular, FIGS. 6B–C illustrate two preferred compliant attachment means. In the compliant attachment means illustrated in FIG. 6B, each sealing ball 154 is attached to a pin comprising pin head 156 and pin shaft 157. Aperture 158, pin shaft 157, and plate 160 are of such relative sizes that, although pin head 156 can not pass through aperture 158, pin shaft 157 has the desired range of lateral motion in aperture 158. Pin head 156 can be in recess 165 of plate 160, or alternatively, recess 165 can be absent, in which case pin head 156 can be retained directly on the top surface of plate 160. Compressible layer 162 on the face of plate 160 provides both a force resisting lateral sealing ball motion, thus establishing the compliance of the assembly, and a force for sealing balls 154 into reaction vessels 153. Preferably plate 160 can be of a metal, such as aluminum or a rigid plastic, and compressible layer 162 is of a rubber, such as a rubber of foam silicone type.

FIG. 6C illustrates an alternative compliant attachment means using springs 163 in place of compressible layer 162. The sealing balls are similarly retained by plate 161 with pins having pin shafts 164 and pin heads 159, as in the previous compliant attachment means. However, in this means, both lateral and vertical force are provided by springs 163. The vertical force arises by direct vertical compression of springs 163. The lateral force arises due to compression of the springs when the wide pin heads 159 rotate against the plate surface 161.

The compliant ball assemblies of this embodiment can be retained to a holding block in various ways. In one alternative, the ball assemblies are retained to holding block 151 with spring clips in a manner similar to that illustrated in FIG. 5A, where spring clips 113 engage recesses 118 in block 110. Using such spring clips, the compliant ball assemblies can be placed and removed by a standard robot gripper tool in a manner similar to that disclosed in the previous embodiment.

Figure 6D:
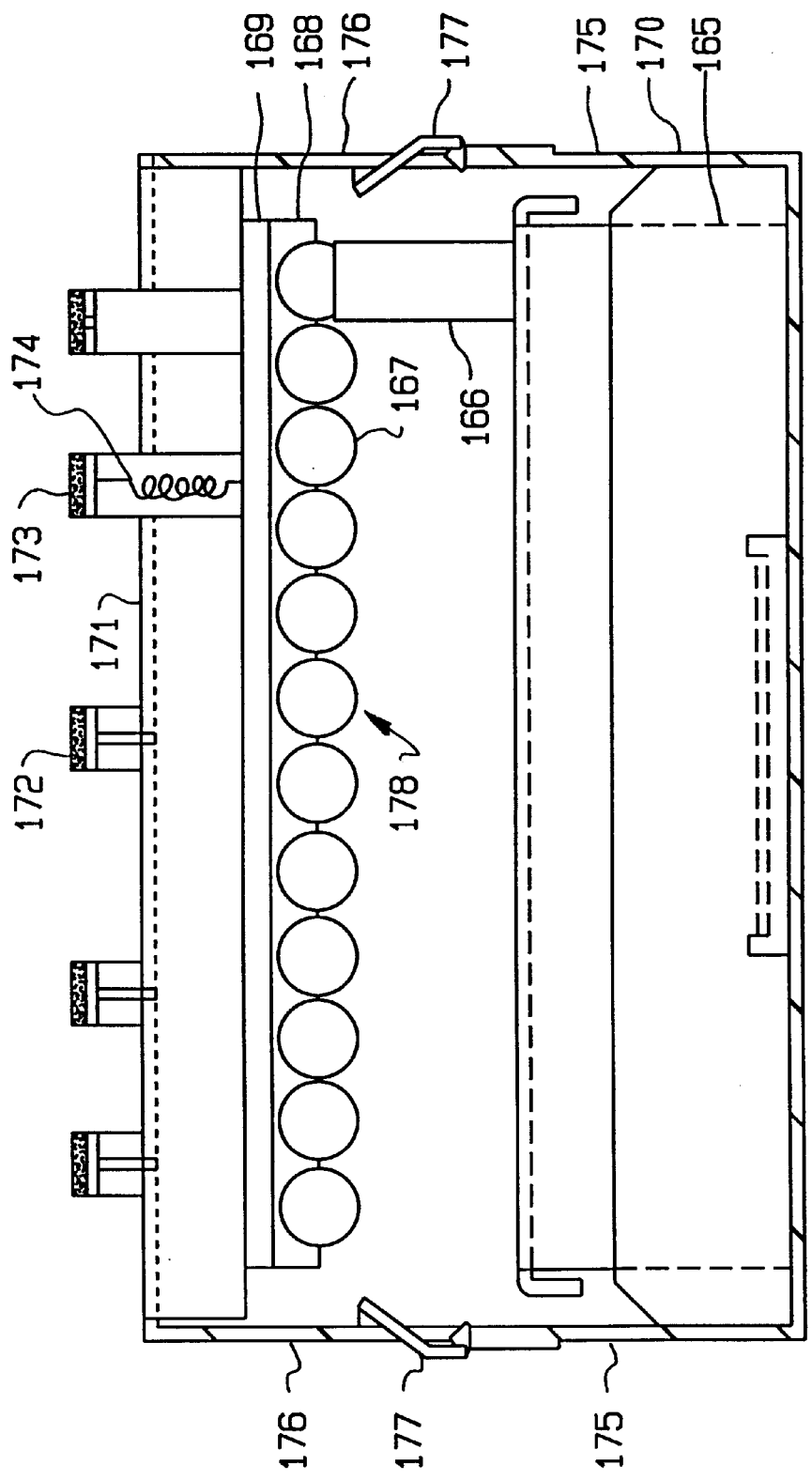

In another alternative, the ball assemblies are retained and sealed to reaction vessels by attachment assemblies illustrated in FIG. 6D. Generally, holding block 165 is retained by lower assembly 170, while compliant ball assembly 178 is retained by upper assembly 171. Both assemblies are held together by clips 177, and thereby retain the compliant ball assembly and reaction vessels in the holding block in sealing engagement. In more detail for the embodiment illustrated, holding block 165 holds an 8×12 array of independent reaction vessels, one of which is reaction vessel 166. Lower assembly 170 retains holding block 165 in a central position, and has extensions 175 at two ends which in turn have recesses for accepting and engaging with clips 177. Clips 177 automatically engage when the two assemblies are pressed together. Further, they have portions protruding from extensions 175 in order that they can be released by a gripper tool attached to a robot arm. Compliant ball assembly is of the embodiment illustrated in FIG. 6A, and includes sealing balls 167 restrained by compressible layer 168 and attached to backing plate 169. Illustrated reaction vessel 166 is sealed by one of the sealing balls. Upper assembly 171 retains the compliant ball assembly, and also has extensions 176 at two ends which in turn have support clips 177 which engage with recesses in extensions 175 of lower assembly 170. The compliant ball assembly is retained to the upper assembly by means of spring-loaded tubes 172, which engage the ball assembly. Upper assembly 171 includes regularly spaced apertures capable of accommodating tubes 172. These tubes are retained to the upper plate either by a pressure fit into these apertures, by u-rings fitted on tubes 172 preventing motion through these apertures, or by other means known in the relevant arts. Preferably, upper plate 171 has ten regularly spaced apertures for so retaining ten tubes 172. Spring loaded tube 173 is illustrated in cross-section to reveal internal spring 174, which links the top of tube 173 with ball assembly 178. The springs and containing tubes are sized such that, when the upper and lower assemblies are clipped together, the backing plate 169, and thus sealing balls 167, are urged against reaction vessels in holding block 165. Thereby, the upper and lower assembly achieve a sealing engagement between a compliant ball assembly and reaction vessels in a holding block.

5.2.4. Valved Reaction Vessels

An alternative sealing means for arrays of independent reaction vessels comprises valved caps. Preferred embodiments of such valved caps are simply constructed from inexpensive materials and are adapted so that all the valved caps in an array of reaction vessels can be simultaneously opened and closed by an inexpensive, easily constructed work station. The independent reaction vessels and the arrays of such reaction vessels are similar to those of the preceding subsection. This subsection describes in turn the structure of this sealing means, the opening/closing work station, and the method of their use in an integrated robot apparatus.

Figure 7:
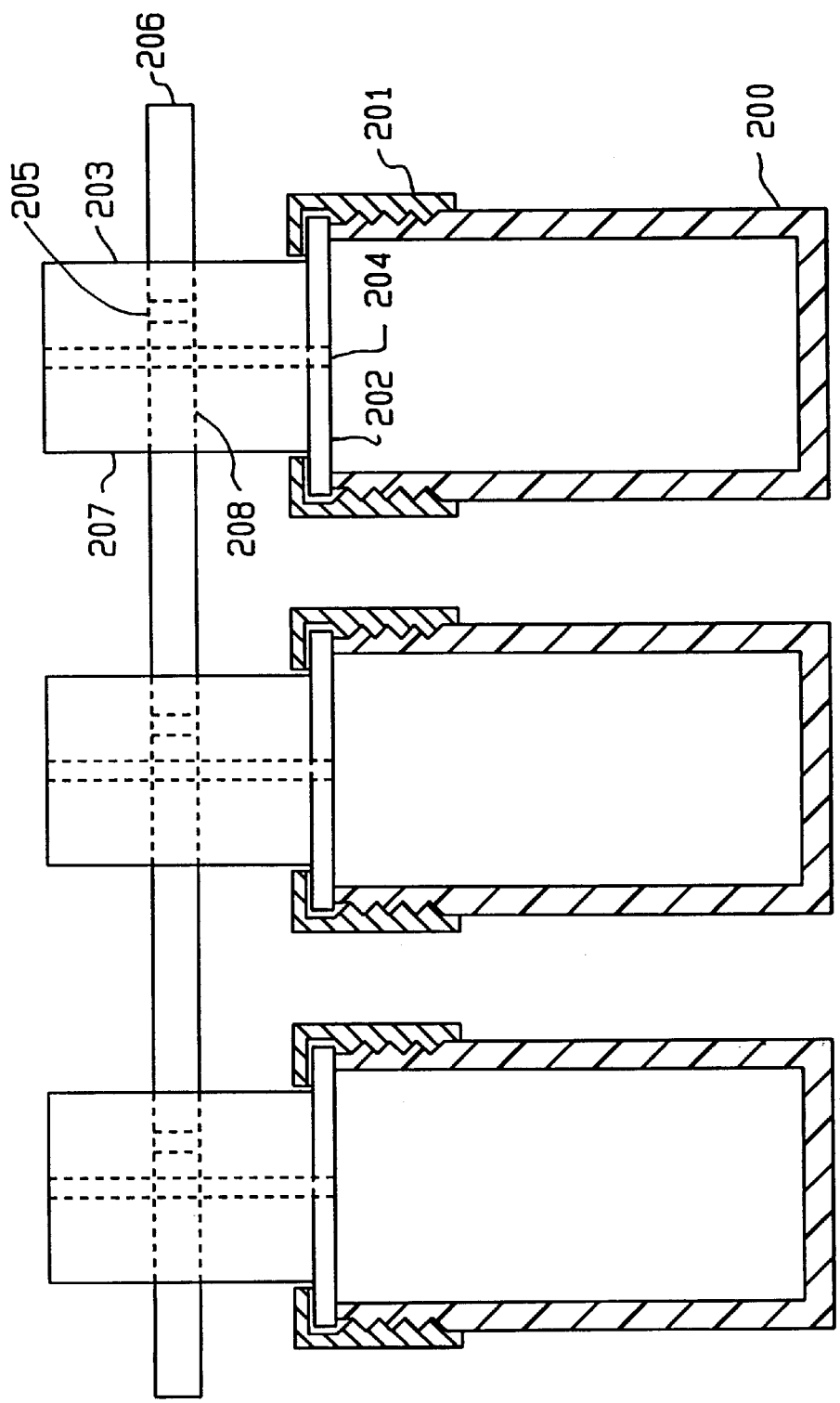

FIG. 7 illustrates an exemplary preferred embodiment of a valved cap sealing means. Reaction vessels 200 have threaded tops and are constructed from glass or solvent resistant plastic. An exemplary reaction vessel, adaptable to a 4×6 rectangular reaction vessel array occupying a microtitre form factor, is preferably of approximately 4 ml capacity and of a size of approximately 45 mm long by 15 mm in diameter. The valved top includes screw cap 201, valve body 207, and valve rod 206. Alternatively, the screw cap and the valve body can be combined into a unitary structure. Cap 201, of solvent resistant plastic or metal, is adapted to the threads of reaction vessel 200 for retaining and sealing valve body 207 to reaction vessel 200. Valve body 207 includes circular base 202, for sealing the valve body to the reaction vessel under pressure generated by valve cap 201, and cylindrical valve head 203, having central cylindrical orifice 204 for permitting communication between the exterior and the interior of reaction vessels 200. Orifice 204 is preferably approximately one-half the diameter of valve rod 206, or approximately 1 mm in diameter. The valve body is preferably constructed of Teflon™ or other solvent resistant plastic. Valve rod 206 fits sufficiently snugly in orifice 208 of the valve head to prevent fluid leakage around the rod through this orifice, and yet is capable of sliding laterally in this orifice in order to open or close the valves of this embodiment.

In the configuration illustrated in FIG. 7, valve rod 206 occludes orifice 204, fluid leakage around rod 206 is prevented, and the valve is closed. To open the valves, valve rod 206 slides laterally so that orifice 205 in the rod 206 is aligned with orifice 204 in valve head 203, thereby permitting communication between the exterior and the interior of reaction vessel 200. Importantly, all orifices 205 in valve rod 206 are spaced and positioned so that all of the valve bodies actuated by rod 206 are simultaneously opened at the same lateral position of rod 206. Rod 206 is preferably made of poly-vinyl difluoride ("PVDF") or stainless steel and is approximately 4 mm in diameter. This sealing means also includes such variants as, e.g., those in which valve body 207 is permanently attached to reaction vessel 200 by a metal or plastic retaining collar, those in which the dimensions recited are scaled to accommodate reaction vessels of differing capacities and sizes, and those in which valve rod 206 is rotated in order to seal the reaction vessels.

Figure 8A:
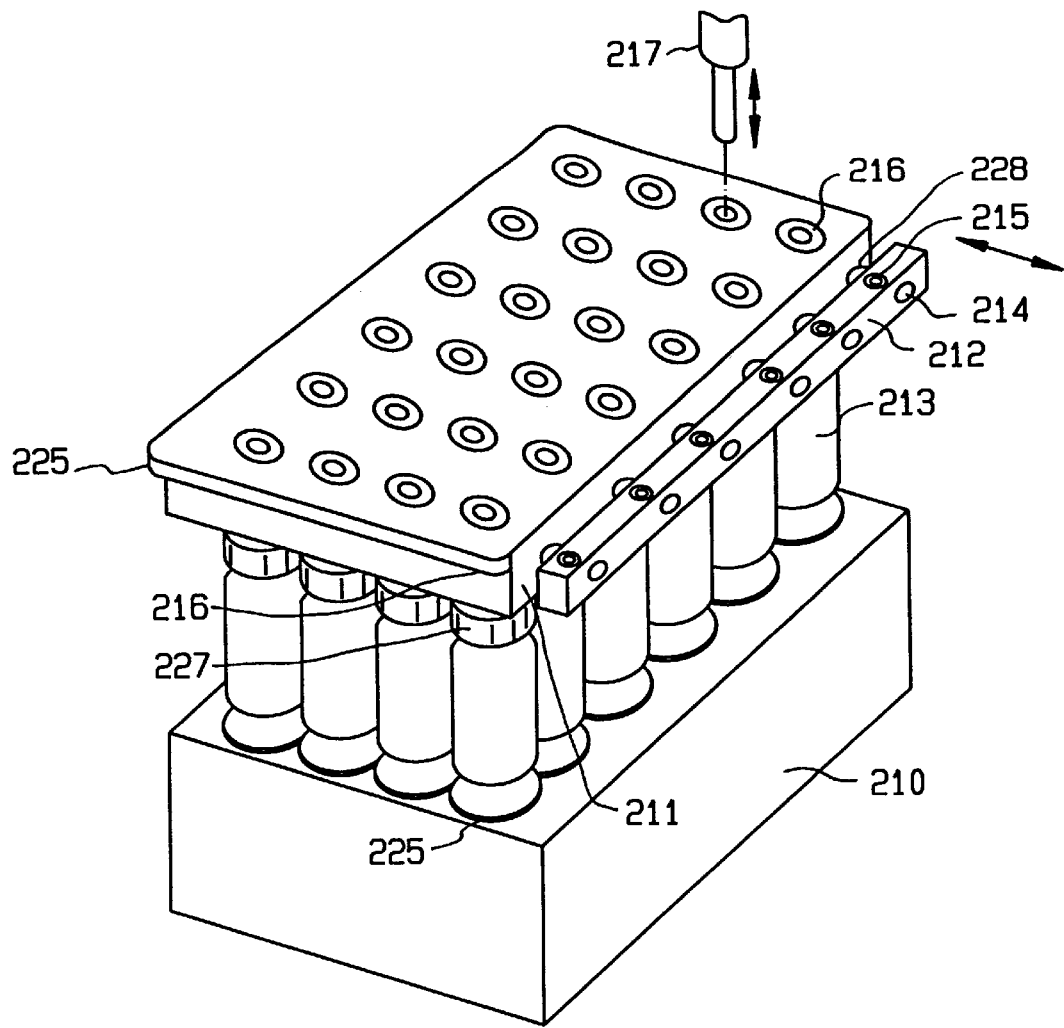

The valved reaction vessels of this embodiment are disposed in arrays of reaction vessels. Preferably, such arrays permit the simultaneous opening and closing of the valves of all the reaction vessels in the array, and have a size and structure so that the standardized fluid handling work stations, incubation work stations, and other elements of this invention, which can be used for other reaction vessel array embodiments, can also be used for the valved reaction vessel arrays of this embodiment. Accordingly, FIG. 8A illustrates one such exemplary array of valved reaction vessels. Plate 211 holds by, e.g., a pressure fit twenty-four valve bodies 216 and attached valve caps 227 in a 4×6 rectangular array. Alternatively, valve bodies 216 can be screwed into plate 211 or attached by other known means. Using standard 4 ml reaction vessels disposed with a minimum of approximately a 5 mm spacing between the reaction vessels, this reaction vessel array is supported by holding block 210 with a microtitre form factor of 85×130 mm. This invention is equally adaptable to other reaction vessel sizes, reaction vessel array sizes, and array structures in a manner apparent to one of skill in the art. Plate 211 has longitudinal lips 225 and 226 which are adapted so that plate 211 with reaction vessels 213 screwed into the attached valve caps can be supported in a specialized opening/closing work station described below. Plate 211 is preferably of a metal such as aluminum or a tough and rigid plastic such as Delrin™ (DuPont, Wilmington, Del.). Delrin™ is used generally herein to specify any of the Delrin type plastics or any plastics of equivalent chemical and physical properties.

Figure 8B:
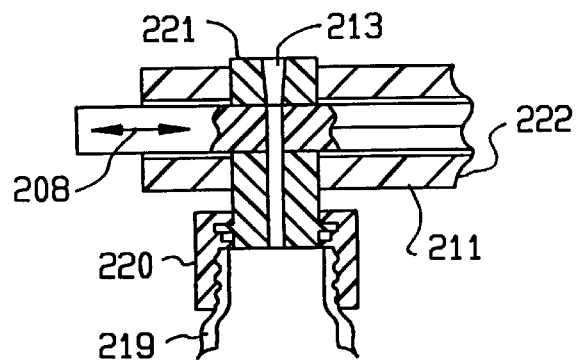

FIG. 8B illustrates a detail of plate 211 with the valve in an open configuration. Here, reaction vessel 219 is screwed into valve cap 220, which seals valve body 221 to the reaction vessel 219. Valve body 221 is retained in plate 211 by a pressure fit. Valve rod 208 slides freely and laterally in orifice 222 in plate 211 for opening and closing the valves. Valve rod 208 is illustrated in an open position, in which orifices 223 in the rod and the valve body are aligned permitting communication between the exterior and the interior of reaction vessel 219. To close this valve, rod 208 is moved laterally so that these orifices are no longer in alignment.

All valve rods 228 in FIG. 8A actuating all of the valves of the array of reaction vessels have control orifices so spaced and are so affixed to linkage segment 212 such that all the valves in the array can be simultaneously opened or closed by lateral motion of linkage segment 212. Linkage segment 212 is preferably of a metal such as aluminum in which valve rods 214 are affixed by set screws 215, such as set screws with a pointed tip. When linkage segment 212 is so positioned laterally so that all the valves are opened, fluid can be aspirated or dispensed into any of the reaction vessels 213. For example, syringe 217 is dispensing a building block solution into one of the reaction vessels of the array. Finally, holding block 210 supports this reaction vessel array when it is not in a specialized work station. Holding block 210 has recesses 225 for closely accommodating reaction vessels 213 when attached to valve caps 227 fixed to plate 211. Block 210 preferably affords heat conduction to reaction vessels 213, by being constructed of a heat conducting material, such as aluminum.

Figure 9:
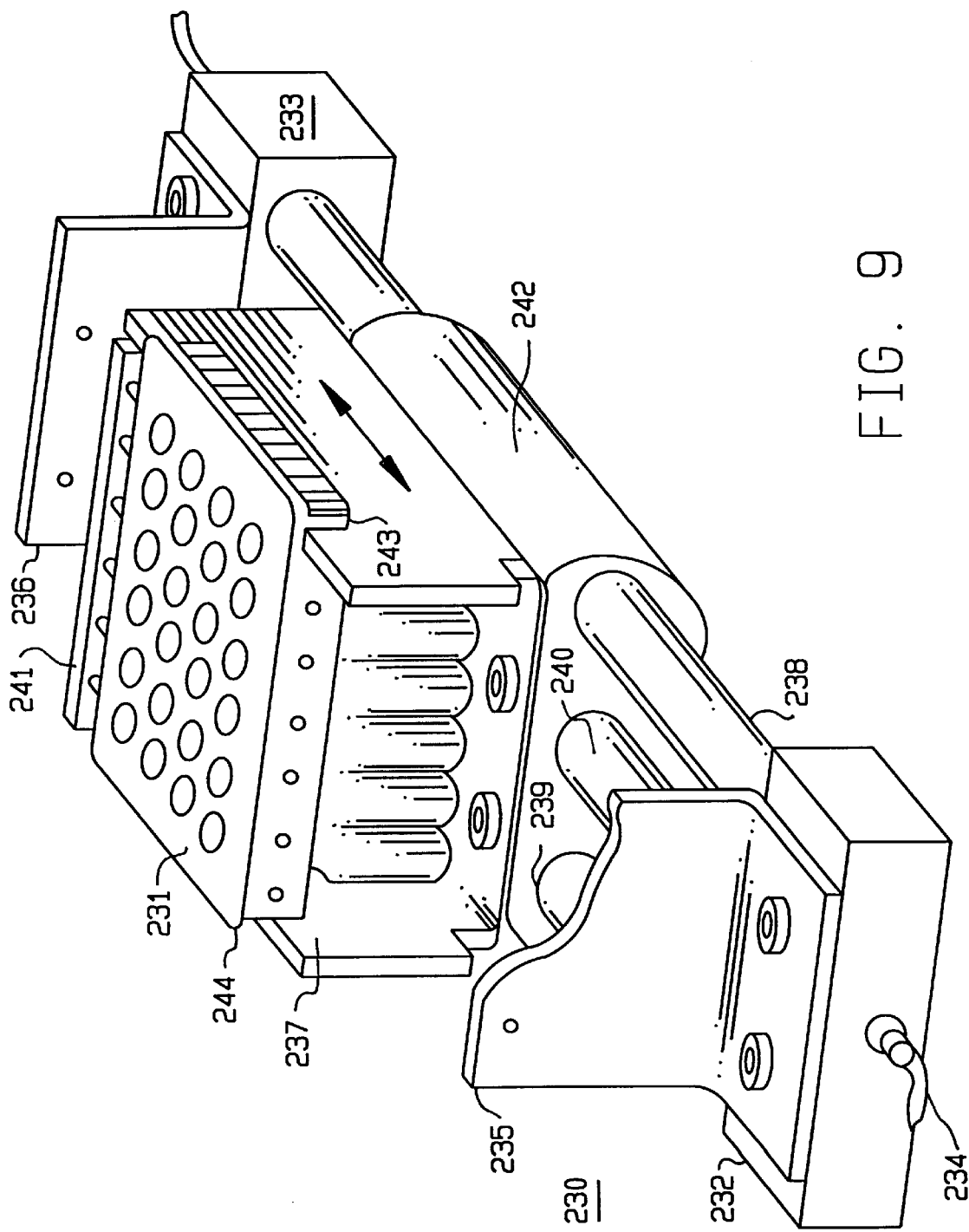

FIG. 9 illustrates a specialized work station for opening and closing all the valves in the array of reaction vessels according to this embodiment. This is done by moving laterally linkage segment 241 of the array 231 between its opened position and its closed position. A controllable actuator provides for such relative lateral motion between linkage 241 and array 231. In detail, this work station includes support blocks 232 and 233, which support rods 238 and 239 and actuator 240. Holder 237 retains plate 231 supporting the array of reaction vessels in a relatively stationary position by engaging lips 243 and 244 of plate 231. Holder 237 is supported by holder support 242, which slides on support rods 238 and 239 under a force developed by actuator 240. End plates 235 and 236 limit the motion of holder 237, and end plate 236 specially also engages and fixes linkage segment 241. Accordingly, as actuator 240 generates a force moving holder 237 along support rods 238 and 239, the linkage segment, fixed by end plate 236, moves with respect to array 231 and all the valves in reaction vessel array 231 simultaneously opened or closed. Actuator 240 is preferably a pneumatic actuator with pneumatic pressure feed 234, although this work station is adaptable to other actuators, such as electric actuators. The materials of this work station are preferably metal, such as aluminum, or a sufficiently tough and rigid plastic, such as Delrin™, except for the sliding members, which are preferably of a harder wear-resistant material, such as steel.

An exemplary implementation of this work station is constructed from components manufactured by Bimba Manufacturing Company (Monee, Ill.). Blocks 232 and 233, rods 238 and 239, and actuator 240 are components of part number #UGS-12-02.000-A. Supports 235 and 236 are part number #UGS-4-0703.

The following exemplary methods illustrate the use of the elements of this embodiment in an integrated robot during one step of building block addition. First the valved reaction vessel array, such as array 231 of FIG. 9, is placed by a robot arm in the specialized opening/closing work station of FIG. 9. This work station is then actuated to open all the valves in the reaction vessel array. The robot arm then places the opened reaction vessel array in a holding block, and moves the holding block, to wash solvent dispensing and aspirating stations for repetitive solvent washing. Next, building block and reagent additions are performed by fluid dispensing elements. The robot then moves the holding block with the reaction vessel array back to the specialized opening/closing work station, and places the reaction vessel array in this work station, which is then actuated to close all the valves in the array. The robot arm then places the closed reaction vessel array back in the holding block, and places the holding block with the reaction vessel array in a temperature controlled incubation work station, where it resides for a time and at a temperature sufficient for the building block addition reactions to go to substantial completion. The incubation work station is preferable below the work surface, and its access elevator is raised for robot arm access and lowered for incubation. Finally, in preparation for the next building block addition step, the robot arm removes the holding block from the incubation station and the reaction vessel array from the holding block, and places the array back in the opening/closing work station.

Figure 10A:
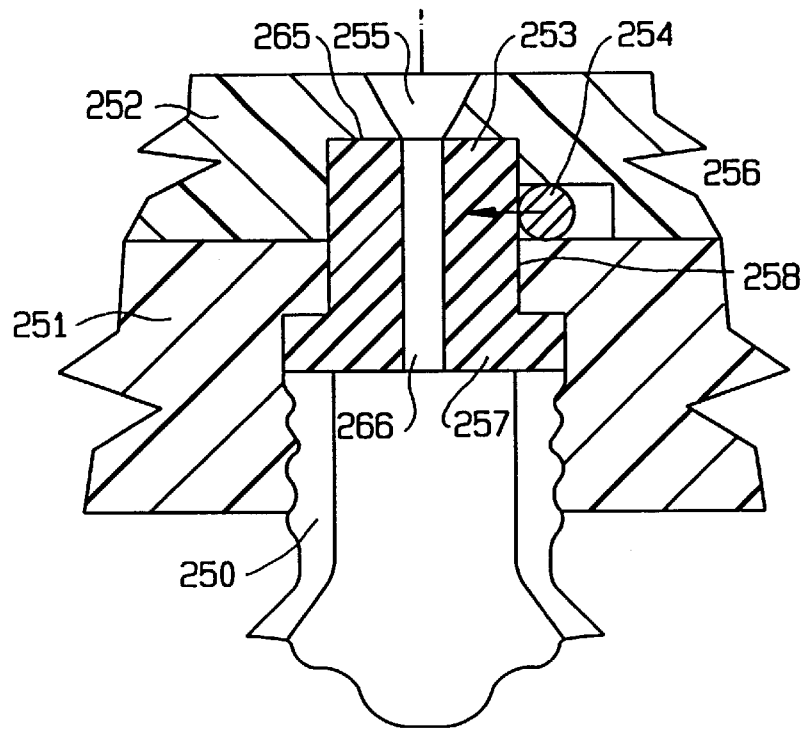
Figure 10B:
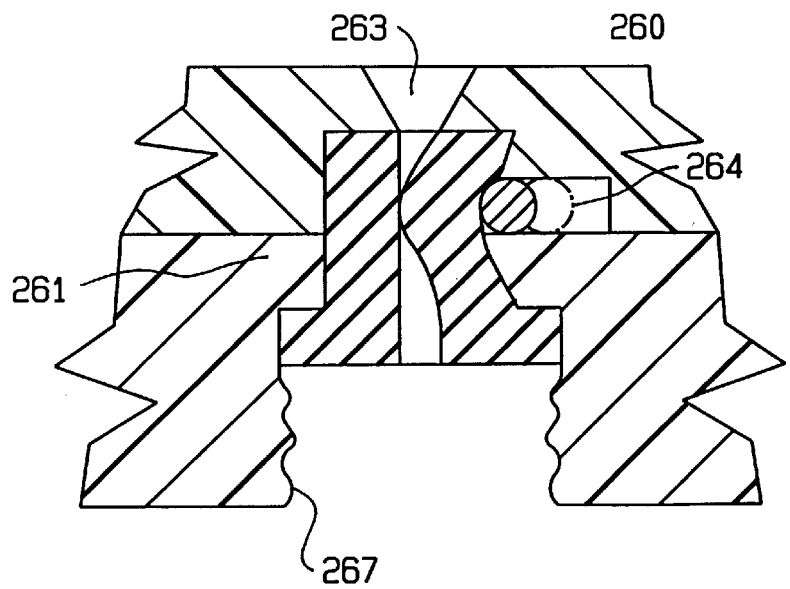

This embodiment is adaptable to other valve means for sealing reaction vessels. FIGS. 10A–B depict one such alternative valve sealing means having compressible valve body compressed with a rigid valve rod. In FIG. 10A, base plate 251 has threaded ports for receiving reaction vessels, which are preferably disposed in an array layout of a standardized structure. Plate 252 has cylindrical recesses 265 for receiving valve bodies 258 and for communicating with orifices 255. The orifices are aligned with the threaded ports in plate 251. Plates 251 and 252 can be made alternatively, of a metal, such as aluminum, or a rigid solvent resistant plastic. Compressible valve body 258 includes lips 257 for sealing reaction vessel 250 so that valve head 253 with orifice 266 communicates with orifice 255 in plate 252. Valve body 258 is made of a flexible solvent resistant elastomer, such as Kalrez™ manufactured by DuPont (Wilmington, Del.). Reaction vessel 250 is screwed into the threaded port in plate 251 against lips 257 of valve body 258 and is thereby sealed.

Valve rod 254, which moves in longitudinal slot 256 of plate 252, is at least sufficiently rigid to compress valve head 253 and thus to occlude orifices 255 in valve bodies 258. Preferably, this rod is further sufficiently rigid to be able to compress a plurality of valve heads 253 linearly arranged in the reaction vessel array. FIG. 10A illustrates this valve in an open condition, in which valve rod 254 does not compress valve head 253, so that orifice 266 is open and communicates with orifice 255, permitting communication between the exterior and the interior of reaction vessel 250. FIG. 10B illustrates the valve of this embodiment in a closed configuration, in which valve rod 260 has moved laterally from open position 264, compressed valve head 261, occluded orifice 263, and thereby prevented communication between the interior and exterior of reaction vessel 267. Similarly to the previous embodiment, these alternative valve means and sealed reaction vessels can be supported in a reaction vessel array, which is sequentially placed in a specialized opening/closing work station or in a holding block during processing.

5.2.5. Septum-Sealed Reaction Vessels

A further alternative sealing means for independent reaction vessels comprises punctureable septums, either simple septums or septum assemblies adapted to resist greater internal reaction vessel pressures. Such a sealing means can comprise, alternatively, a single punctureable septum or assemblies including one or more punctureable septums together with other sealing elements.

Figure 11A:
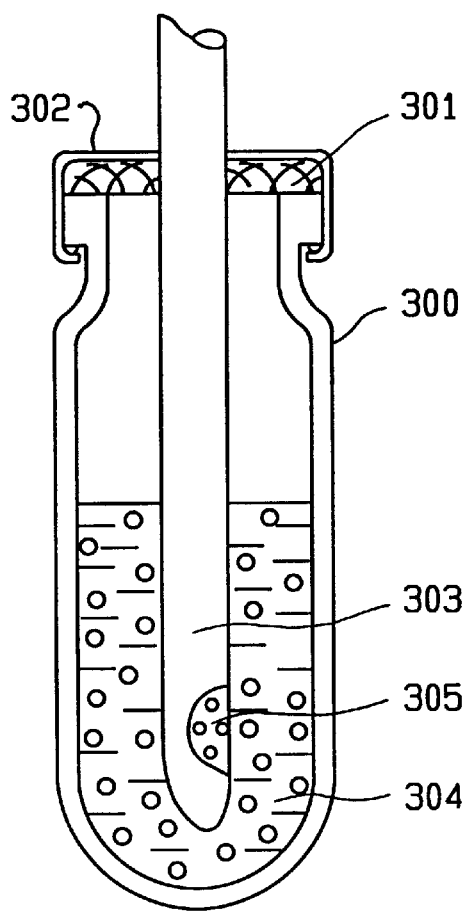

FIG. 11A illustrates a reaction vessel sealed with a single septum. Here reaction vessel 300 is preferably of approximately 4 ml capacity, and is made of glass or a solvent resistant plastic. Septum 301 is of a solvent resistant rubber material capable of being punctured by, e.g., a 14 gauge needle and then resealing itself. Septum 301 is preferably made of a Teflon™ coated rubber or of an elastomer of Kalrez™ type. Collar 302 seals septum 301 to reaction vessel 300, and is of, for example, aluminum or plastic. This invention is adaptable to commercially available, inexpensive septum-sealed reaction vessels, such as the reaction vessels obtained from such suppliers as Phase Separations (Franklin, Mass.) or ColePalmer (Niles, Ill.). Septum-sealed reaction vessels are retained for processing in arrays of standardized structure by holding hold blocks of standardized sizes, as in other reaction vessel embodiments of this invention. One exemplary such holding block is holding block 151 of FIG. 6A.

Figure 11B:
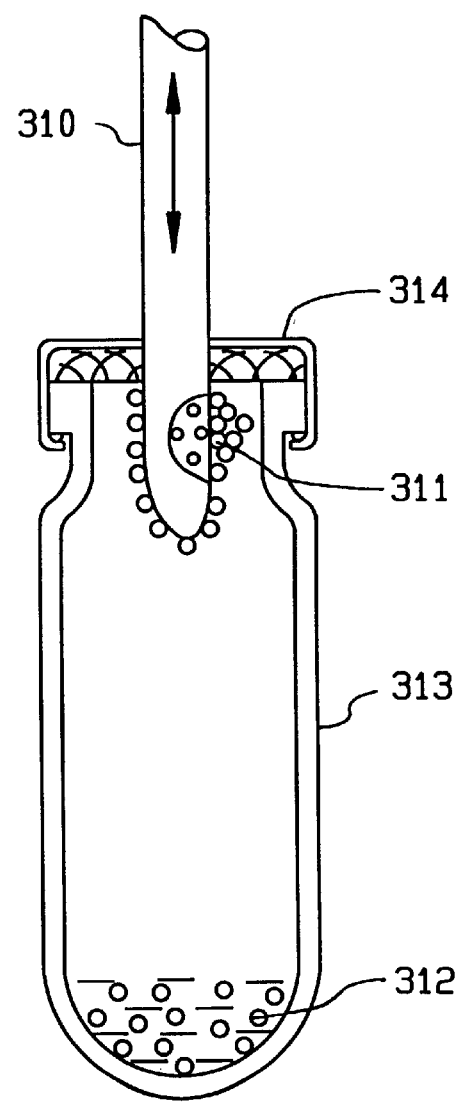

These reaction vessels are processed by needle-based fluid manipulation tools and workstations. Fluids are dispensed into such reaction vessels with a needle-tipped dispensing tool, similar to those to be subsequently described. Fluids are preferably separated and removed from a solid-phase substrate contained in these reaction vessels by a fritted aspiration needle of this invention, illustrated in FIGS. 11A–B. In FIG. 11A, fritted needle 303 has been inserted into reaction vessel 300 and is aspirating fluid contained therein through a lateral orifice occluded by a fritted material. Although fluid can penetrate this fritted material relatively freely, solid-phase substrate 304 can not penetrate it, and is thereby retained in reaction vessel 300. In FIG. 11B, substantially all contained fluid has been aspirated through needle 310, leaving solid-phase substrate 312 in reaction vessel 313. Any solid-phase substrate adherent to fritted needle 310, for example, substrate beads 311, are wiped off needle 310 and retained in the reaction vessel as the needle is withdrawn through resealable, punctureable septum 314. Alternatively, the fritted material may be replaced with other sieving means, such as an array of micro-drilled holes. Since adherent solid-phase material is not as fully removed from needles with end orifices containing a fritted material, such needles are less preferably used with these sealing means.

Figure 12A:
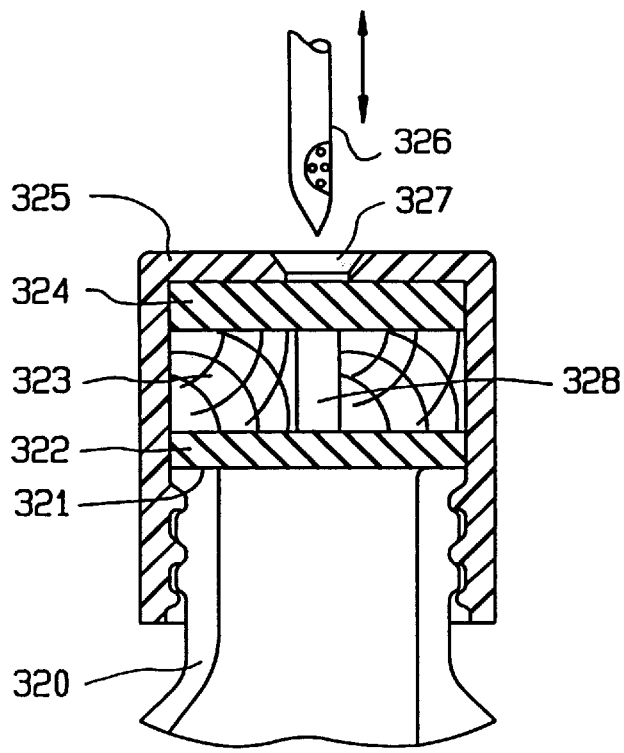
Figure 12B:
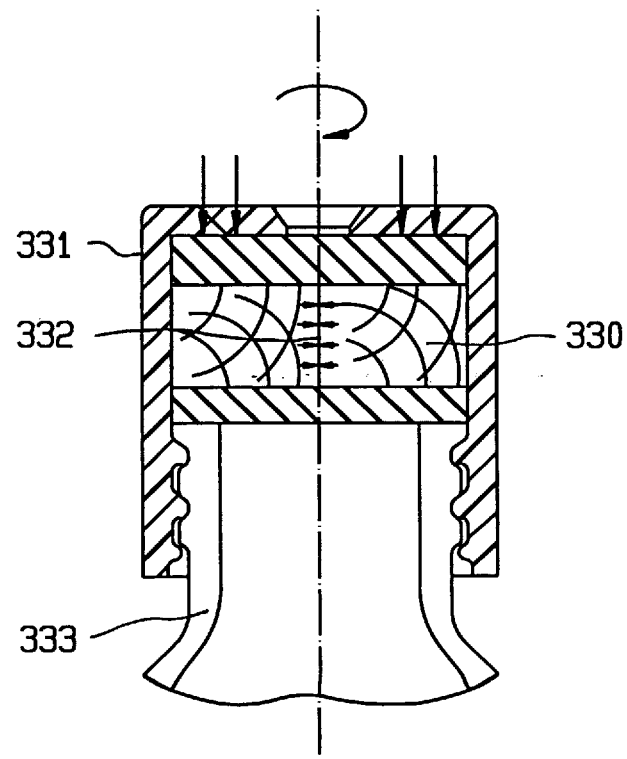

FIGS. 12A–B illustrate an alterative septum assembly that achieves more thorough sealing and can be adapted to resist greater internal pressures in a reaction vessel. Turning to FIG. 12A, this exemplary embodiment of the alternative septum assembly, as adapted to reaction vessels 320 having threaded necks, includes screw cap 325, punctureable septums 322 and 324, compressible collar 323, and rigid seal 321. Screw cap 325 retains and seals the septum assembly to reaction vessel 320, and includes aperture 327 for permitting access by needle-based fluid manipulating elements. Rigid seal 321 seals the septum assembly against the top of reaction vessel 320 with a rigidity sufficient to withstand pressures developed when screw cap 325 is screwed down onto the reaction vessel. It is, preferably, of a solvent resistant rigid plastic such as Teflon™ and has a central aperture for permitting needle access. Punctureable septums 322 and 324 are standard septums similar to those of the previous embodiment, and are also preferably made, from an elastomer of Kalrez™ type. In a relaxed state, compressible collar 323 has central orifice 328 for permitting passage of needle-based fluid manipulating elements. However, when vertically compressed, collar 323 is of a material such that orifice 328 becomes occluded. An exemplary material is the elastomer Kalrez™ manufactured by DuPont.

This alternative septum sealing means is used according to the following method. When screw cap 325 loosely seals the components of the septum assembly against reaction vessel 320, as in FIG. 12A, central orifice 328 of compressible collar 323 is open, and needle-based fluid handling elements can gain access to the interior of reaction vessel 320 through punctureable septums 322 and 324. In particular, as in the previous embodiment, this embodiment is adapted to the use of fluid removal elements based on a fritted aspirating needle, such as needle 326, or, when surface aspiration is used for fluid removal, on a flat-ended needle. When fluid handling is complete, screw cap 325 is screwed down on the threads of reaction vessel 320, vertically compressing the components of the septum assembly. Sufficient vertical pressure exerted between screw cap 325 and rigid seal 321 acts to compress compressible collar 323 and occlude orifice 328. FIG. 12B illustrates the septum assembly in a closed state, with collar 330 vertically compressed and orifice 332 occluded.

The additional element of this embodiment of septum sealing means—the screw cap, the multiple punctureable septum, the collapsible collar, and the seal—act to more thoroughly seal the reaction vessel and to increase the resistance of this septum assembly to internal pressures generated in a reaction vessel. Thus a reaction vessel sealed with this assembly can be subjected to higher incubation temperatures, where necessary for a particular synthesis protocol. It will be apparent to one of skill in the art that variations are possible in this alterative embodiment. For example, where more or less sealing is required, there can be only one or there may be more than two punctureable septums; where more pressure resilience is required, there can be more than one collapsible collar.

5.2.6. Syringe Arrays

This invention also includes arrays of syringe-like reaction vessels. Syringe-like reaction vessels are advantageous because their contents are always sealed by plungers, and, therefore, are never exposed to the atmosphere, thus avoiding the necessity of separate means to maintain reactions in an inert atmosphere. Syringe-like reaction vessels can be made in an integral form, using a single solvent-resistant block containing an array of cylindrical bodies, or can be assembled from individual, commercially-available syringes. Commercially-available syringes are advantageous because they are inexpensive and readily available. Such commercially-available syringes can be standard syringes manufactured for medical applications, having a capacity of approximately 1–10 ml and made of solvent resistant materials such as polypropylene. Syringe-like reaction vessels include porous frits in their bases for retaining solid-phase substrates while permitting relatively free movement of fluids. A preferred frit is made of polypropylene with a 5–30 micron pore size, a porosity of 50%, and capable of retaining solid-phase microbeads with a diameter >30 microns. Fluid handling for syringe arrays made according to either embodiment can, alternatively, be based on aspiration through needles from individual fluid storage vessels or on aspiration through a fluid distribution block from common fluid storage vessels. Exemplary syringe-like reaction vessel array layouts include a linear array of 8 syringes, an array of 24 syringes in a 4×6 rectangular arrangement, and an array of 96 syringes in a 8×12 rectangular arrangement.

FIG. 17 illustrates an exemplary 1-dimensional array of 8 syringe-like reaction vessels formed in a single block and using attached needles for fluid handling. Block 550 is formed of a solvent resistant material, e.g., Teflon™ with holes forming bodies 551 of the syringe-like reaction vessels. Each syringe-like reaction vessel, in addition to syringe body 551, has standard plunger 552, and frit 553 The frit in the base of body 551 retains a solid-phase substrate. At the base of each syringe body 551, straight fluid passageways 554 are formed in block 550. Fluid passageways are interrupted by valve rod 555, made preferably of PVDF or stainless steel, and mounted for lateral or rotary motion. Valve rod 555 functions in a manner similar to that of valve rod 206 of FIG. 7. This rod contains fluid passageways spaced and oriented so that they can all be brought into alignment with fluid passageways 554 in block 550 in order that fluid communication is established between the interior of syringe bodies 551 and the exterior of block 550. Thereby, by moving laterally or by rotating valve rod 554, the syringe bodies can be either sealed from or opened to the exterior. Needles 556 are attached to fluid passageways 554 to permit drawing and expelling fluids. A further element of this embodiment is a plunger holder similar to that illustrated in FIG. 18, which permits all the plungers in a syringe array to be accurately manipulated.

A fluid handling work station adaptable to this embodiment of syringe-like reaction vessels includes a support means for securely retaining block 550, and a plunger activation means for accurately positioning a plunger-holder attached to plungers 552 of the syringes. By manipulating the plunger-holder, fluids can be drawn into or expelled from all syringe bodies 551 of block 550. In this embodiment, solutions containing building blocks are stored in individual storage vessels. To dispense particular building blocks into particular syringes, the storage vessels containing the building block solutions are placed by the robot arm in an array having a layout conforming to the layout of needles 556 and in an arrangement such that all the correct building block solutions can be drawn into all the correct needles simultaneously. Needles 556 are then submerged in the building block solution in the storage vessels, and the syringe plunger-holder is accurately positioned outward to withdraw controlled aliquots of the building block solutions into syringe bodies 551. Similarly, for reagents and wash solvents, which are typically distributed to all the syringes in an array simultaneously, storage vessels containing these fluids are arranged in a storage array such that needles of the syringe array can also be submerged in all the storage vessels of the storage array simultaneously. Outward positioning of all the plungers of the syringe array at once then withdraws these fluids into the syringes. Such storage vessels can advantageously be similar to the septum-sealed reaction vessels of FIG. 11A, and retained in a storage array in a holding block similar to the holding block of FIG. 6A. Alternatively, these storage vessels and storage arrays can be similar to other reaction vessel embodiments previously described. Spent fluids can be expelled from the syringes into collecting devices for discarding by positioning inward all the plungers of a syringe array.

During a building block addition reaction, syringe arrays can be optionally agitated, or optionally placed in a temperature controlled incubation work station. Syringes of this embodiment can be arranged in other one and two dimensional array layouts and used with storage arrays having a corresponding structure.

FIG. 18A illustrates a second exemplary embodiment of a 1-dimensional array of 8 commercially available syringes attached to a fluid distribution block. In this embodiment, the syringes do not use needles for fluid handling. This embodiment includes an array of separate syringes 600 attached to fluid distribution block 601, which is shown partially cut away to reveal its internal passageways. Each syringe 600 has plunger 602, syringe nipple 606, and porous frit 603 at the bottom. The frit retains a solid-phase substrate while allowing relatively free flow of fluids. Syringes are preferably made of a solvent resistant plastic material, e.g. polypropylene, or glass, with plungers made of polypropylene or Teflon™. Plungers are fixed to plunger-holder 604. Manipulation of plunger-holder 604 moves all plungers 603 equally and simultaneously for drawing or expelling equal volumes of fluid in all syringes 600 in the array at the same time. Syringes 600 are mounted on syringe-holder 605, which presses syringe nipples 606 tightly into holes in block 601 to prevent any fluid leakage. Block 601 contains internal fluid passageway 607 that connects all syringe nipples 606 to common port 608. Each syringe 600 is also connected to punctureable septum 610 by straight fluid passageway 609. Punctureable septa 610 and passageways 609 allow needle-based fluid distribution tools to introduce particular reagents and building block solutions separately into each syringe.

As for the first embodiment, a fluid handling work station adaptable to this embodiment of syringe-like reaction vessels includes a support means for securely retaining block 601, and a plunger activation means for accurately positioning plunger-holder 604 attached to plungers 602 of syringes 600. Additionally, external fluid handling means, of which FIG. 18B illustrates an exemplary embodiment, are attached to common port 608 of FIG. 18A. First, for distribution of particular fluids to particular syringes, such as solutions such as solutions containing building blocks, common port valve 619 of FIG. 18B is closed, e.g. by electromagnetic or pneumatic means, to seal the common port against entry of unwanted fluids. Next, an array of needle based fluid distribution tools, having a needle layout conforming to the layout of septa 610 of FIG. 18A, is charged with building block solutions in an arrangement such that the correct building block solutions can be drawn into all the correct syringes. These distribution tools are manipulated so that their needles puncture septa 610 and advance into passageways 609. Finally, the plunger-holder is withdrawn and fluids from the distribution tools are drawn into syringes 600 as plungers 602 move outward by a determined amount.

Next, for distribution or removal of fluids from all the syringes of an array simultaneously, such as solvents or common reagents, the exemplary apparatus illustrated in FIG. 18B can be used. Here, a plurality of reservoirs 615, storing common fluids are connected through tube 616 to switching valve 617, then through exhaust valve 618, and finally to common port 622 in block 623 by tube 620. To dispense common fluids to all the syringes, controllable switching valve 617 selects the reservoir from which to withdraw fluids; exhaust valve 618 is directed to common port 622 through tube 620. When the plunger-holder withdraws all the syringe plungers, common fluids are drawn into the syringes. To expel fluids from all of the syringes, common port valve 619 is opened and exhaust valve is directed to fluid exhaust tube 621. When the plunger-holder is manipulated to depresses plungers into the syringes, fluids are expelled while the solid-phase substrate is retained by the frit in each syringe. The tubing used is preferably made of Teflon™ or other solvent resistant plastic. The fluid handling tubing, passageways, and valving illustrated in FIG. 18B are exemplary, and this embodiment is adapted to other arrangements of these elements which achieve similar results as are apparent to those of skill in the art.

In alternative embodiments, fluid handling means according to FIGS. 18A and 18B can be adapted to syringes constructed integrally in one block. Also, arrays of commercially available syringes are adaptable to the needle based fluid handling means as illustrated in FIG. 17. Also, although this apparatus was described for use in an automated robotic apparatus, it can be adapted for use as a standalone device, in which case it can be optionally manually actuated.

5.3. Fluid Handling Means

Fluid handling means of this invention, which are adapted to the previously described reaction vessel arrays, include specialized work stations and robot arm tools for dispensing and aspiration of fluids, including fluids containing slurries such as microbeads. Preferably, fluid dispensing means are specialized either for solvent washing or for dispensing individual building block solutions and reagents. On one hand, fluid handling means for solvent washing are preferably specialized for rapid and repetitive solvent distribution to most, or to substantially all, of the reaction vessels of an array. For solvent washing, rapid fluid distribution and removal is more advantageous then accurate fluid distribution. On the other hand, dispensing building block solutions and reagents is done once per synthesis step with, preferably, greater accuracy. Since, typically, a separate building block solution is dispensed to each separate reaction vessel in a reaction vessel array whereas the same few reagents are dispensed to all reaction vessels in an array in which the same protocol is being performed, fluid handling means are advantageously specialized in various embodiments of this invention into separate means for building block dispensing and for reagent dispensing.

Accordingly, this section sequentially describes fluid dispensing means of this invention, a preferred embodiment of a fluid handling workstation means, and fluid and slurry dispensing means.

5.3.1. Fluid Aspiration Means

Fluid aspiration work stations or tools of this invention preferably aspirate fluids from reaction vessels while leaving behind in the reaction vessels substantially all of a solid-phase support to which intermediate compounds are attached. Since solid-phase supports include easily aspirated microbeads, the fluid removal elements are based on specialized aspiration needles or specialized aspiration methods which prevent microbead aspiration.

The specialized aspiration needles of this invention include a filtering or sieving means in the needle to prevent aspiration of solid-phase microbeads while permitting relatively free flow of fluid in both directions. Such a filtering means has a pore or hole size which is preferably 5–50% of the typical solid-phase bead size. A typical pore size is in the range of 5–50 microns. In one embodiment, such a filtering means can be an array of micro-holes drilled by a laser micro-drilling apparatus, as is known in the art and is commercially available. Another embodiment of a filtering means includes a frit, preferably a polypropylene frit with a porosity 35 μm, such as is supplied by Bel-Art Products, Inc. (Pequannock, N.J.). These or other filtering means can be placed either laterally in the side an aspiration needle, or terminally in the end of an aspiration needle. Lateral placement is preferred because this configuration is self-cleaning when used with septum-sealed reaction vessels. For reactions vessels not sealed with septums or with septum-sealed vessels and a needle with a terminally placed frit, before an aspiration needle is withdrawn, any adherent solid-phase support is advantageously removed by back flushing a small amount of the aspirated fluid.

Figure 13:
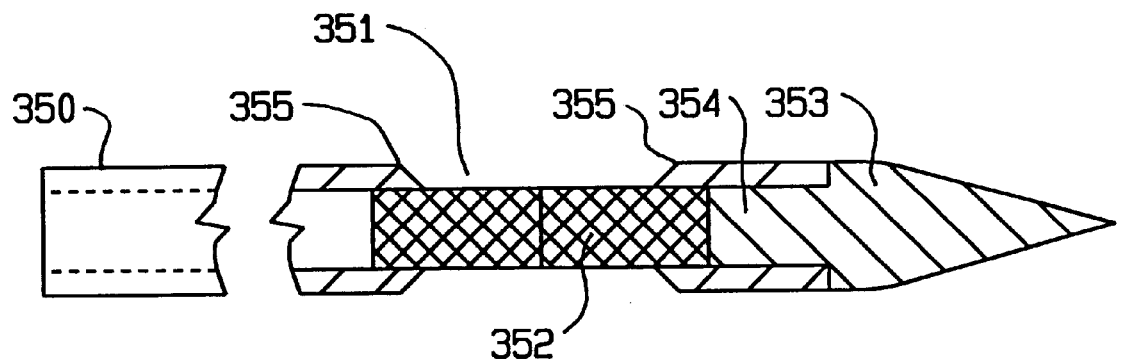
FIG. 13 illustrates a fritted, fluid aspirating or dispensing needle.

FIG. 13 illustrates an exemplary preferred aspiration needle structure with a laterally placed frit. To aspirate the maximum percentage of fluid from a reaction vessel, this needle is preferably long enough to reach to the bottom of a reaction vessel and is constructed with a minimum distance from the bottom of aperture 351 to the end of tip 353. Exemplary, dimension for needle 350 are an inside diameter of approximately 0.039 inches and an outside diameter of approximately 0.050 inches. Aperture 351 in needle 350 is lateral, oval shaped, and approximately 0.1 inches long. Pointed tip 353 has shank 354 pressure fit into the blunt end of needle 350, and is of approximately 0.19 inches overall length with a shank of approximately 0.06 inches. Cylindrical frit block 352 has a length of approximately 0.12 inches and is positioned against the end of shank 354 in order that the edges 355 of the aperture 351 overlap the cylindrical frit block by no less than at least approximately 0.01 inches. Cylindrical frit block 352 is of a diameter so that it is held in position in needle 350 against aspiration suction by static friction between the frit block and the inside surface of the needle. The dimensions recited herein are not limiting and the fritted needle can be scaled in a manner known in the art to dimensions appropriate for needles of other gauges, for example, of gauges 12–18. The use of this fritted needle with septum-sealed reaction vessels has been described in a previous subsection.

Figure 14:
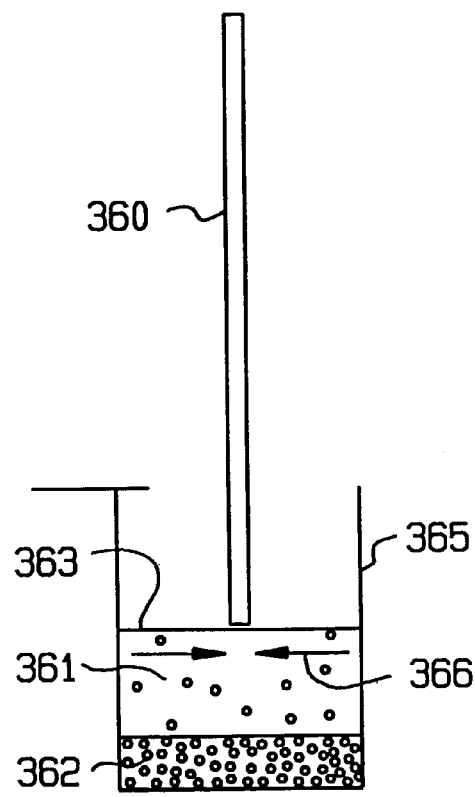
FIG. 14 illustrates a method of surface fluid aspiration.

FIG. 14 illustrates an alternative fluid removal method using a surface aspiration method of this invention. This method is based on the discovery that aspiration by a blunt ended needle at the surface of a fluid containing a settled solid-phase does not disturb that solid-phase, because such surface aspiration generates only radially in-flowing fluid currents confined to the surface of the fluid. It generates no currents in the bulk of the fluid that could disturb the settled solid-phase. Thus, in FIG. 14, reaction vessel 365 contains liquid phase 361 with settled solid-phase 362, such as solid-phase microbeads. Blunt-toucd needle 360 just touches surface 363 of liquid phase 361, and aspirates fluid 361 under an applied partial vacuum. During aspiration, needle 360, reaction vessel 365, or both, are moved relatively so that needle 360 remains in contact only with surface 363 of liquid phase 361. For example, needle 360 can be lowered or reaction vessel 365 can be raised. Thereby, this aspiration is carefully controlled so that only radially in-flowing surface currents 366 in fluid 361 are generated, such surface currents not disturbing settled solid-phase 362. Needle 360 can be, e.g., a blunt ended stainless steel needle of a gauge approximately from 12–18.

The relative motions of needle 360 and reaction vessel 365 can be controlled in various manners, including closed-loop or open-loop methods. In a closed-loop method, these relative motions are adjusted according to observations made during aspiration, e.g., of the vacuum present in needle 360, or of the rate of fluid aspiration in conjunction with the area of surface 363. In a preferred open-loop method, these motions are adjusted based on prior observations or experiments of surface aspiration under controlled conditions. For example, observations of aspiration rates of fluids of various viscosities through needles of various gauges subject to vacuums of varying amounts can be compiled, and later used to select a relative motion for a particular needle aspirating a particular fluid subjected to a particular vacuum in a particular embodiment.

5.3.2. Fluid Handling Workstations

Fluid removal tools or work stations utilize these previously described removal means. For improved throughput, it is preferable to implement fluid removal as a work station or tool capable of removing fluid from substantially all, or all, of the reaction vessels in a particular reaction vessel array in one operation. For example, removal of spent reagents at the end of a building block addition step can typically be done simultaneously for all the reaction vessels in an array. Also, since solvent washing can be done simultaneously for all of the reaction vessels in an array, removal of the wash solvent is preferably done simultaneously from all reaction vessels in an array.

Further, for throughput and economy, it is advantageous that a fluid removal station can also serve as a wash solvent dispensing station. Such a multi-purpose fluid aspiration/dispensing work station can improve robot throughput, by eliminating transfers of reaction vessel arrays between separate aspiration and dispensing stations during a solvent washing steps, and can minimize robot cost by requiring fewer separate components. In this regard, both preferred aspiration methods are also adapted to fluid distribution. Fluid may be freely distributed through the blunt ended needles used in the surface aspiration method, or may be relatively freely distributed through the fritted needles of this invention. Alternatively, and less preferably fluid removal by either the fritted needle or the surface aspiration method can be implemented as a tool or work station for removing fluid from a single reaction vessel or from only part of a reaction vessels array.

Figure 15:
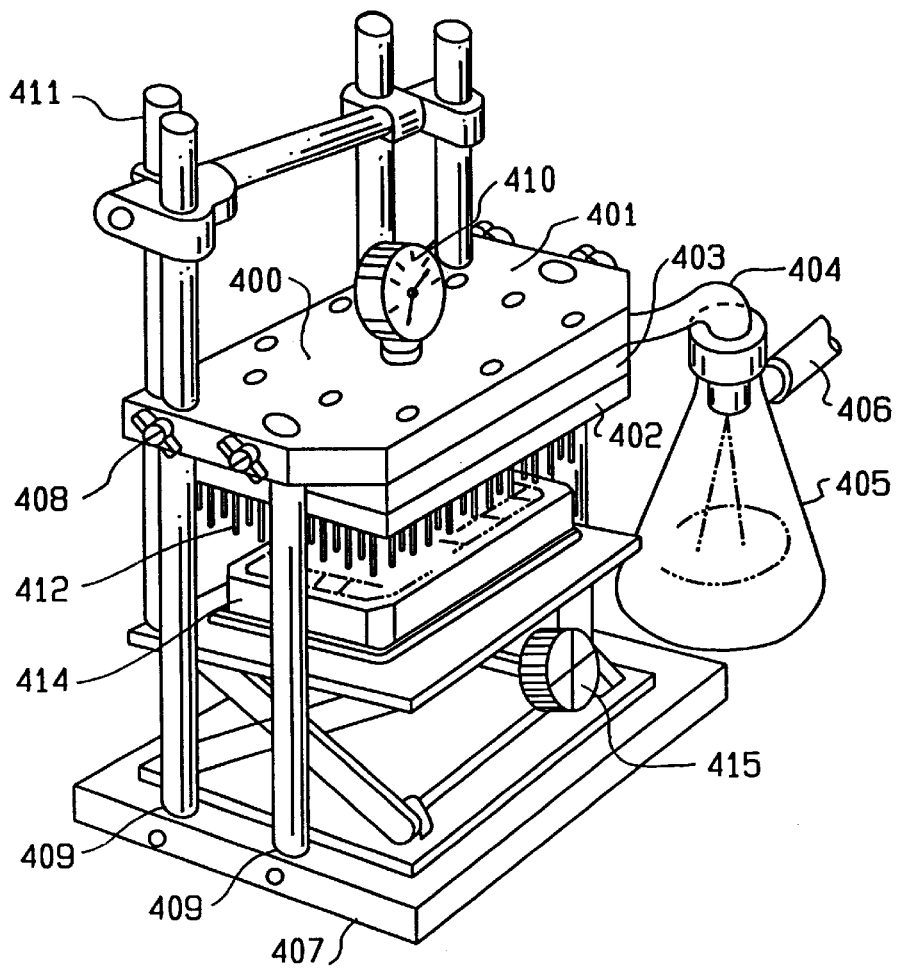
FIG. 15 illustrates a work station for fluid aspiration or for fluid dispensing.

FIG. 15 illustrates an exemplary embodiment of a multi-purpose fluid aspiration/dispensing work station implementing these preferred features. This station includes a support base and a fluid aspiration/distribution assembly with an array of needles. In the case of aspiration by using the surface aspiration method, this station also optionally can include means for providing relative motion between the aspiration needle array and the reaction vessel array. Therefore, base 407 provides for overall support of this work station, including rigid attachment of support rods 409. Fluid aspiration/distribution assembly 400 can be variably positioned on support rods 409 by, e.g., thumb screws 408. Distribution assembly 400 includes top plate 401, bottom plate 402, and plenum 403. Top plate 401 provides for the attachment of distribution assembly 400 to support rods 409. Top plate 401 also carries an optional number of sensors, which can be used in closed-loop methods of controlling surface aspiration, or simply for monitoring fluid handling. Illustrated here is vacuum sensor 410 for monitoring effective fluid aspiration vacuum.

Bottom plate 402 carries an array of aspiration/dispensing needles 412 arranged and spaced to match the arrangement and spacing of apertures of reaction vessel arrays. Therefore, one embodiment of this work station has bottom plate 402 with 96 needles 412 spaced in a 8×12 rectangular array to match reaction vessel arrays having 96 rectangularly arranged wells, and another embodiment has bottom plate 402 with a 4×6 array of needles conforming to reaction vessels arrays having 24 rectangularly placed reaction vessels. Needles 412 attached to bottom plate 403 can be, alternatively, fritted needles, flat ended needles for surface aspiration, or needles adapted to other fluid aspiration or distribution methods.

This workstation can be adapted to various arrangements of reaction vessels in arrays by merely replacing bottom plate 402, with its array of needles 412, with other bottom plates having needle arrays conforming to the reaction vessel array layouts to be serviced. For this interchangeability, it is advantageous in an embodiment of this invention, that reaction vessel arrays preferably have one standard footprint size.

Plenum 403 communicates between the base of needles 412 and a source of fluid for dispensing or a source of vacuum for aspiration. In one embodiment, a controlled valve can switch the plenum between a fluid source and a vacuum source. Here, plenum 403 is illustrated as permanently connected via connecting tube 404 to vacuum source 406 through fluid collecting reservoir 405.

In an alternative embodiment, this multipurpose workstation is instead specialized into either a fluid dispensing or a fluid aspiration function. In the case of a fluid dispensing workstation, plenum 403 is advantageously made smaller, so that less fluid is in transit during the dispensing process. In the case of a fluid aspirating workstation, plenum 403 is advantageously made larger, so that the vacuum or suction is maintained more evenly across all of the aspirating needles.

This multipurpose fluid aspiration/dispensing work station is used with reaction vessel arrays according to the following method. Reaction vessel array 414 is placed in an aspiration/dispensing work station with a conforming array of needles 412 by a robot arm with an attached gripper tool. For fluid dispensing and for fluid aspiration with fritted needles, the robot arm alone can position a reaction vessel array 414 in the work station and raise reaction vessel array 414 so that the needles penetrate fully into the reaction vessels. Alternatively, the work station can be provided with a means to raise and lower reaction vessel arrays. Preferably, a reaction vessel array is positioned so that the needles 412 will penetrate substantially to the bottom of the reaction vessels. Various mechanical or electrical feedback means can assist this positioning. Here illustrated is a mechanical feedback means composed of rod assembly 411, which provides a mechanical stop limiting motion of the reaction vessel array at the point of maximum needle penetration.

For fluid aspiration according to the surface aspiration method controlled according to an open-loop method, the reaction vessel array is raised at a fixed and pre-determined rate during aspiration. Again, this can be done by the robot arm alone, if it has sufficient position resolution to raise the reaction vessel array accurately at the pre-determined rate. Alternatively, the work station can have means for automatically and accurately raising the reaction vessel array at the pre-determined rate. Illustrated here is an embodiment of a raising means advantageous for use of this work station in a stand-alone and manual environment. Standard laboratory jack 415 is manually adjusted to raise reaction vessel array 414 at the correct rate for fluid aspiration.

5.3.3. Fluid and Slurry Dispensing Means

Fluid dispensing means are advantageously adapted to handling fluids alone or to handling fluids with slurries. Concerning dispensing means for fluids alone, as previously described, those for building block solutions, activating reagents, and other reagents are specialized differently from those for solvent dispensing. Since each reaction vessel in a reaction vessel array typically receives a separate one of perhaps hundreds of building block solutions, it is advantageous that building block solutions be dispensed by one, or at most a few common tools or work stations capable of dispensing solutions from one of a plurality of storage vessels of similar structure. Other embodiments, for example with a separate robot arm tool or work station for each building block solution, are less desirable in that such alternatives would typically require more storage volume or more work surface and cost more than the preferred embodiment.

Accordingly, and in a preferred embodiment, building block solutions are stored in commercially available syringe bodies having a capacity of, e.g., from approximately 10 to 50 ml. The robot arm gripper/dispensing tool removes such a syringe body from a storage rack, positions it for dispensing building block solutions into a correct reaction vessel, and then actuates the syringe plunger to accurately dispense an aliquot of the solution. When not being used, a syringe body containing a building block solution is stored in a below work surface storage station, which is raised above the work surface when needed for access by the robot arm.

Robot arm tools or work stations for distributing activating reagents or other reagents are advantageously designed for simultaneously and accurately dispensing such fluids to the several reaction vessels in an array, or to all the reaction vessels in an array, in which a single protocol is being performed. Since each synthesis protocol typically requires only a few common reagents, e.g., 2 to at most 6, it is advantageous for embodiments of this invention to have specialized reagent distribution tools or work stations for each required reagent. Therefore, a preferred exemplary reagent distribution tool, has a one or two dimensional array of fluid dispensing tips arranged and spaced to dispense reagents into the preferred reaction vessel arrays. Thus, there are separate embodiments of these tools for the rectangular reaction vessel arrays having 24 or 96 reaction vessels. In FIG. 16A, tool 460 has a one-dimensional array of dispensing tips, and in FIG. 16B, tool 470 has a two-dimensional array of dispensing tips.

Generally, these tools include an internal storage vessel for a fluid, a precisely controllable fluid pump, an array of dispensing tips, and tubing interconnecting the storage vessel, the pump and the array of tips. An exemplary fluid pump is a piston fluid pump manufactured by Cavro Scientific Instruments, Inc. (Sunnyvale, Calif.), with a model number XL3000. Finally, although it is preferable to distribute wash solvent at work stations such as that illustrated in FIG. 15, optionally, wash solvents can be distributed by tools similar to those illustrated in FIGS. 16A–B.

An additional class of fluid handling tools dispenses and aspirates slurries, for example, slurries of microbeads in a solvent. Such tools can be used to distribute fresh solid-phase substrate to reaction vessels prior to performing a synthesis protocol. Also, such tools permit the solid-phase substrates from a selected reaction vessels to be partially transferred to other selected reaction vessels, during, for example, various split synthesis protocols, in which multiple compounds are synthesized attached to one solid-phase microbead or in which one reaction vessel contains a mixture of microbeads, each microbead having attached a single synthesized compound.

Generally, solid-phase substrate in the form of microbeads are dispensed similarly to reagents. Such microbeads are maintained in a slurry in an appropriate solvent, and aliquots of the solvent containing the slurry are dispensed by a fluid distributing tool for slurries. A suitable solvent is dimethylformamide, and a suitable means to maintain the beads in a slurry is to bubble an inert gas, such as nitrogen, into a storage vessel containing the microbeads and the solvent.

In more detail, FIGS. 20A–B illustrate an exemplary apparatus for aspirating and dispensing slurries. This apparatus includes slurry container 800, made of glass or an inert plastic material, source of suction 801, fluid delivery module 802, valve 803, and connecting tubing 807. Container 800 has two openings, opening 804 located at the bottom with an attached narrow plastic or steel tube 806, and opening 805 at the top of the container connected to suction source 801 via valve 803. Valve 803 can be electromagnetically or pneumatically actuated. Tube 806 can be a standard needle, e.g., a 14 gauge needle. Fluid delivery module 802, which can be a syringe or a piston pump, is attached to connecting tubing 807 by a "T" piece.

Combining slurries from one or more reaction vessels into one or more other reaction vessels proceeds by a first step, in which slurries are aspirated from reaction vessels, and a second step, in which the aspirated slurries are dispensed. For the first step, valve 803 connecting container 800 with a suction source 801 is opened, and tube 806, attached to container 800, is immersed into reaction vessel 808 containing slurry 809, e.g., of resin beads. The suction draws slurry 809 into container 800 from reaction vessel 808. Next, container 800 with tube 806 is moved into those further reaction vessels, if any, whose slurries are to be combined, and this process is repeated. Distribution of a fresh solid-phase substrate into reaction vessels prior to a synthesis proceeds similarly, except that this first step is replaced by aspiration of the fresh substrate from a storage container holding fresh substrate, e.g., microbeads in a solvent.

For the second step, fluid delivery module 802 is adjusted to dispense a volume of air equal to the volume of slurry to be distributed from container 800 into a reaction vessel, e.g., reaction vessel 808. Then container 800 with tube 806 is moved above this reaction vessel, valve 803 is closed, and the determined and adjusted volume of air is introduced into container 800 by fluid delivery module 802. Thereby, an equal volume of slurry 810 from container 800 is dispensed into reaction vessel 808. After the first portion of the slurry is delivered, valve 803 is opened again, to facilitate mixing of the resin by the suction.

To prevent non-uniform distribution, the slurry can be preferably distributed in 2 or 3 phases. In a first phase, preferably 90–95% of slurry 810 is distributed into reaction vessels according to the previous process, leaving approximately 5–10% of the slurry remaining in container 800. Then this 5–10% residual slurry is diluted to the original volume by solvent, and a second distribution phase is performed, which leaves approximately only 0.25–1% of the slurry remaining. For even more complete distribution, this process can be repeated for a third phase.

The suction produced by suction source 801 serves two purposes. First, it serves to draw a slurry into container 800. Second, it serves to keep slurry 810 in container 800 mixed and homogeneous during the distribution process by drawing air or inert gas bubbles through the slurry. Therefore, suction source 801 should generate a moderate suction sufficient to accomplish these purposes, yet not strong enough to draw any slurry 810 back into connecting tubing 807. Further, a solvent used for phased distribution should be chosen among those with a high boiling point to prevent evaporation during distribution, e.g., dimethylformamide.

FIG. 20B illustrates an alternative embodiment of this apparatus for handling those slurries that must be protected from air. Such slurries include, for example, hydrides. In this embodiment single tube 806 is replace by coaxial structure 815 including and inner tube 811 and a coaxial outer tube 812. Inner tube 811 communicates with the interior of container 800 for aspirating and dispensing slurries. Outer, coaxial tube 812 surrounds inner tube 811 and protrudes beyond the end of inner tube 811. It includes a port 813 through which an inert gas, for example argon or nitrogen, can be introduced under a small pressure. Thereby, inner tube 811 is maintained in an inert atmosphere, and suction source 801 draws only this inert atmosphere through the slurry. Additionally, only this inert gas is introduced into delivery module 802. In this manner, a slurry can be exposed only to the required inert atmosphere.

In the exemplary embodiment described, this apparatus is configured as a tool for attachment to a robot arm. Thus, array 814 of reaction vessels is stationary, and container 800 with attached tube 806 is moved form one reaction vessel to another by the robot arm. Alternatively, this apparatus can be configured as a stationary workstation. In such an embodiment, container 800 is fixed by a support, and array 814 of reaction vessels is moved under tube 806 and then lifted for access to individual reaction vessels by, e.g., a robot arm with a gripper tool. A work station embodiment is preferred if arrays of reaction vessels are moved between other work stations by robot arms.

All the tools and work stations adapted to fluid handling, which have been described in embodiments directed to robotic synthesis systems, can be easily and usefully adapted to use in bench environments in which manual operations replace robotic operations. In such a bench environment, manual actuation of work station controls can replace automatic actuation where useful. In particular, the slurry distribution tool can be configured for standalone use without robot arms. In this case, valve 803 and suction source 801 can be either manually or automatically controlled.

Additional robot arm tools and work stations adapted to the previously described reaction vessel arrays include additional types of robot arm grippers, temperature controlled incubation stations, agitators for reaction vessel arrays, tools for tightening or loosening reaction vessel caps, and so forth.

5.4. Control Elements

It is advantageous that substantially all processing elements of an automatic synthesis robot according to this invention be under automatic control having certain facilities. Individual processing resources or facilities—for example, robot arms, work station, and tools—should be controllable in order that final compounds can be completely and automatically synthesized from input building blocks and reagents according to various and different synthesis protocols. The automatic control should also be sufficiently general that a different final compound can be synthesized in each reaction vessel of each array of reaction vessels present in the robot, and that a different combinatorial synthesis protocol can be performed in the reaction vessels of each reaction vessel array present in the robot. Finally, the automatic control should be able to manage a plurality of reaction vessels, arrays of reaction vessels, work stations, robot arms, and robot arm tools so that all of the processing resources or facilities of an embodiment of this robot are optimally engaged or facilities in performing tasks for the synthesis being carried out by the robot. One exemplary criterion for optimal employment of robot processing resources is that all such resources be utilized, or busy, for approximately the same fraction of processing or synthesis time. In this manner no one resource is a bottle-neck causing under-utilization of other resources or processing delays for compound synthesis.

Although fully automatic control is preferable, this invention is adapted to controls requiring manual intervention for certain, or even all, processing steps.

These automatic control facilities are supported by certain hardware and software elements. General hardware elements preferably include one or more general control computers, an optional number of specialized control processors, and electrical interfaces to all controlled processing resources of the robot. In a manner known in the art, all the directly and indirectly controlled resources of the robot can be provided with electrical interfaces having certain standardized electrical characteristics. Certain of these low-level hardware interfaces are directly linked from their standardized interfaces to interfaces of the general control computers. Optionally, for complex resources, such as complex work stations or the robot arms, an intermediate level of specialized control processors is interposed between the general control computers and the low-level electrical interfaces of such resources.

The general control computers can be sufficiently capable personal computers provided with such specialized electrical interfaces. An exemplary personal computer includes an Intel Pentium™ processor running at 133 Mhz, a 1 gigabyte or greater hard drive, 16 megabytes or more of memory, and commercially available interface boards providing interfaces such as D/A or on/off output circuits or links to standard instrument control buses. These hardware control elements are provided by such commercial suppliers as SAIC, Inc.

General software elements executed by the general control computers include operating system software, low-level moment-to-moment control and monitoring software, robot scheduling and monitoring software, and synthesis planning software. At the lowest software level is the operating system software of the general control computers, which in an exemplary embodiment, can be Unix™ or Windows NT™ (Microsoft Corporation). The low-level moment-to-moment control and monitoring software inputs scripts describing in detail robot actions to perform and outputs electrical control signals to the controlled processing resources through the interfaces attached to the general control computers. These signals cause robot and work station actions to be performed. At the next software level is robot scheduling software, which inputs a description of the synthetic steps to be performed, the locations of stored building blocks and reagents, the location and type of available work stations, the location and type of available interchangeable tools, and so forth, and outputs the detailed command scripts controlling robot functions. These scripts are interpreted by the moment-to-moment control and monitoring software. At the highest software level is chemical synthesis planning software, which inputs a description of the synthetic protocols available in a particular embodiment of this robot and the desired compounds to be synthesized, and then outputs the synthetic steps necessary to synthesize the desired compounds in a form usable by the scheduling software. An exemplary embodiment the low-level moment-to-moment control software and the scheduling software are supplied by SAIC, Inc.

Tables 1, 2, and 3 illustrates exemplary robot control scripts, such as those output by the scheduling software and input by the moment-to-moment control software in order to generate electrical signals actuating controlled elements of the robot. These scripts are directed to the embodiment of the robot illustrated in FIG. 1 processing ball-sealed, stackable reaction vessels according to the method illustrated in FIG. 3. These scripts provide for arm control by using such elementary commands as: grip, for having a robot arm grip a reaction vessel array with a gripper tool; transfer, for causing a robot arm to move a gripped array between two locations automatically avoiding intervening obstacles; interchange, for having a robot arm attach a new arm tool; and activate, for having a robot arm activate and use a particular tool.

TABLE 1

| ARM NO. 2 (in FIG. 1) | |
|---|---|
| Step | Action |
| 1 | Grip the holding block with unsealed reaction vessels from the assembly/disassembly station 14 |
| 2 | Transfer the holding block with reaction vessels to the solvent dispensing work station 15 |
| 3 | Transfer the holding block with reaction vessels to the solvent aspiration work station 16 |
| 4 | Repeat washing steps 2 and 3 for N times |
| 5 | Transfer the holding block with reaction vessels to the building block distribution location 12 |
| 6 | Grip the holding block with fully charged reaction vessels |
| 7 | Transfer the holding block with reaction vessels to the assembly/disassembly work station 14 |

According to the exemplary control script in Table 1, robot arm 2 prepares a reaction vessel array for a new building block addition step. First, it grips a reaction vessel array that has just been disassembled from a hot rod at assembly/disassembly work station 14. Then it transfers this array repetitively between solvent aspiration work station 16 and solvent dispensing work station 15, for preforming a selected number of wash cycles. It then transfer this reaction vessel array to location 12 for building block and reagent distribution. Finally, it grips and transfers a fully charged reaction vessel array at this location back to assembly/disassembly station work 14, for assembling the reaction vessels into a hot rod.

TABLE 2

ARM NO. 3 (in FIG. 1)

| Step | Action |
|---|---|
| 1 | Activate a building block dispensing tool to distribute building blockS, and a reagent dispensing tool to dispense reagents to the reaction vessels in an array; during this process interchange tools and grip building block syringes as needed |
| 2 | Interchange tools, attaching a hot rod agitation tool |
| 3 | Activate a hot rod agitation tool to couple the motor to the hot rods in the incubation ports 9. |
| 4 | Activate a hot rod agitation tool to spin the hot rod for 5 sec |
| 5 | Activate a hot rod agitation tool to decouple the motor from the hot rod |
| 6 | Repeat step 3, 4 and 5 for all hot rods in the incubation ports 9 |
| 7 | Interchange tools, attaching building block and reagent dispensing tools |

Concurrently, arm 3 performs two functions, distributing building block solutions and reagents and agitating hot rods during their incubation. First, arm 3, using building block distribution tool for gripping syringes 20, grips syringes with building block solutions, and distributes then to reaction vessels in array 12. It also distributes activating and other reagents to the same reaction vessel array using appropriate reagent distribution tools. Then it interchanges tools, attaching an agitation tool, moves to the incubation array ports 9, and couples to and agitates intermittently all the hot rods being incubated.

TABLE 3

ARM NO. 4 (in FIG. 1)

| Step | Action |
|---|---|
| 1 | Grip a hot rod from incubator ports 9 |
| 2 | Transfer the hot rod to the assembly/disassembly work station 14 |
| 3 | Grip the assembled hot rod from the assembly/disassembly work station |
| 4 | Transfer the assembled hot rod to incubator ports 9 |

Finally, during the activities of arms 2 and 3, arm 4 grips and transfers assembled hot rods from the assembly/disassembly work station 14 to the incubator ports 9 for incubation, and then returns them to the assembly/disassembly station after incubation for disassembly into a rectangular reaction vessel array in a holding block.

These robot arm commands and command sequences are exemplary, and this invention is adaptable to other such similar commands and command sequences as can be output by the scheduling software in response to commands requesting the synthesis of particular compounds.

5.5. Standalone Embodiments

Although this invention has been described primarily with respect to use of the disclosed reaction vessels, reaction vessel arrays, work stations, and tools in an integrated and automatic robot apparatus, this invention is not so limited. All the reaction vessel embodiments, workstations, and tools have use in other environments, such as only partially integrated robots or entirely manual use on a laboratory benchtop. Accordingly, this invention further comprises each of these elements and sub-elements individually for use in such manual and semi-automated environments. In these environments, the manipulations described as being performed by robot arms can instead be performed by hand. Further, the various elements can optionally have a more limited range of automatic actuators, requiring manual attention to, e.g., actuate valves and so forth.

6. EXAMPLES

The invention is further described in the following example which is in no way intended to limit the scope of the invention.

6.1. Example 1

Tetrahydroisoquinolinone Library Synthesis

A library of 2,280 different tetrahydroisoqinolinone amides was synthesized according to the chemistry illustrated below by using the stations and tools previously described.

TETRAHYDROISOQINOLINONE AMIDE LIBRARY CHEMISTRY

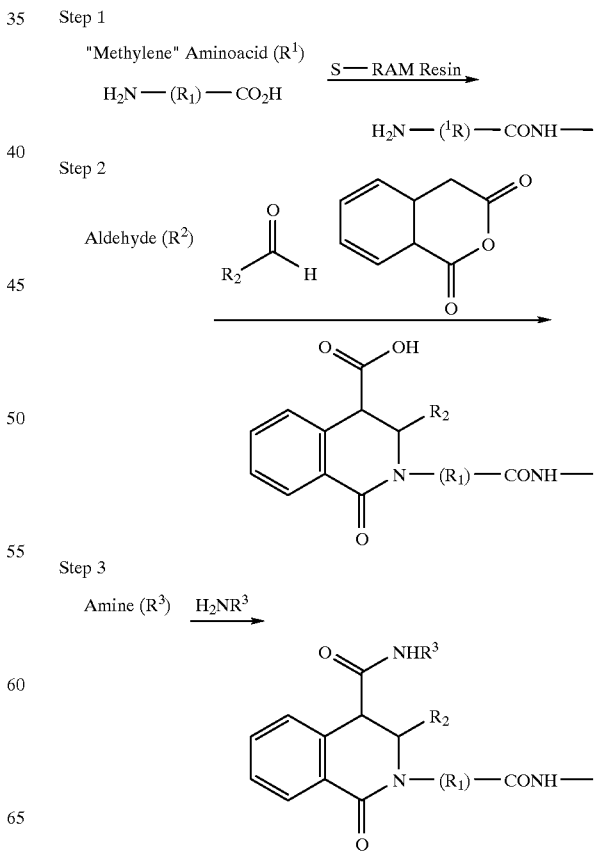

Step 4

"Cleave from Resin"  TFA

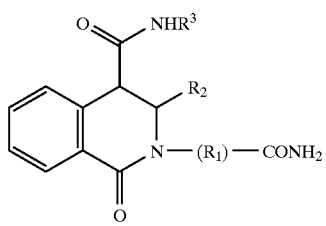

In general, a separate tetrahydroisoqinolinone amide was synthesized attached to solid-phase support in separate reaction vessels by performing three addition steps: a first step in which one of 10 amino acid building blocks was added; a second step in which one of 38 aldehyde building blocks was added; and a third step in which one of 6 amine building blocks were added (10*38*6=2280). The building blocks used are listed in Table 4. The synthesis steps described in this example were performed using the work stations and tools with a combination of manual and robotic assistance.

TABLE 4

LIBRARY BUILDING BLOCKS

| Amino Acid Solutions - 0.3M Fmoc protected amino acid in a solution of 0.3M N-hydroxybenzotriazole and 0.3M diisopropylcarbodiimide | MW (Fmoc) |
|---|---|
| 1  2-Aminoethanoic Acid | 297 |
| 2  3-Aminopropionic Acid | 311 |
| 3  5-Aminopentanoic Acid | 339 |
| 4  7-Aminoheptanoic Acid | 367 |
| 5  (S)2,3-Diaminopropionic Acid (Fmoc on side chain) | 426 |
| 6  (S)-2,6-Diaminohexanoic Acid (Fmoc on side chain) | 469 |
| 7  (S)/(R)-3-Amino-2-methylpropionic Acid | 325 |
| 8  2-(2-Aminoethoxyethoxy)acetic Acid | 385 |
| 9  trans-4-(Aminomethyl)cyclohexanecarboxylic Acid | 380 |
| 10  4-(Aminomethyl)benzoic Acid | 373 |

| Aldehyde Solutions - 0.5M aldehyde solution in dimethylformamide | MW |
|---|---|
| 1  1,4-Benzodioxan-6-carboxaldehyde | 164 |
| 2  1-Methylindole-3-carboxaldehyde | 159 |
| 3  2,3-Difluorobenzaldehyde | 142 |
| 4  2-Bromobenzaldehyde | 185 |
| 5  2-Chloro-5-nitrobenzaldehyde | 186 |
| 6  2-Furaldehyde | 96 |
| 7  2-Imidazolecarboxaldehyde | 96 |
| 8  2-Naphthaldehyde | 156 |
| 9  2-Pyridinecarboxaldehyde | 107 |
| 10  2-Thiophenecarboxaldehyde | 112 |
| 11  3,4-Dichlorobenzaldehyde | 175 |
| 12  3,5-bis(trifluoromethyl)benzaldehyde | 242 |
| 13  3,5-Dihydroxybenzaldehyde | 138 |
| 14  3,5-Dihydroxybenzaldehyde | 166 |
| 15  3,5-Dimethyl-4-hydroxybenzaldehyde | 150 |
| 16  3-(4-Methoxyphenoxy)benzaldehyde | 228 |
| 17  3-Furaldehyde | 96 |
| 18  3-Hydroxybenzaldehyde | 122 |
| 19  3-Methyl-4-methoxybenzaldehyde | 150 |
| 20  3-Methylbenzaldehyde | 120 |
| 21  3-Nitrobenzaldehyde | 151 |
| 22  3-Pyridinecarboxaldehyde | 107 |
| 23  3-Thiophenecarboxaldehyde | 112 |
| 24  4-(3-Dimethylaminopropoxy)benzaldehyde | 207 |
| 25  4-(Dimethylamino)benzaldehyde | 149 |
| 26  4-(Methylthio)benzaldyde | 152 |
| 27  4-(Trifluoromethyl)benzaldehyde | 174 |
| 28  4-Biphenylcarboxaldehyde | 182 |

TABLE 4-continued

LIBRARY BUILDING BLOCKS

| 29  4-Bromo-2-thiophenecarboxaldehyde | 191 |
|---|---|
| 30  4-Cyanobenzaldehyde | 131 |
| 31  4-Methoxy-1-Naphthaldehyde | 186 |
| 32  4-Nitrobenzaldehyde | 151 |
| 33  4-Pyridinecarboxaldehyde | 107 |
| 34  5-(Hydroxymethyl)-2-furaldehyde | 126 |
| 35  5-Bromo-4-hydroxy-3-methoxybenzaldehyde | 231 |
| 36  5-Nitor-2-furaldehyde | 141 |
| 37  6-Methyl-2-pyridinecarboxaldehyde | 121 |
| 38  Benzaldehyde | 106 |

| Amine Solutions - 1.0M amine solution in dimethylformamide | Amine mg/ml |
|---|---|
| 1  Tryptamine | 9.6 |
| 2  (+/−)-3-(1-Hydroxyethyl)aniline | 8.22 |
| 3  3,4,5-Trimethoxyaniline | 10.98 |
| 4  3,5-Dimethoxyaniline | 9.18 |
| 5  (+/−)-endo-2-Aminonorbornane | 8.88 |
| 6  4-(Dimethylamino)benzylamine | 13.38 |

In a pre-processing step, the reaction vessels were arrayed and charged with solid-phase support. Each of 24 microtitre-plate holding blocks was filled with 96 polypropylene test-tube reaction vessels of 1.2 ml volume, for a total of 2,280 test tube reaction vessels. (The last tube in each microtitre-plate was not used.) Then twenty-four grams of polyoxyethylene-grafted polystyrene beads, having an average size of 90 $\mu$m, a substitution capacity of 0.24 mmol/g, and attached acid labile linker (TentaGel S RAM), were equally distributed to all the test tubes using the resin distribution tool described herein.

The amino acid addition step was performed using the freshly charged reaction vessels. Microtitre plates were placed, eight at a time, on the surface of the robotic platform at a building block distribution station, and one of the ten amino acid solutions were distributed into individual test tube reaction vessels from storage containers. The 96 wells of each microtitre plate received 100 $\mu$l of the 0.3 M amino acid solutions. Just prior to the distribution to the individual test tubes, 0.5 ml of diisopropylcarbodiimide was added to the stock solutions of the amino acids. A computer generated protocol based on the compounds to be synthesized and the available building blocks, determined which building blocks, here which amino acids, to distribute to which test tubes.

After distribution of amino acids, the microtitre plates were capped with a compliant array of sealing balls and shaken overnight. Microtitre plates with settled resin beads were then transferred to the previously described solvent-removal station configured with an array of 96 needles conforming to the microtitre plate layout, and solutions were aspirated simultaneously from all 96 test tubes in one microtitre plate. The microtitre plates were then transferred to a 96 needle wash station, as previously described, and 25 ml per microtitre plate of dimethylformamide ("DMF") was dispensed into the test tubes in such a way that the resin was thoroughly mixed by the DMF. After the resin settled, the DMF was aspirated by the solvent-removal station. This DMF washing cycle of dispensing and aspirating of the work stations was repeated three times. The microtitre plates were transferred to a 96 needle solvent-distribution station and a solution of 50% piperidine in DMF was added simultaneously to all the test tubes of a microtitre plate in order to remove the Fmoc protecting groups. The microtitre plates were capped with a compliant array of sealing balls and shaken for 15 minutes. The piperidine solution was then removed with a 96 needle solvent-removal station, and DMF wash cycles of dispensing and aspirating were repeated 5 times.

Next, the aldehyde addition step was performed. Microtitre plates were transferred to a building block distribution station, and the 0.5 M aldehyde solution was distributed from storage containers to each of the 96 wells of each microtitre plate, each well receiving 100 $\mu$l of solution. Next, a solution of trimethylorthoformiate in DMF, 100 $\mu$l per microtitre plate well, was added to all wells for a final concentration of 0.25 M aldehyde and 0.5 M trimethylorthoformiate. The microtitre plates were capped with a compliant array of sealing balls and placed on a shaker. After 3 hours of shaking, the plates were washed, again in the 96 needle aspirating and dispensing wash station, with 0.2 M trimethylorthoformiate in DMF (2x). Then homophthalic anhydride solution was added to the test tubes, 125 $\mu$l per well of 0.4 M anhydride solution with 0.03 M diisopropylethylamine in DMF. The base was added immediately prior to the anhydride solution distribution. After shaking at room temperature overnight, the plates were washed 3 times with DMF, two times with water, and 3 times with DMF in the 96 needle aspirating and dispensing wash station. Each wash used 25 ml of wash solution per microtitre plate.

Finally, the amine addition step was performed. To each test tube, a 100 $\mu$l solution of 0.3 M HATU in DMF was distributed and then aspirated after a 20 minute incubation. After one wash with DMF at the 96 needle aspiration and dispensing wash station, 150 $\mu$l per microtitre plate well of one of the amine solutions was distributed from storage containers to each of the test tubes in the microtitre plates. Plates were shaken for 1 hour at room temperature and washed twice with DMF. Then the HATU solution was distributed as previously, and removed after a 20 minute incubation. After one wash with DMF, the amine solutions were distributed again as previously, and plates were capped with a compliant array of sealing balls and shaken overnight. Next, the amine solutions were removed from the microtitre plates, and solid phase was washed at the 96 needle aspirating and dispensing wash station: three times with DMF, once with water, 3 times with DMF, and 3 times with tertbutylmethylether.

The microtitre plates were dried in vacuo. Trifluoroacetic acid, 200 $\mu$l per test tube, was distributed to the microtitre plates. After incubation for 2 hours at room temperature, the test tube contents were evaporated in an evacuated centrifuge, such as the SpeedVac from Savant (Holbrook, N.Y.). A methanol extraction was then performed. Methanol, 300 $\mu$l per test tube, was distributed into the dry resin in microtitre plates and the methanolic solution was transferred into new microtitre plates. This process was repeated three times.

In a post-processing step, the resulting library compounds were analyzed. Twenty micro-liter samples were taken from each test tube containing the combined methanolic extractions for liquid chromatographic and mass spectrometric analysis. The remainder of the solution was evaporated to dryness in the SpeedVac.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

Various publications are cited herein, the disclosures of which are incorporated by reference in their entireties.

What is claimed is:

1. An integrated apparatus for performing combinatorial-chemistry synthetic reactions comprising:
   a. means for containing one or more of a plurality of combinatorial-chemistry synthetic reactions, each said means for containing having an aperture for aspirating a fluid from and for dispensing a fluid into the interior of said containing means;
   b. means for sealing said apertures of said containing means;
   c. means for dispensing a selected one or more of a plurality fluids into said containing means;
   d. means for aspirating fluids from said containing means; and
   e. robot arm means for gripping one or more of said containing means and transporting said means for containing between said means for sealing, said means for dispensing, and said means for aspirating,
      wherein said means for sealing comprises a plurality of means for sealing, and wherein said robot arm means is further capable of gripping and transporting one of said means for sealing and engaging it with one or a plurality of containing means in order to seal said plurality of containing means,
      whereby said integrated apparatus can perform a protocol for said combinatorial-chemistry synthetic reactions.

2. The integrated apparatus of claim 1 further comprising storage means for storing a plurality of storage containers, each said storage container holding one of said plurality of fluids, wherein said robot arms means is further capable of gripping said storage containers, and wherein said storage means stores said containers so that they are accessible for gripping by said robot arm means.

3. The integrated apparatus of claim 1 wherein said means for dispensing comprises means for dispensing selected individual fluids into selected ones of said containing means, and wherein said robot arm means is further capable of gripping and transporting said means for dispensing individual fluids in order to dispense individual fluids into selected single ones of said containing means.

4. The integrated apparatus of claim 1 wherein said robot arm means comprises one or more robot arms each capable of attaching and actuating tools for gripping one or more of said containing means and for gripping said means for dispensing fluids.

5. The integrated apparatus of claim 1 wherein said containing means and said means for sealing further comprise:
   a. a plurality of individual fluid containers, each said individual container having a septum with said aperture, said aperture being substantially circular and capable of being sealed by a ball;
   b. a plurality of balls for sealing said individual containers;
   c. a plurality of holding blocks, each said holding block, capable of holding a plurality of said individual containers in a substantially spatially-regular configuration during the dispensing fluids to or during the aspirating of fluids from the interior of said individual containers; and
   d. a plurality of cylinders for retaining a plurality of said individual containers sealed by said balls during a temperature controlled incubation.

6. The integrated apparatus of claim 5 further comprising incubation means for temperature controlled incubation of said cylinders.

7. The integrated apparatus of claim 5 further comprising a plurality of retaining clips, each said retaining clip for engaging a base of each said cylinder for retaining said plurality of individual containers during said incubation.

8. The integrated apparatus of claim 5 further comprising an assembly/disassembly workstation means for moving a plurality of said individual containers and said sealing balls into one or more of said plurality of cylinders from one or more of said holding blocks, and for removing a plurality of said individual containers from one or more of said cylinders into one or more of said holding blocks.

9. The integrated apparatus of claim 8 wherein each of said cylinders further comprises one or more rotatably-mounted clips for retaining said individual containers and said sealing balls during processing by said assembly/disassembly workstation means.

10. The integrated apparatus of claim 1 wherein said containing means further comprises a plurality of reaction vessel arrays, each said reaction vessel array comprising a substantially spatially-regular array of individual containers for individual combinatorial chemistry synthetic reactions.

11. The integrated apparatus of claim 10 wherein said means for sealing said apertures further comprises a plurality of individual means for sealing, each individual means for sealing adapted to seal the apertures of said individual containers of said reaction vessel arrays, each said individual means for sealing comprising:

a. a plate sized to cover said apertures of said individual containers of one of said reaction vessel arrays;

b. one or more clips attached to said plate and engaging with said reaction vessel array to fix said plate to said reaction vessel array; and c. sealing surface means attached to one surface of said plate for engaging with and for sealing said apertures of said individual containers of said reaction vessel array.

12. The integrated apparatus of claim 11 wherein said sealing surface means further comprises a compressible rubber layer.

13. The integrated apparatus of claim 11 wherein said sealing surface means further comprises an inflatable bag, said inflatable bag being inflatable to engage and seal said apertures.

14. The integrated apparatus of claim 11 wherein said apertures are substantially circular and said sealing surface means further comprises a plurality of balls, each ball being attached to said plate and capable of sealing said substantially circular aperture.

15. The integrated apparatus of claim 14 wherein said balls are attached to said plate in a compliant manner permitting said balls to move laterally in order to engage said substantially circular apertures.

16. The integrated apparatus of claim 10 wherein said reaction vessel arrays comprise individual containers integrally formed in said reaction vessel array.

17. The integrated apparatus of claim 16 wherein said reaction vessel arrays are microtiter plates or ELISA plates.

18. The integrated apparatus of claim 10 wherein said individual containers are separate and independent containers, and wherein said reaction vessel arrays are capable of holding said separate and independent containers in a substantially spatially-regular configuration.

19. The integrated apparatus of claim 18 wherein said sealing means further comprise:

a. a plurality of caps, one of said caps being attached to each independent container and having a valve orifice permitting fluid communication between the interior and the exterior of said independent container;

b. a plurality of valve rods containing a plurality of valve rod orifices, each said rod movably mounted in a certain plurality of said caps and capable of motion between (i) a first position in which said rod occludes said valve orifices of said certain plurality of caps thereby sealing the attached containers, and (ii) a second position in which said valve rod orifices are aligned with said valve orifices of said certain plurality of caps thereby opening the interiors of the attached containers to fluid communication with the exterior; and c. a linkage segment for fixing a plurality of valve rods for simultaneous motion so that a plurality of independent containers in one of said reaction vessel arrays can be simultaneously sealed or simultaneously opened by causing motion of said linkage segment.

20. The integrated apparatus of claim 18 wherein said sealing means comprise a plurality of septums, one of said septums sealing said aperture of each independent container and made of a material capable of being punctured by a fluid-manipulating needle and of resealing upon withdrawal of said needle.

21. The integrated apparatus of claim 20 wherein said sealing means further comprises:

a. a plurality of compressible collars, each compressible collar having a collapsible central orifice and being disposed adjacent to said septum sealing each independent container; and b. a plurality of screw caps for exerting pressure on said compressible collars in order to collapse said central orifice and to further seal each said independent container.

22. The integrated apparatus of claim 10 wherein said individual containers comprise syringe bodies, wherein said means for sealing further comprise plungers adapted to fit in and seal said syringe bodies, and wherein said integrated apparatus further comprises a plurality of plunger holders, said plungers sealing said syringes of each said reaction vessel array being fixed to one of said plunger holders.

23. The integrated apparatus of claim 22 wherein said means for aspirating and means for dispensing fluids further comprises a plurality of fluid distribution block means, one such distribution block means being linked to each of said reaction vessel arrays and comprising a plurality of internal fluid passageways establishing fluid communication between the interior of each of said syringe bodies and the exterior of said distribution block.

24. The integrated apparatus of claim 23 wherein said plurality of fluid distribution blocks further comprise a plurality of needles, an exterior opening of each said internal fluid distribution passageway is attached to one of said needles.

25. The integrated apparatus of claim 23 wherein said plurality of fluid distribution blocks further comprise a plurality of septums made of a material capable of being punctured by a fluid-manipulating needle and of resealing upon withdrawal of said needle, and wherein an exterior opening of each said internal fluid distribution passageway is sealed by one of said septums.

26. The integrated apparatus of claim 23 wherein said plurality of fluid distribution blocks further comprise a common internal fluid passageway in fluid communication with all said internal fluid distribution passageways and with a common exterior port.

27. The integrated apparatus of claim 1 wherein said means for containing further comprises a plurality of reaction vessel arrays, each said reaction vessel array comprising a substantially spatially-regular array of individual containers for individual combinatorial-chemistry synthetic reactions, and wherein said fluid dispensing means and said fluid aspirating means further comprise a fluid handling workstation means capable of dispensing or aspirating fluids from all the individual containers in one of said reaction vessel arrays simultaneously.

28. The integrated apparatus of claim 27 wherein said fluid handling workstation means further comprises an array of fluid-manipulating needles so spaced and arranged in order that all the needles of said array of needles can simultaneously access all the individual containers of a reaction vessel array for fluid aspirating or dispensing.

* * * * *